US009045541B2

(12) United States Patent
Eckelman et al.

(10) Patent No.: US 9,045,541 B2
(45) Date of Patent: Jun. 2, 2015

(54) CD47 ANTIBODIES AND METHODS OF USE THEREOF

(71) Applicant: InhibRx LLC, La Jolla, CA (US)

(72) Inventors: Brendan Eckelman, La Jolla, CA (US); John Timmer, La Jolla, CA (US); Amir Razai, La Jolla, CA (US); Quinn Deveraux, La Jolla, CA (US); Kyle Jones, La Jolla, CA (US); Peter L. Nguy, La Jolla, CA (US)

(73) Assignee: InhibRx LLC, La Jolla, CA (US)

( * ) Notice: Subject to any disclaimer, the term of this patent is extended or adjusted under 35 U.S.C. 154(b) by 0 days.

(21) Appl. No.: 13/761,087

(22) Filed: Feb. 6, 2013

(65) Prior Publication Data

US 2013/0224188 A1  Aug. 29, 2013

Related U.S. Application Data

(60) Provisional application No. 61/595,216, filed on Feb. 6, 2012, provisional application No. 61/659,752, filed on Jun. 14, 2012.

(51) Int. Cl.
*C07K 16/28* (2006.01)
*C07K 16/30* (2006.01)
*C07K 14/705* (2006.01)
*A61K 45/06* (2006.01)
*A61K 39/395* (2006.01)
*A61K 39/00* (2006.01)

(52) U.S. Cl.
CPC ....... *C07K 16/2803* (2013.01); *C07K 14/70503* (2013.01); *A61K 45/06* (2013.01); *A61K 39/39558* (2013.01); *C07K 2319/21* (2013.01); *A61K 2039/505* (2013.01); *C07K 2317/24* (2013.01); *C07K 2317/34* (2013.01); *C07K 2317/565* (2013.01); *C07K 2317/70* (2013.01); *C07K 2317/76* (2013.01)

(58) Field of Classification Search
CPC ......... C07K 16/2896; C07K 2317/70–2317/77
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,816,567 A | 3/1989 | Cabilly et al. |
| 4,946,778 A | 8/1990 | Ladner et al. |
| 5,013,556 A | 5/1991 | Woodle et al. |
| 5,030,719 A | 7/1991 | Umemoto et al. |
| 5,057,604 A | 10/1991 | Brown |
| 5,101,827 A | 4/1992 | Goldenberg |
| 5,102,990 A | 4/1992 | Rhodes |
| 5,151,510 A | 9/1992 | Stec et al. |
| 5,194,594 A | 3/1993 | Khawli et al. |
| 5,223,409 A | 6/1993 | Ladner et al. |
| 5,530,101 A | 6/1996 | Queen et al. |
| 5,545,806 A | 8/1996 | Lonberg et al. |
| 5,545,807 A | 8/1996 | Surani et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torii et al. |
| 5,697,902 A | 12/1997 | Goldenberg |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnson et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |

(Continued)

FOREIGN PATENT DOCUMENTS

| | | |
|---|---|---|
| EP | 0463151 B1 | 6/1996 |
| EP | 0773288 A2 | 5/1997 |

(Continued)

OTHER PUBLICATIONS

Almagro & Fransson, Frontiers in Bioscience 2008; 13:1619-33.*
PJ Carter, Nat Rev Immunol, 2006; 6:343-357.*
"Production of Monoclonal Antibodies." *Monoclonal Antibodies: Principles and Practice.* Goding, ed. Boston: Academic Press. Chapter 3(1986):59-103.
Alegre et al. "Effect of a Single Amino Acid Mutation on the Activating and Immunosuppressive Properties of a "Humanized" OKT3 Monoclonal Antibody." *J. Immunol.* 148.11(1992):3461-3468.
Baldrick et al. "Pharmaceutical Excipient Development: The Need for Preclinical Guidance." *Regul. Toxicol. Pharmacol.* 32.2(2000):210-218.
Barker et al. "Detecting Distant Relationships: Computer Methods and Results." *Atlas of Protein Sequence and Structure.* Dayhoff, ed. Washington, D.C.: National Biomedical Research Foundation. 5(1972)101-110.

(Continued)

*Primary Examiner* — Sheela J Huff
*Assistant Examiner* — Jessica H Roark
(74) *Attorney, Agent, or Firm* — Morrison & Foerster LLP

(57) ABSTRACT

This invention relates generally to monoclonal antibodies that recognize CD47, more specifically to CD47 antibodies that do not cause a significant level of agglutination of cells, to methods of generating these antibodies, and to methods of using these monoclonal antibodies as therapeutics.

21 Claims, 19 Drawing Sheets

(56) References Cited

U.S. PATENT DOCUMENTS

| | | |
|---|---|---|
| 5,939,598 A | 8/1999 | Kucherlapati et al. |
| 6,023,010 A | 2/2000 | Krimpenfort et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,255,458 B1 | 7/2001 | Lonberg et al. |
| 6,521,404 B1 | 2/2003 | Griffiths et al. |
| 7,217,568 B2 | 5/2007 | Jamieson et al. |
| 7,282,556 B2 | 10/2007 | Parkos |
| 7,514,229 B2 | 4/2009 | Jamieson et al. |
| 7,622,255 B2 | 11/2009 | Jamieson et al. |
| 7,723,483 B2 | 5/2010 | Clemmons et al. |
| 7,816,088 B2 | 10/2010 | Jamieson et al. |
| 8,153,388 B2 | 4/2012 | Jamieson et al. |
| 8,187,595 B2 | 5/2012 | Clemmons et al. |
| 8,206,706 B2 | 6/2012 | Clemmons et al. |
| 8,361,736 B2 | 1/2013 | Majeti et al. |
| 8,562,997 B2 | 10/2013 | Jaiswal et al. |
| 8,613,922 B2 | 12/2013 | Clemmons et al. |
| 8,709,429 B2 | 4/2014 | Majeti et al. |
| 8,758,750 B2 | 6/2014 | Weissman et al. |
| 2004/0018531 A1 | 1/2004 | Jamieson et al. |
| 2004/0147731 A1 | 7/2004 | Parkos |
| 2004/0213792 A1 | 10/2004 | Clemmons et al. |
| 2005/0288217 A1 | 12/2005 | Clemmons et al. |
| 2005/0288491 A1 | 12/2005 | Wilson et al. |
| 2007/0111238 A1 | 5/2007 | Jamieson et al. |
| 2007/0148163 A1 | 6/2007 | Takahashi et al. |
| 2007/0238127 A1 | 10/2007 | Jamieson et al. |
| 2008/0131431 A1 | 6/2008 | Smith et al. |
| 2008/0160013 A1 | 7/2008 | Clemmons et al. |
| 2009/0035322 A1 | 2/2009 | Martin et al. |
| 2009/0148905 A1 | 6/2009 | Ashman et al. |
| 2009/0191202 A1 | 7/2009 | Jamieson et al. |
| 2009/0226452 A1 | 9/2009 | Clemmons et al. |
| 2009/0280127 A1 | 11/2009 | Clemmons et al. |
| 2010/0215640 A1 | 8/2010 | Clemmons et al. |
| 2011/0014119 A1 | 1/2011 | Jaiswal et al. |
| 2011/0015090 A1 | 1/2011 | Majeti et al. |
| 2011/0076683 A1 | 3/2011 | Jamieson et al. |
| 2011/0223107 A1 | 9/2011 | Tremblay et al. |
| 2012/0039896 A1 | 2/2012 | Clemmons et al. |
| 2012/0156724 A1 | 6/2012 | Kikuchi et al. |
| 2012/0225073 A1 | 9/2012 | Weissman et al. |
| 2012/0269816 A1 | 10/2012 | Clemmons et al. |
| 2012/0282174 A1 | 11/2012 | Weissman et al. |
| 2012/0283124 A1 | 11/2012 | Park et al. |
| 2013/0142786 A1 | 6/2013 | Liu et al. |
| 2013/0244326 A1 | 9/2013 | Majeti et al. |
| 2013/0281304 A1 | 10/2013 | Feinberg et al. |
| 2014/0065169 A1 | 3/2014 | Jaiswal et al. |
| 2014/0072568 A1 | 3/2014 | Clemmons et al. |
| 2014/0140989 A1* | 5/2014 | Eckelman et al. ......... 424/133.1 |
| 2014/0141002 A1 | 5/2014 | Clemmons et al. |
| 2014/0161805 A1 | 6/2014 | Jamieson et al. |
| 2014/0161825 A1 | 6/2014 | Jaiswal et al. |

FOREIGN PATENT DOCUMENTS

| | | |
|---|---|---|
| EP | 0546073 B1 | 9/1997 |
| EP | 0843961 A1 | 5/1998 |
| JP | 3068180 B2 | 7/2000 |
| JP | 3068506 B2 | 7/2000 |
| JP | 3068507 B2 | 7/2000 |
| WO | WO-9100360 A1 | 1/1991 |
| WO | WO-9201047 A1 | 1/1992 |
| WO | WO-9203918 A1 | 3/1992 |
| WO | WO-9220373 A1 | 11/1992 |
| WO | WO-9222645 A1 | 12/1992 |
| WO | WO-9222647 A1 | 12/1992 |
| WO | WO-9222670 A1 | 12/1992 |
| WO | WO-9308829 A1 | 5/1993 |
| WO | WO-9312227 A1 | 6/1993 |
| WO | WO-9400569 A1 | 1/1994 |
| WO | WO-9402602 A1 | 2/1994 |
| WO | WO-9411026 A2 | 5/1994 |
| WO | WO-94/25585 A1 | 11/1994 |
| WO | WO-9425588 A2 | 11/1994 |
| WO | WO-9429444 A1 | 12/1994 |
| WO | WO-9522618 A1 | 8/1995 |
| WO | WO-9614436 A1 | 5/1996 |
| WO | WO-9627011 A1 | 9/1996 |
| WO | WO-9634096 A1 | 10/1996 |
| WO | WO-9713852 A1 | 4/1997 |
| WO | WO-9738137 A1 | 10/1997 |
| WO | WO-9824884 A1 | 6/1998 |
| WO | WO-9824893 A2 | 6/1998 |
| WO | WO-0076310 A1 | 12/2000 |
| WO | WO-03/102215 A2 | 12/2003 |
| WO | WO-03/102215 A3 | 12/2003 |
| WO | WO-2004/014292 A2 | 2/2004 |
| WO | WO-2004/014292 A3 | 2/2004 |
| WO | WO-2004/096133 A2 | 11/2004 |
| WO | WO-2004-096133 A3 | 11/2004 |
| WO | WO-2005/057172 A2 | 6/2005 |
| WO | WO-2005/057172 A3 | 6/2005 |
| WO | WO-2005/117936 A2 | 12/2005 |
| WO | WO-2005/117936 A3 | 12/2005 |
| WO | WO-2009/091547 A1 | 7/2009 |
| WO | WO-2009/091601 A1 | 7/2009 |
| WO | WO-2010/017598 A1 | 2/2010 |
| WO | WO-2011/034969 A1 | 3/2011 |
| WO | WO-2011/041453 A1 | 4/2011 |
| WO | WO-2011/059972 A1 | 5/2011 |
| WO | WO-2011/143624 A2 | 11/2011 |
| WO | WO-2011/143624 A3 | 11/2011 |
| WO | WO-2012/021867 A2 | 2/2012 |
| WO | WO-2012/021867 A3 | 2/2012 |
| WO | WO-2012/088309 A1 | 6/2012 |
| WO | WO-2013/032948 A1 | 3/2013 |
| WO | WO-2013/109752 A1 | 7/2013 |
| WO | WO-2013/119714 A1 | 8/2013 |
| WO | WO-2014/036385 A1 | 3/2014 |

OTHER PUBLICATIONS

Blake et al. "Evaluation of Peptide Libraries: An Iterative Strategy to Analyze the Reactivity of Peptide Mixtures with Antibodies." *Bioconjug. Chem.* 3.6(1992):510-513.

Blazar et al. "CD47 (Integrin-Associated Protein) Engagement of Dendritic Cell and Macrophage Counterreceptors is Required to Prevent the Clearance of Donor Lymphohematopoietic Cells." *J. Exp. Med.* 194.4(2001):541-549.

Bobo et al. "Convection-Enhanced Delivery of Macromolecules in the Brain." *PNAS.* 91.6(1994):2076-2080.

Bowie et al. "A Method to Identify Protein Sequences That Fold into a Known Three-Dimensional Structure." *Science.* 253.5016(1991):164-170.

Brennan et al. "Preparation of Bispecific Antibodies by Chemical Recombination of Monoclonal Immunoglobulin G1 Fragments." *Science.* 229.4708(1995):81-83.

Brodeur et al. "Mouse-Human Myeloma Partners for the Production of Heterohybridomas." *Monoclonal Antibody Production Techniques and Applications.* New York: Marcel Dekker, Inc. (1987):51-63.

Brown et al. "Integrin-Associated Protein (CD47) and its Ligands." *Trends Cell Biol.* 11.3(2001):130-135.

Carell et al. "A Novel Procedure for the Synthesis of Libraries Containing Small Organic Molecules." *Angew. Chem. Int. Ed.* 33.20(1994):2059-2061.

Caron et al. "Engineered Humanized Dimeric Forms of IgG are More Effective Antibodies." *J. Exp. Med.* 176.4(1992):1191-1195.

Carter. "Bispecific Human IgG by Design." *J. Immunol. Methods.* 248.1-2(2001):7-15.

Chan et al. "Cancer Stem Cells in Bladder Cancer: A Revisited and Evolving Concept." *Curr. Opin. Urol.* 20.5(2010):393-397.

Chan et al. "Identification, Molecular Characterization, Clinical Prognosis, and Therapeutic Targeting of Human Bladder Tumor-Initiating Cells." *PNAS.* 106.33(2009):14016-14021.

Chao et al. "The CD47-SIRPα Pathway in Cancer Immune Evasion and Potential Therapeutic Implications." *Curr. Opin. Immunol.* 24.2(2012):225-232.

(56) References Cited

OTHER PUBLICATIONS

Charman. "Lipids, Lipophilic Drugs, and Oral Drug Delivery—Some Emerging Concepts." *J. Pharm. Sci.* 89.8(2000):967-978.
Chen et al. "Intracellular Antibodies as a New Class of Therapeutic Molecules for Gene Therapy." *Hum. Gene Ther.* 5.5(1994):595-601.
Chiswell et al. "Phage Antibodies: Will New 'Coliclonal' Antibodies Replace Monoclonal Antibodies?" *Trends Biotechnol.* 10.3(1992):80-84.
Cho et al. "An Unnatural Biopolymer." *Science.* 261. 5126(1993):1303-1305.
Chothia et al. "Canonical Structures for the Hypervariable Regions of Immunoglobulins." *J. Mol. Biol.* 196.4(1987):901-917.
Chothia et al. "Conformations of Immunoglobulin Hypervariable Regions." *Nature.* 342.6252(1989):877-883.
Cole et al. "The EBV-Hybridoma Technique and its Application to Human Lung Cancer." *Monoclonal Antibodies and Cancer Therapy.* Reisfeld et al., eds. New York: Alan R. Liss, Inc. (1985):77-96.
Cote et al. "Generation of Human Monoclonal Antibodies Reactive With Cellular Antigens." *PNAS.* 80.7(1983):2026-2030.
Csányi et al. "Thrombospondin-1 Regulates Blood Flow via CD47 Receptor-Mediated Activation of NADPH Oxidase 1." *Arterioscler. Thromb. Vasc. Biol.* 32.12(2012):2966-2973.
Cull et al. "Screening for Receptor Ligands Using Large Libraries of Peptides Linked to the C Terminus of the *lac* Repressor." *PNAS.* 89.5(1992):1865-1869.
Cwirla et al. "Peptides on Phage: A Vast Library of Peptides for Identifying Ligands." *PNAS.* 87.16(1990):6378-6382.
Dall'Acqua et al. "Properties of Human IgG1s Engineered for Enhanced Binding to the Neonatal Fc Receptor (FcRn)." *J. Biol. Chem.* 281.33(2006):23514-23524.
Davidson et al. "A Model System for in vivo Gene Transfer into the Central Nervous System Using an Adenoviral Vector." *Nat. Genet.* 3.3(1993):219-223.
Davies et al. "Antibody-Antigen Complexes." *Annu. Rev. Biochem.* 59(1990):439-473.
Dayhoff. "Survey of New Data and Computer Methods of Analysis." *Atlas of Protein Sequence and Structure.* Dayhoff, ed. Washington, D.C.: National Biomedical Research Foundation. 5.S2(1976):1-19.
Devlin et al. "Random Peptide Libraries: A Source of Specific Protein Binding Molecules." *Science.* 249.4967(1990):404-406.
DeWitt et al. "'Diversomers': An Approach to Nonpeptide, Nonoligomeric Chemical Diversity." *PNAS.* 90.15(1993):6909-6913.
Eppstein et al. "Biological Activity of Liposome-Encapsulated Murine Interferon γ is Mediated by a Cell Membrane Receptor." *PNAS.* 82.11(1985):3688-3692.
Erb et al. "Recursive Deconvolution of Combinatorial Chemical Libraries." *PNAS.* 91.24(1994):11422-11426.
Evans et al. "Design of Nonpeptidal Ligands for a Peptide Receptor: Cholecystokinin Antagonists." *J. Med. Chem.* 30.7(1987):1229-1239.
Fanger et al. "Production and Use of Anti-FcR Bispecific Antibodies." *Immunomethods.* 4.1(1994):72-81.
Fauchère et al. "Evaluation of the Stability of Peptides and Pseudopeptides as a Tool in Peptide Drug Design." *J. Adv. Drug Res.* 15(1986):128-159.
Felici et al. "Selection of Antibody Ligands from a Large Library of Oligopeptides Expressed on a Multivalent Exposition Vector." *J. Mol. Biol.* 222.2(1991):301-310.
Fodor et al. "Multiplexed Biochemical Assays with Biological Chips." *Nature.* 364.6437(1993):555-556.
Gallop et al. "Applications of Combinatorial Technologies to Drug Discovery. 1. Background and Peptide Combinatorial Libraries." *J. Med. Chem.* 37.9(1994):1233-1251.
Gao et al. "Integrin-Associated Protein is a Receptor for the C-Terminal Domain of Thrombospondin." *J. Biol. Chem.* 271.1(1996):21-24.
Geller et al. "An HSV-1 Vector Expressing Tyrosine Hydroxylase Causes Production and Release of L-DOPA from Cultured Rat Striatal Cells." *J. Neurochem.* 64.2(1995):487-496.
Geller et al. "Infection of Cultured Central Nervous System Neurons with a Defective Herpes Simplex Virus 1 Vector Results in Stable Expression of *Escherichia coli* β-Galactosidase." *PNAS.* 87.3(1990):1149-1153.
Geller et al. "Long-Term Increases in Neurotransmitter Release from Neuronal Cells Expressing a Constitutively Active Adenylate Cyclase from a Herpes Simplex Virus Type 1 Vector." *PNAS.* 90.16(199317603-7607.
GenBank Accession No. Q08722.1, Nov. 28, 2012.
Gorman et al. "The Rous Sarcoma Virus Long Terminal Repeat is a Strong Promoter when Introduced into a Variety of Eukaryotic Cells by DNA-Mediated Transfection." *PNAS.* 79.22(1982):6777-6781.
Green et al. "Antigen-Specific Human Monoclonal Antibodies from Mice Engineered with Human Ig Heavy and Light Chain YACs." *Nat. Genet.* 7.1(1994):13-21.
Grosschedl et al. "Cell-Type Specificity of Immunoglobulin Gene Expression is Regulated by at Least Three Dna Sequence Elements." *Cell.* 41.3(1985):885-897.
Gruber et al. "Efficient Tumor Cell Lysis Mediated by a Bispecific Single Chain Antibody Express in *Escherichia coli.*" *J. Immunol.* 152.11(1994):5368-5374.
Hanes et al. "In vitro Selection and Evolution of Functional Proteins by Using Ribosome Display." *PNAS.* 94.10(1997):4937-4942.
Hatherley et al. "Paired Receptor Specificity Explained by Structures of Signal Regulatory Proteins Alone and Complexed with CD47." *Mol. Cell.* 31.2(2008):266-277.
Hogenboom et al. "Building Antibodies from their Genes." *Immunol. Rev.* 130(1992):43-68.
Holliger et al. "'Diabodies': Small Bivalent and Bispecific Antibody Fragments." *PNAS.* 90.14(1993):6444-6448.
Houghten et al. "The Use of Synthetic Peptide Combinatorial Libraries for the Identification of Bioactive Peptides." *Biotechniques.* 13.3(1992):412-421.
Houghten. "General Method for the Rapid Solid-Phase Synthesis of Large Numbers of Peptides: Specificity of Antigen-Antibody Interaction at the Level of Individual Amino Acids." *PNAS.* 82.15(1985):5131-5135.
Huse et al. "Generation of a Large Combinatorial Library of the Immunoglobulin Repertoire in Phage Lambda." *Science.* 246. 4935(1989):1275-1281.
Hwang et al. "Hepatic Uptake and Degradation of Unilamellar Sphingomyelin/Cholesterol Liposomes: A Kinetic Study." *PNAS.* 77.7(1980):4030-4034.
Idusogie et al. "Engineered Antibodies with Increased Activity to Recruit Complement." *J. Immunol.* 166.4(2001):2571-2575.
Irandoust et al. "Engagement of SIRPα Inhibits Growth and Induces a Programmed Cell Death in Acute Myeloid Leukemia Cells." *PLoS One.* 8.1(2013):e52143.
Isenberg et al. "Thrombospondin-1 and CD47 Limit Cell and Tissue Survival of Radiation Injury." *Am. J. Pathol.* 173.4(2008):1100-1112.
Jaiswal et al. "CD47 is Upregulated on Circulating Hematopoietic Stem Cells and Leukemia Cells to Avoid Phagocytosis." *Cell.* 138. 2(2009):271-285.
Jansen et al. "Immunotoxins: Hybrid Molecules Combining High Specificity and Potent Cytotoxicity." *Immunological Rev.* 62.1(1982):185-216.
Kabat et al. Sequences of Proteins of Immunological Interest, 5th edit. NIH Publication No. 91-3242 U.S. Dept of Health & Human Services (1991): iii-xcvi, 2130-2180.
Kaneko et al. "Optimizing Therapeutic Antibody Function: Progress with Fc Domain Engineering." *BioDrugs.* 25.1(2011):1-11.
Kaplitt et al. "Long-Term Gene Expression and Phenotypic Correction Using Adeno-Associated Virus Vectors in the Mammalian Brain." *Nat. Genet.* 8.2(1994):148-154.
Kikuchi et al. "A Bivalent Single-Chain Fv Fragment Against CD47 Induces Apoptosis for Leukemic Cells." *Biochem. Biophys. Res. Commun.* 315.4(2004):912-918.
Killen et al. "Specific Killing of Lymphocytes that Cause Experimental Autoimmune Myasthenia Gravis by Ricin Toxin-Acetylcholine Receptor Conjugates." *J. Immunol.* 133.5(1984):2549-2553.
Kilpatrick et al. "Rapid Development of Affinity Matured Monoclonal Anitbodies Using RIMMS." *Hybridoma.* 16.4(1997):381-389.

(56) References Cited

OTHER PUBLICATIONS

Kostelny et al. "Formation of a Bispecific Antibody by the Use of Leucine Zippers." *J. Immunol.* 148.5(1992):1547-1553.
Kozbor et al. "A Human Hybrid Myeloma for Production of Human Monoclonal Antibodies." *J. Immunol.* 133.6(1984):3001-3005.
Kozbor et al. "The Production of Monoclonal Antibodies from Human Lymphocytes." *Immunol. Today.* 4.3(1983):72-79.
Köhler et al. "Continuous Cultures of Fused Cells Secreting Antibody of Predefined Specificity." *Nature.* 256.5517(1975):495-497.
Lam et al. "A New Type of Synthetic Peptide Library for Identifying Ligand-Binding Activity." *Nature.* 354.6348(1991):82-84.
Lam. "Application of Combinatorial Library Methods in Cancer Research and Drug Discovery." *Anticancer Drug Des.* 12.3(1997):145-167.
LaPlanche et al. "Phosphorothioate-Modified Oligodeoxyribonucleotides." *Nucleic Acids Res.* 14.22(1986):9081-9093.
Lazar et al. "Engineered Antibody Fc Variants with Enhanced Effector Function." *PNAS.* 103.11(2006):4005-4010.
Le Gal La Salle et al. "An Adenovirus Vector for Gene Transfer into Neurons and Glia in the Brain." *Science.* 259.5097(1993):988-990.
Liu et al. "Chimeric Mouse-Human IgG1 Antibody That can Mediate Lysis of Cancer Cells." *PNAS.* 84.10(1987):3439-3443.
Liu et al. "Production of a Mouse-Human Chimeric Monoclonal Antibody to CD20 with Potent Fc-Dependent Biologic Activity." *J. Immunol.* 139.10(1987):3521-3526.
Majeti. "Monoclonal Antibody Therapy Directed Against Human Acute Myeloid Leukemia Stem Cells." *Oncogene.* 30.9(2011):1009-1019.
Malmqvist. "Biospecific Interaction Analysis Using Biosensor Technology." *Nature.* 361.6408(1993):186-187.
Marasco et al. "Design, Intracellular Expression, and Activity of Human Anti-Human Immunodeficiency Virus Type 1 gp120 Single-Chain Antibody." *PNAS.* 90.16(1993):7889-7893.
Marasco. "Intrabodies: Turning the Humoral Immune System Outside in for Intracellular Immunization." *Gene Ther.* 4.1(1997):11-15.
Martin et al. "Irreversible Coupling of Immunoglobulin Fragments to Preformed Vesicles." *J. Biol. Chem.* 257.1(1982):286-288.
Maxhimer et al. "Radioprotection in Normal Tissue and Delayed Tumor Growth by Blockade of CD47 Signaling." *Sci. Transl. Med.* 1.3(2009):3ra7.
Milstein et al. "Hybrid Hybridomas and Their Use in Immunohistochemistry." *Nature.* 305.5934(1983):537-540.
Miyashita et al. "Promotion of Neurite and Filopodium Formation by CD47: Roles of Integrins, Rac, and Cdc42." *Mol. Biol. Cell.* 15.8(2004):3950-3963.
Moore et al. "Engineered Fc Variant Antibodies with Enhanced Abiliy to Recruit Complement and Mediate Effector Functions." *MAbs.* 2.2(2010):181-189.
Morrison et al. "High-Flow Microinfusion: Tissue Penetration and Pharmacodynamics." *Am. J. Physiol.* 266.1Pt2(1994):R292-R305.
Morrison. "Success in Specification." *Nature.* 368.6474(1994):812-813.
Munson et al. "Ligand: A Versatile Computerized Approach for Characterization of Ligand-Binding Systems." *Anal. Biochem.* 107.1(1980):220-239.
Natsume et al. "Engineered Antibodies of IgG1/IgG3 Mixed Isotype with Enhanced Cytotoxic Activities." *Cancer Res.* 68.10(2008):3863-3872.
Needleman et al. "A General Method Applicable to the Search for Similarities in the Amino Acid Sequence of Two Proteins." *J. Mol. Biol.* 48.3(1970):443-453.
Okayama et al. "A cDNA Cloning Vector That Permits Expression of cDNA Inserts in Mammalian Cells." *Mol. Cell. Biol.* 3.2(1983):280-289.
Oldenborg et al. "CD47-Signal Regulatory Protein α (SIRPα) Regulates FCγ and Complement Receptor-Mediated Phagocytosis." *J. Exp. Med.* 193.7(2001):855-861.
Oldenborg et al. "Role of CD47 as a Marker of Self on Red Blood Cells." *Science.* 288.5473(2000):2051-2054.
Parmley et al. "Antibody-Selectable Filamentous fd Phage Vectors: Affinity Purification of Target Genes." *Gene.* 73.2(1988):305-318.
Pearson et al. "Improved Tools for Biological Sequence Comparison." *PNAS.* 85.8(1988):2444-2448.
Pinilla et al. "Rapid Identification of High Affinity Peptide Ligands Using Positional Scanning Synthetic Peptide Combinatorial Libraries." *BioTechniques.* 13.6(1992):901-905.
Powell et al. "Compendium of Excipients for Parenteral Formulations." *PDA J. Pharm. Sci. Technol.* 52(1998):238-311.
Ramakrishnan et al. "Comparison of the Selective Cytotoxic Effects of Immunotoxins Containing Ricin A Chain or Pokeweed Antiviral Protein and Anti-Thy 1.1 Monoclonal Antibodies." *Cancer Res.* 44.1(1984):201-208.
Rizo et al. "Constrained Peptides: Models of Bioactive Peptides and Protein Substructures." *Annu. Rev. Biochem.* 61(1992):387-418.
Russell et al. "Retroviral Vectors Displaying Functional Antibody Fragments." *Nucl. Acids Res.* 21.5(1993):1081-1085.
Sarfati et al. "CD47 in the Immune Response: Role of Thrombospondin and SIRP-α Reverse Signaling." *Curr. Drug Targets.* 9.10(2008):842-850.
Scott et al. "Searching for Peptide Ligands with an Epitope Library." *Science.* 249.4967(1990):386-390.
Scott. "Discovering Peptide Ligands Using Epitope Libraries." *Trends Biochem. Sci.* 17.7(1992):241-245.
Shalaby et al. "Development of Humanized Bispecific Antibodies Reactive with Cytotoxic Lymphocytes and Tumor Cells Overexpressing the HER2 Protooncogene." *J. Exp. Med.* 175.1(1992):217-225.
Shields et al. "High Resolution Mapping of the Binding Site on Human IgG1 for FcγRI, FcγRII, FcγRIII, and FcRn and Design of IgG1 Variants with Improved Binding to the FcγR." *J. Biol. Chem.* 276.9(2001):6591-6604.
Shopes. "A Genetically Engineered Human IgG Mutant with Enhanced Cytolytic Activity." *J. Immunol.* 148.9(1992):2918-2922.
Smith et al. "Comparison of Biosequences." *Adv. Appl. Math.* 2.4(1981):482-489.
Soto-Pantoja et al. "Therapeutic Opportunities for Targeting the Ubiquitous Cell Surface Receptor CD47." *Expert. Opin. Ther. Targets.* 17.1(2013):89-103.
Stavenhagen et al. "Enhancing the Potency of Therapeutic Monoclonal Antibodies via Fc Optimization." *Adv. Enzyme Regul.* 48(2008):152-164.
Stavenhagen et al. "Fc Optimization of Therapeutic Antibodies Enhances Their Ability to Kill Tumor Cells In vitro and Controls Tumor Expansion In vivo via Low-Affinity Activating Fcγ Receptors." *Cancer Res.* 67.18(2007):8882-8890.
Stec et al. "Automated Solid-Phase Synthesis, Separation, and Stereochemistry of Phosphorothioate Analogues of Oligodeoxyribonucleotides." *J. Am. Chem. Soc.* 106.20(1984):6077-6079.
Stein et al. "Physicochemical Properties of Phosphorothioate Oligodeoxynucleotides." *Nucl. Acids Res.* 16.8(1988):3209-3221.
Stevenson et al. "A Chimeric Antibody with Dual Fc Region (bisFabFc) Prepared by Manipulations at the IgG Hinge." *Anticancer Drug Des.* 3.4(1989):219-230.
Suresh et al. "Bispecific Monoclonal Antibodies from Hybrid Hybridomas." *Methods Enzymol.* 121(1986):210-228.
Theocharides et al. "Disruption of SIRPα Signaling in Macrophages Elimintes Human Acute Myeloid Leukemia Stem Cells in Xenografts." *J. Exp. Med.* 209.10(2012):1883-1899.
Thornton etal. "Prediction of Progress at Last." *Nature.* 354.6349(1991):105-106.
Traunecker et al. "Bispecific Single Chain Molecules (Janusins) Target Cytotoxic Lymphocytes on HIV Infected Cells." *EMBO J.* 10.12(1991):3655-3659.
Traunecker et al. "Janusin: New Molecular Design for Bispecific Reagents." *Int. J. Cancer.* S7(1992):51-52.
Tutt et al. "Trispecific F(ab')3 Derivatives that Use Cooperative Signaling via the TCR/CD3 Complex and CD2 to Activate and Redirect Resting Cytotoxic T Cells." *J. Immunol.* 147.1(1991):60-69.
Uhlmann et al. "Antisense Oligonucleotides: A New Therapeutic Principle." *Chem. Rev.* 90.4(1990):543-584.

(56) References Cited

OTHER PUBLICATIONS

Uluçkan et al. "CD47 Regulates Bone Mass and Tumor Metastasis to Bone." *Cancer Res.* 69.7(2009):3196-3204.
Uno et al. "Antitumor Activity of a Monoclonal Antibody Against CD47 in Xenograft Models of Human Leukemia." *Oncol. Rep.* 17.5(2007):1189-1194.
Veber et al. "The Design of Metabolically-Stable Peptide Analogs." *Trends Neurosci.* 8(1985):392-396.
Vitetta et al. "Immunotoxins: Magic Bullets or Misguided Missiles?" *Immunol. Today.* 14.6(1993):252-259.
Vitetta et al. "Redesigning Nature's Poisons to Create Anti-Tumor Reagents." *Science.* 238.4830(1987):1098-1104.
Wang. "Lyophilization and Development of Solid Protein Pharmaceuticals." *Int. J. Pharm.* 203.1-2(2000):1-60.
Wilkinson. "Immunochemical Techniques Inspire Development of New Antibody Purification Methods." *The Scientist.* 14.8(2000):25-28.
Winter et al. "Humanized Antibodies." *Immunol. Today.* 14.6(1993):243-246.
Wright et al. "Genetically Engineered Antibodies: Progress and Prospects." *Crit. Rev. Immunol.* 12.3-4(1992):125-168.
Yamauchi et al. "Polymorphic *Sirpa* is the Genetic Determinant for NOD-Based Mouse Lines to Achieve Efficient Human Cell Engraftment." *Blood.* 121.8(2013):1316-1325.
Yang et al. "Cellular and Humoral Immune Responses to Viral Antigens Create Barriers to Lung-Directed Gene Therapy with Recombinant Adenoviruses." *J. Virol.* 69.4(1995):2004-2015.
Zalevsky et al. "Enhanced Antibody Half-Life Improves in vivo Activity." *Nat. Biotechnol.* 28.2(2010):157-159.
Zon et al. "Phosphorothioate Oligonucleotides." *Oligonucleotides and Analogues: A Practical Approach.* Eckstein, ed. Oxford, England: Oxford University Press. (1991):87-108.
Zon et al. "Phosphorothioate Oligonucleotides: Chemistry, Purification, Analysis, Scale-Up and Future Directions." *Anticancer Drug Des.* 6.6(1991):539-568.
Zuckermann et al. "Discovery of Nanomolar Ligands for 7-Transmembrane G-Protein-Coupled Receptors from a Diverse N-(Substituted)glycine Peptoid Library." *J. Med. Chem.* 37.17(1994):2678-2685.
"C37263, Ig Heavy Chain V Region (7D4)." *NCBI.* Jul. 23, 1999. Web. Jul. 11, 2013. http.//www.ncbi.nlm.nih.gov/protein/C37263.
"UniProt_G4EMT6, Inorganic Pyrophosphatase." *UniProt.* Web. Jul. 11, 2013. www.uniprot.com/uniprot/G3EMT6.
Brinkhous et al. "Fixation Platelets and Platelet Agglutination/Aggregation Tests." *Methods Enzymol.* 169(1989):149-163.
De Oliveira et al. "Integrin-Associated Protein (CD47) is a Putative Mediator for Soluble Fibrinogen Interaction with Human Red Blood Cells Membrane." *Biochim. Biophys. Acta.* 1818.3(2012):481-490.
Stavnezer et al. "Evolution of Isotype Switching." *Semin. Immunol.* 16.4(2004):257-275.
Majeti, R. et al. (Jul. 23, 2009). "CD47 is an Adverse Prognostic Factor and Therapeutic Antibody Target on Human Acute Myeloid Leukemia Stem Cells," *Cell* 138(2):286-299.
Subramanian, S. et al. (2006, e-pub. Nov. 10, 2006). "Phylogenetic Divergence in Human SIRPα-CD47 Interactions Reveals Locus of Species-specificity: Implications for the Binding Site," *Journal of Biological Chemistry*, pp. 1-25.
International Search Report mailed on Jul. 1, 2013 for PCT Patent Application No. PCT/US13/24995 filed on Feb. 6, 2013, six pages.
Written Opinion mailed on Jul. 1, 2013 for PCT Patent Application No. PCT/US13/24995 filed on Feb. 6, 2013, ten pages.
International Search Report mailed on Mar. 11, 2014 for PCT Patent Application No. PCT/US2013/053818 filed on Aug. 6, 2013, five pages.
Written Opinion mailed on Mar. 11, 2014 for PCT Patent Application No. PCT/US2013/053818 filed on Aug. 6, 2013, nine pages.

\* cited by examiner

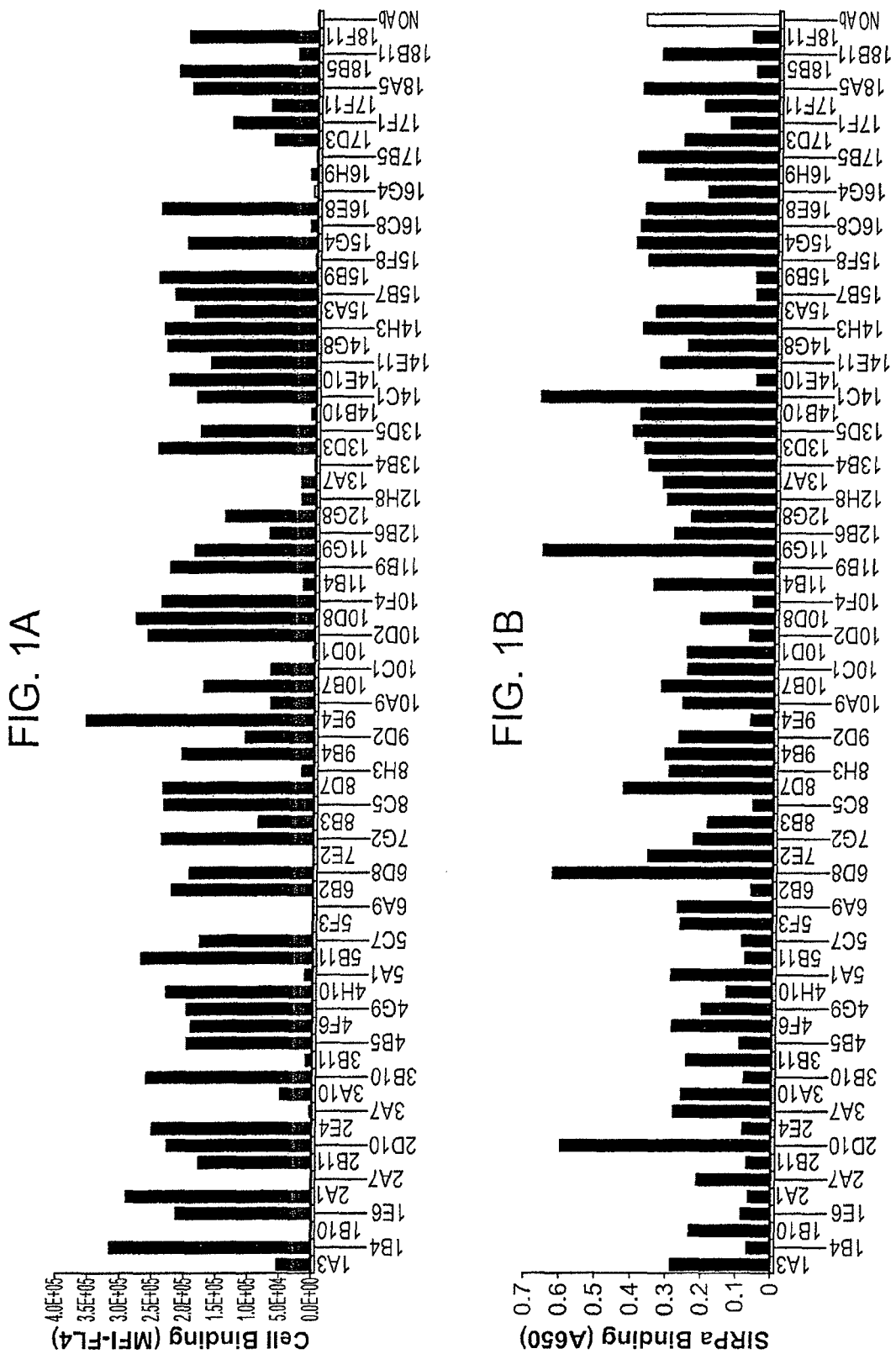

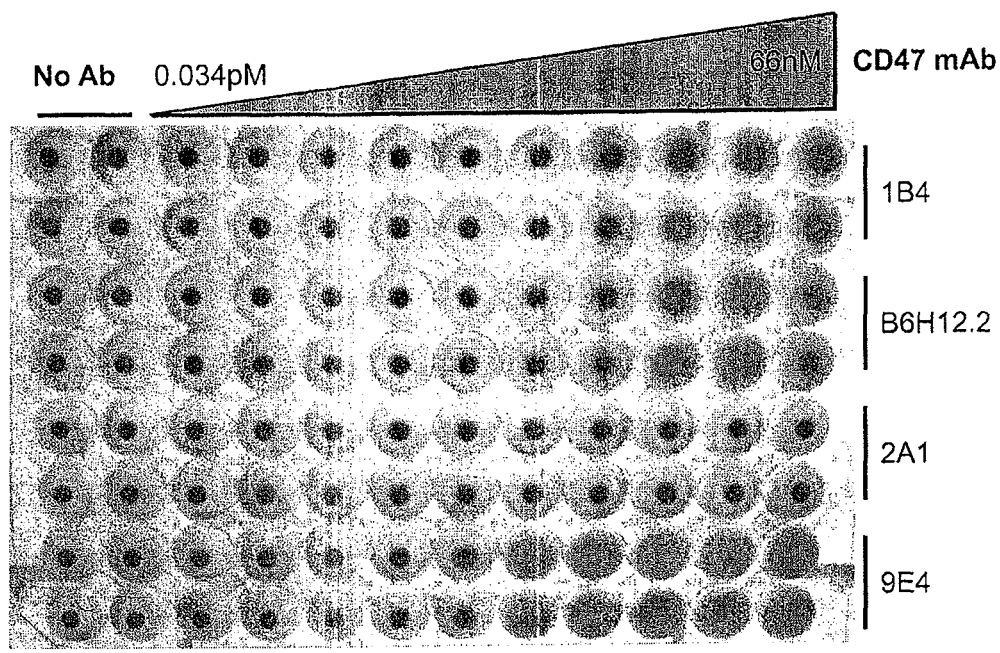
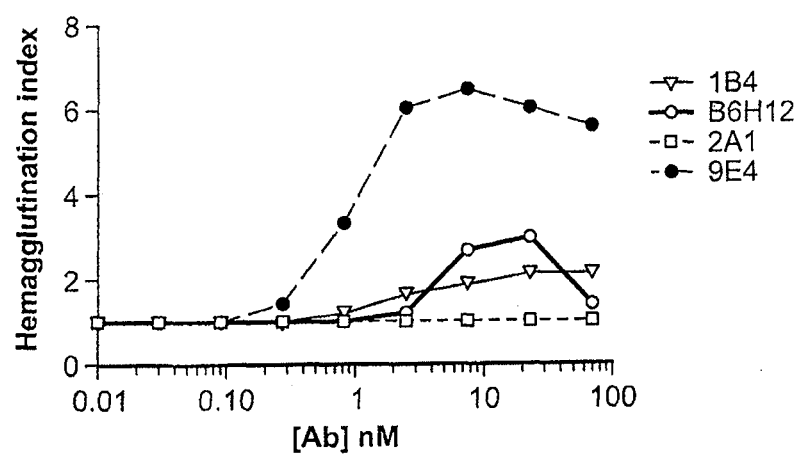
FIG. 4A

| [Ab] (nM) | 100 | 50 | 25 | 12.5 | 100 | 50 | 25 | 12.5 | 100 | 50 | 25 | 12.5 |
|---|---|---|---|---|---|---|---|---|---|---|---|---|
| A | 9E4 | 9E4 | 9E4 | 9E4 | 11B9 | 11B9 | 11B9 | 11B9 | 15B9 | 15B9 | 15B9 | 15B9 |
| B | Blank | Blank | Blank | Blank | 10F4 | 10F4 | 10F4 | 10F4 | 18F11 | 18F11 | 18F11 | 18F11 |
| C | B6H12 | B6H12 | B6H12 | B6H12 | Blank | Blank | Blank | Blank | 18B5 | 18B5 | 18B5 | 18B5 |
| D | 2A1 | 2A1 | 2A1 | 2A1 | 3B10 | 3B10 | 3B10 | 3B10 | 17F11 | 17F11 | 17F11 | 17F11 |
| E | 2A1-XI | 2A1-XI | 2A1-XI | 2A1-XI | 15B7 | 15B7 | 15B7 | 15B7 | Blank | Blank | Blank | Blank |
| F | 6B2 | 6B2 | 6B2 | 6B2 | 2B11 | 2B11 | 2B11 | 2B11 | Blank | Blank | Blank | Blank |
| G | 14E10 | 14E10 | 14E10 | 14E10 | 5B11 | 5B11 | 5B11 | 5B11 | Blank | Blank | Blank | Blank |
| H | Blank | Blank | Blank | Blank | Blank | Blank | Blank | Blank | Blank | Blank | Blank | Blank |
|  | 1 | 2 | 3 | 4 | 5 | 6 | 7 | 8 | 9 | 10 | 11 | 12 |

2A1→
2A1-xi→

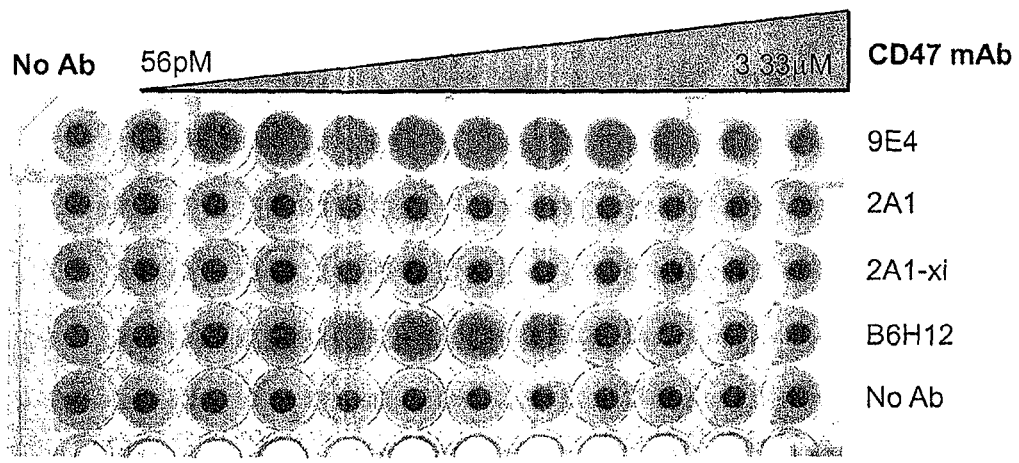
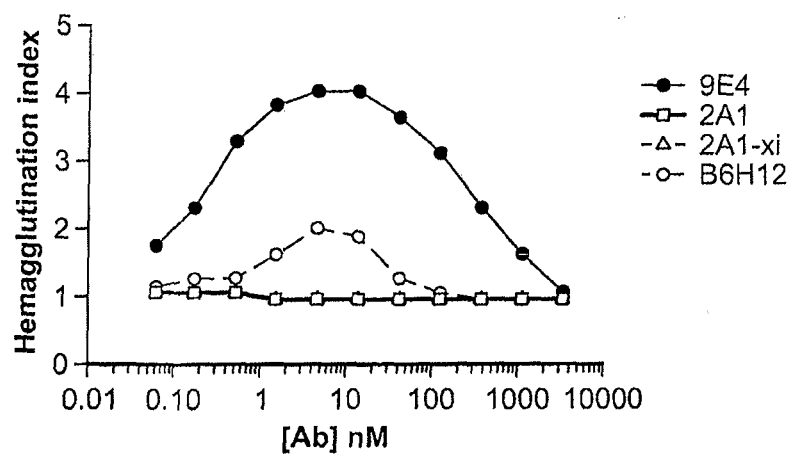
FIG. 4D

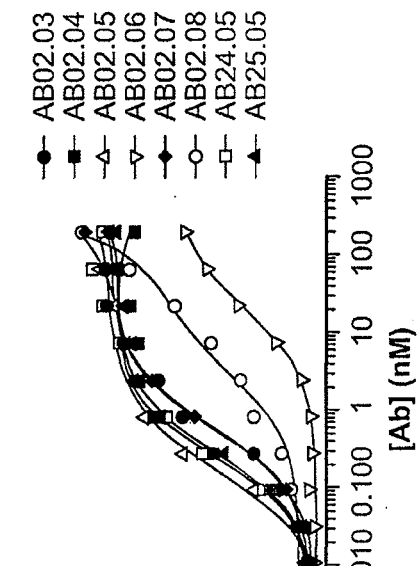
FIG. 7A
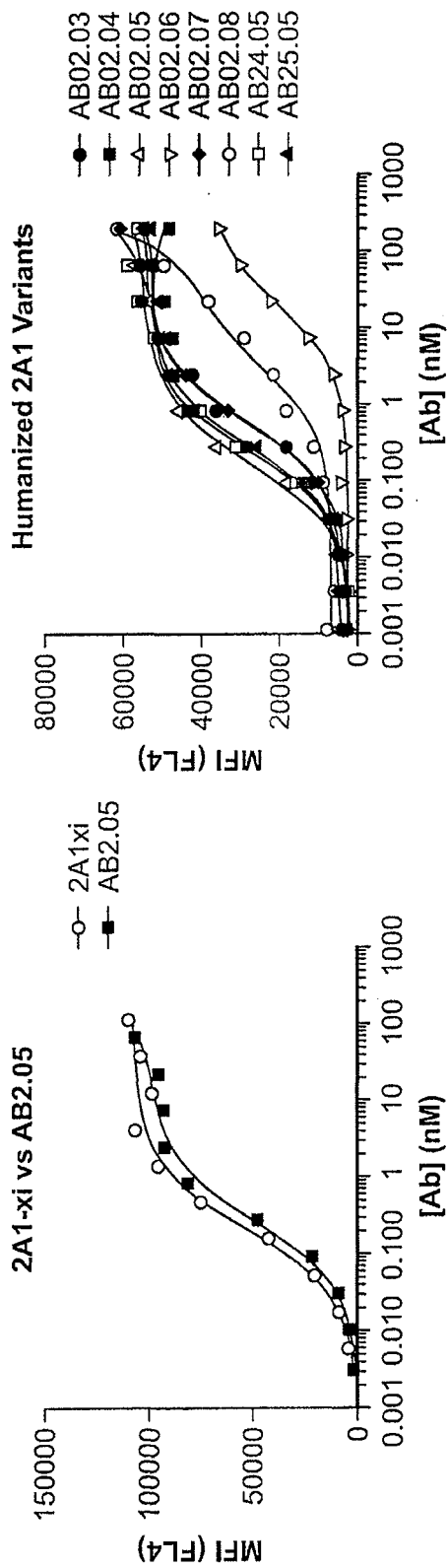
FIG. 7B
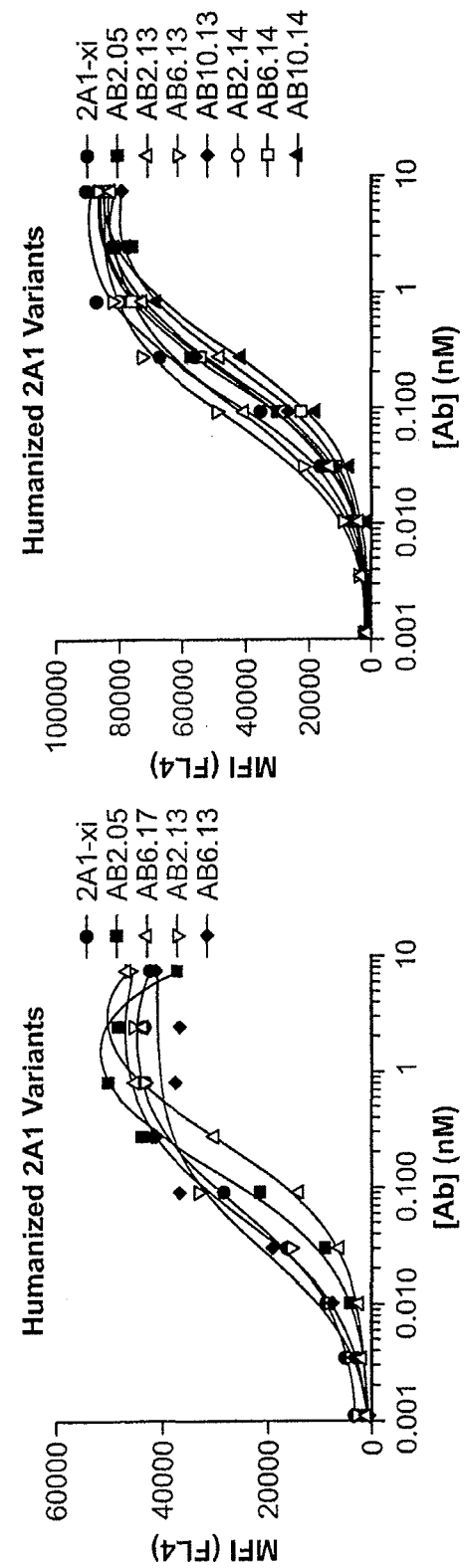
FIG. 7C
FIG. 7D

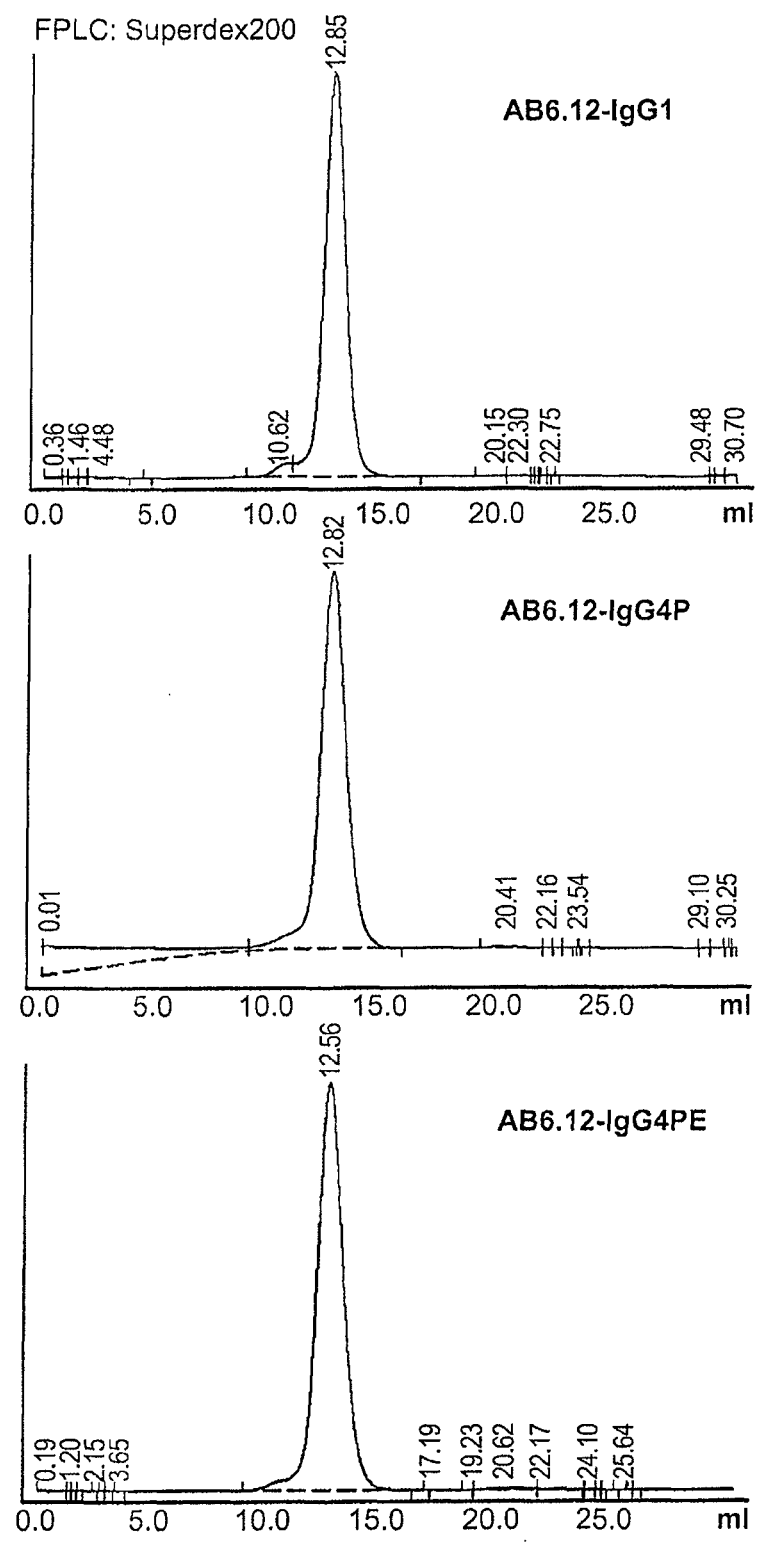

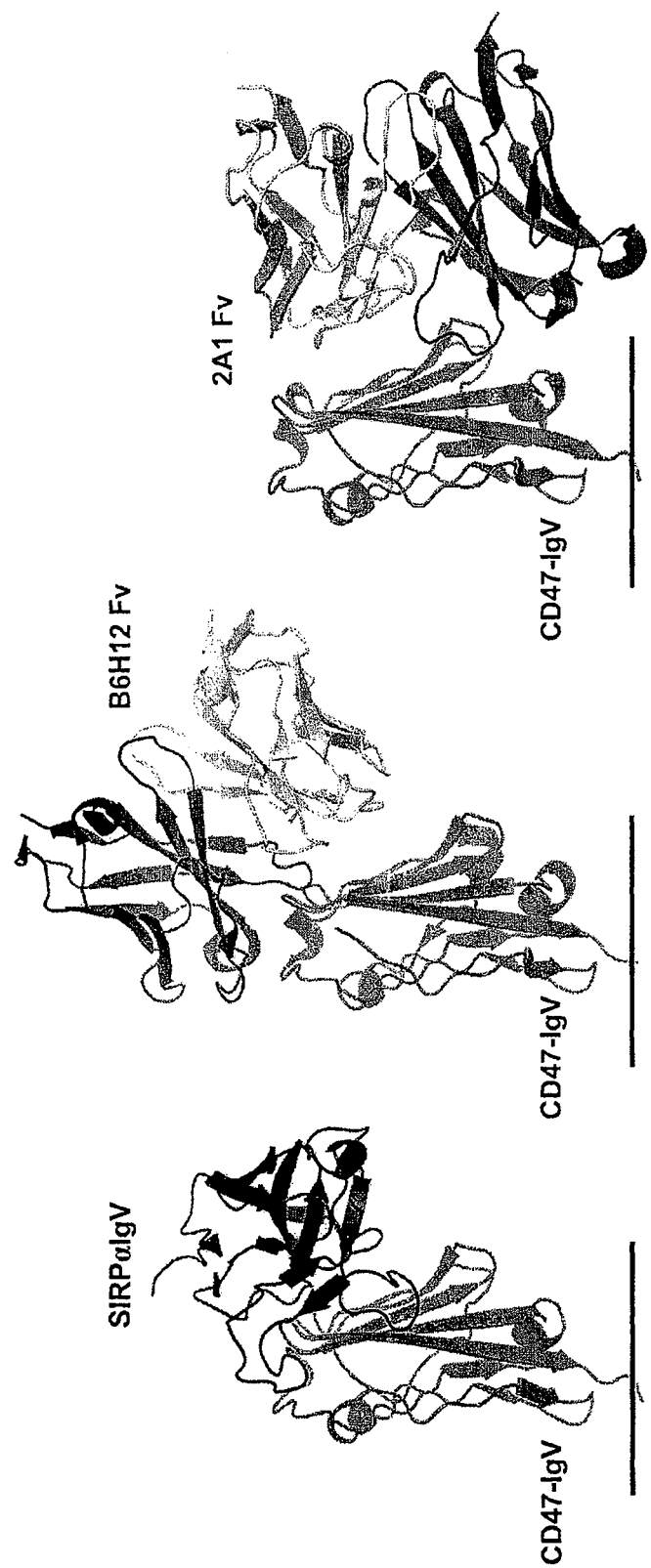

US 9,045,541 B2

CD47 ANTIBODIES AND METHODS OF USE THEREOF

RELATED APPLICATIONS

This application claims the benefit of priority under 35 U.S.C. §119(e) to U.S. Provisional Application No. 61/595,216, filed Feb. 6, 2012 and to U.S. Provisional Application No. 61/659,752, filed Jun. 14, 2012. Each of these applications is incorporated herein by reference in its entirety.

INCORPORATION-BY-REFERENCE OF SEQUENCE LISTING

The contents of the text file named "42967-506001US ST25.txt", which was created on May 3, 2013 and is 90 KB in size, is hereby incorporated by reference in their entirety.

FIELD OF THE INVENTION

This invention relates generally to monoclonal antibodies that recognize CD47, more specifically to CD47 antibodies that do not cause a significant level of hemagglutination of human red blood cells, to methods of generating these antibodies, and to methods of using these monoclonal antibodies as therapeutics.

BACKGROUND OF THE INVENTION

CD47, also known as integrin-associated protein (IAP), ovarian cancer antigen OA3, Rh-related antigen and MER6, is a multi-spanning transmembrane receptor belonging to the immunoglobulin superfamily. CD47 expression and/or activity have been implicated in a number of diseases and disorders. Accordingly, there exists a need for therapies that target CD47.

SUMMARY OF THE INVENTION

The present invention provides monoclonal antibodies that recognize and bind to CD47, particularly human CD47. The antibodies of the invention are capable of modulating, e.g., blocking, inhibiting, reducing, antagonizing, neutralizing or otherwise interfering with CD47 expression, activity and/or signaling, and these antibodies do not cause a significant level of hemagglutination of human red blood cells, also referred to herein as erythrocytes. However, the ability of the antibodies of the present invention to bind CD47 on the cell surface and not cause a cellular clumping phenomenon is not limited to red blood cells. The antibodies of the present invention uniquely bind CD47 in a manner that does not promote clumping of CD47 positive cells. The antibodies of the invention and derivatives thereof are capable of modulating, e.g., blocking, inhibiting, reducing, antagonizing, neutralizing or otherwise interfering with the interaction between CD47 and SIRPα (signal-regulatory-protein α), and these antibodies do not cause a significant level of hemagglutination of human red blood cells. The antibodies provided herein are referred to collectively as "CD47 antibodies." The CD47 antibodies of the invention are a significant improvement over existing CD47 antibodies that cause hemagglutination of human red blood cells (See, e.g., Kikuchi Y, Uno S, Yoshimura Y et al. A bivalent single-chain Fv fragment against CD47 induces apoptosis for leukemic cells. Biochem Biophys Res Commun 2004; 315: 912-8). For example, the CD47 antibodies of the invention are a significant improvement over the existing CD47 antibodies B6H12, BRC126, and CC2C6, each of which block SIRPα, but cause hemagglutination of RBCs, as described in detail below. The full IgG CD47 antibodies of the present invention (e.g., 2A1 and its humanized derivatives including those provided in Table 1) do not agglutinate cells at a significant level. For example, the CD47 antibodies of the invention do not hemagglutinate red blood cells (RBCs). Described herein are the first CD47 antibodies in a full IgG format that block SIRPα and do not cause a significant level of agglutination.

The CD47 antibodies of the invention exhibit numerous desirable characteristics, such as, by way of non-limiting example, potent blocking of the interaction between CD47 and its ligand SIRPα, without causing a significant level of hemagglutination of erythrocytes, as well as potent anti-tumor activity. For example, the CD47 antibodies of the invention block at least 40%, at least 45%, at least 50%, at least 55%, at least 60%, at least 65%, at least 70%, at least 75%, at least 80%, at least 85%, at least 95%, or at least 99% of the interaction between CD47 and SIRPα as compared to the level of interaction between CD47 and SIRPα in the absence of the CD47 antibody described herein.

The CD47 antibodies of the invention do not cause a significant level of agglutination of cells, e.g., the CD47 antibodies of the invention do not cause a significant level of hemagglutination of red blood cells. In some cases, a significant level of agglutination of cells refers to the level of agglutination in the presence of existing CD47 antibodies. In one aspect, the level of agglutination in the presence of the CD47 antibodies of the invention is reduced by at least 5%, at least 10%, at least 20%, at least 30%, at least 40%, at least 50%, at least 60%, at least 70%, at least 80%, at least 90%, or at least 99% compared to the level of agglutination in the presence existing CD47 antibodies. In some embodiments, the CD47 antibodies of the invention do not cause a significant level of agglutination if the level of agglutination in the presence of the CD47 antibodies of the invention is reduced by at least 5%, at least 10%, at least 20%, at least 30%, at least 40%, at least 50%, at least 60%, at least 70%, at least 80%, at least 90%, or at least 99% compared to the level of agglutination in the presence of existing CD47 antibodies. In other embodiments, the CD47 antibodies of the invention do not cause a significant level of agglutination if the level of agglutination in the presence of the CD47 antibodies of the invention is reduced by at least 5%, at least 10%, at least 20%, at least 30%, at least 40%, at least 50%, at least 60%, at least 70%, at least 80%, at least 90%, or at least 99% compared to the level of agglutination in the presence of CD47 antibody, 1B4, which comprises a variable heavy and variable light chain sequence provided in SEQ ID NO: 80 and SEQ ID NO: 81, respectively. Preferably, the CD47 antibodies of the invention do not cause a significant level of agglutination of cells at an antibody concentration of between 10 pM and 10 µM, e.g., at an antibody concentration of 50 pM, 100 pM, 1 nM, 10 nM, 50 nM, 100 nM, 1 µM, or 5 µM.

The antibodies of the present invention are also significantly more potent in tumor models compared to antibodies known in the art. For example, the ability of macrophages to phagocytose tumor cells in the presence of CD47 antibodies of the invention is increased by at least 5%, at least 10%, at least 20%, at least 30%, at least 40%, at least 50%, at least 60%, at least 70%, at least 80%, at least 90%, or at least 99% compared to the ability of macrophages to phagocytose tumor cells in the presence of existing CD47 antibodies.

Those skilled in the art will recognize that it is possible to quantitate, without undue experimentation, the level of agglutination, e.g., the level of hemagglutination of RBCs. For example, those skilled in the art will recognize that the level of hemagglutination is ascertained by measuring the area of an RBC dot after performing a hemagglutination assay in the presence of the CD47 antibodies of the invention, as described in the Examples below. In some cases, the area of the RBC dot in the presence of the CD47 antibody of the invention is compared to the area of the RBC dot in the absence of a CD47 antibody, i.e., in the presence of zero hemagglutination. In this manner, hemagglutination is quantified relative to a baseline control. A larger RBC dot area corresponds to a higher level of hemagglutination. Alternatively, densitometry of the RBC dot may also be utilized to quantitate hemagglutination.

The CD47 antibodies described herein are useful in treating, delaying the progression of, preventing relapse of or alleviating a symptom of a cancer or other neoplastic condition. For example, the CD47 antibodies described herein are useful in treating hematological malignancies and/or tumors, e.g., hematological malignancies and/or tumors. For example, the CD47 antibodies described herein are useful in treating CD47+ tumors. By way of non-limiting example, the CD47 antibodies described herein are useful in treating non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and so on. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

As used herein, "hematological cancer" refers to a cancer of the blood, and includes leukemia, lymphoma and myeloma among others. "Leukemia" refers to a cancer of the blood in which too many white blood cells that are ineffective in fighting infection are made, thus crowding out the other parts that make up the blood, such as platelets and red blood cells. It is understood that cases of leukemia are classified as acute or chronic. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

Exemplary monoclonal antibodies of the invention include, for example, the antibodies described herein. Exemplary antibodies include antibodies having a variable heavy chain selected from SEQ ID NOs: 5-30 and a variable light chain selected from SEQ ID NOs: 31-47. The antibodies also include antibodies having a variable heavy chain that is at least 90%, 91%, 92%, 93%, 94%, 95%, 96%, 97%, 98%, 99% or more identical to the sequence set forth in at least one of SEQ ID NOs: 5-30 and a variable light chain that is at least 90%, 91%, 92%, 93%, 94%, 95%, 96%, 97%, 98%, 99% or more identical to the sequence set forth in at least one of SEQ ID NOs: 31-47. Preferably, the antibodies recognize and bind to human CD47 and do not cause a significant level of hemagglutination of human red blood cells. These antibodies are respectively referred to herein as CD47 antibodies. CD47 antibodies include fully human monoclonal antibodies, as well as humanized monoclonal antibodies and chimeric antibodies. These antibodies show specificity for human CD47, and they have been shown to modulate, e.g., block, inhibit, reduce, antagonize, neutralize or otherwise interfere with CD47 expression, activity and/or signaling without causing a significant level of hemagglutination of red blood cells.

The CD47 antibodies provided herein exhibit inhibitory activity, for example by inhibiting CD47 expression (e.g., inhibiting cell surface expression of CD47), activity, and/or signaling, or by interfering with the interaction between CD47 and SIRPα. The antibodies provided herein completely or partially reduce or otherwise modulate CD47 expression or activity upon binding to, or otherwise interacting with, CD47, e.g., a human CD47. The reduction or modulation of a biological function of CD47 is complete, significant, or partial upon interaction between the antibodies and the human CD47 polypeptide and/or peptide. The antibodies are considered to completely inhibit CD47 expression or activity when the level of CD47 expression or activity in the presence of the antibody is decreased by at least 95%, e.g., by 96%, 97%, 98%, 99% or 100% as compared to the level of CD47 expression or activity in the absence of interaction, e.g., binding, with the antibody described herein. The CD47 antibodies are considered to significantly inhibit CD47 expression or activity when the level of CD47 expression or activity in the presence of the CD47 antibody is decreased by at least 50%, e.g., 55%, 60%, 75%, 80%, 85% or 90% as compared to the level of CD47 expression or activity in the absence of binding with a CD47 antibody described herein. The antibodies are considered to partially inhibit CD47 expression or activity when the level of CD47 expression or activity in the presence of the antibody is decreased by less than 95%, e.g., 10%, 20%, 25%, 30%, 40%, 50%, 60%, 75%, 80%, 85% or 90% as compared to the level of CD47 expression or activity in the absence of interaction, e.g., binding, with an antibody described herein.

Antibodies of the invention also include monoclonal antibodies that specifically bind CD47, wherein the antibody does not cause a significant level of agglutination, e.g., red blood cell hemagglutination ("RBC hemagglutination"). The antibodies of the present invention uniquely bind CD47 in a manner that does not promote clumping of CD47 positive cells; however, the ability of the antibodies of the present invention to bind CD47 on the cell surface and not cause a cellular clumping phenomenon is not limited to red blood cells.

Pharmaceutical compositions according to the invention can include an antibody of the invention and a carrier. These pharmaceutical compositions can be included in kits, such as, for example, diagnostic kits.

The invention provides monoclonal antibodies that bind to CD47 or an immunologically active fragment thereof, wherein the antibody does not cause a significant level of agglutination of cells after administration, e.g., the antibody does not cause a significant level of hemagglutination of red blood cells after administration. In some embodiments, the antibody is chimeric, humanized, or fully human. In some embodiments, the antibodies bind to human CD47. In some embodiments, the antibody or immunologically active fragment thereof prevents CD47 from interacting with SIRPα. The antibodies are considered to completely inhibit the interaction of CD47 and SIRPα when the level of CD47/SIRPα interaction in the presence of the antibody is decreased by at least 95%, e.g., by 96%, 97%, 98%, 99% or 100% as compared to the level of CD47/SIRPα interaction in the absence of interaction with the antibody, e.g., binding with the antibody. The antibodies are considered to partially inhibit CD47/SIRPα interaction when the level of CD47/SIRPα interaction in the presence of the antibody is decreased by less than 95%, e.g., 10%, 20%, 25%, 30%, 40%, 50%, 60%, 75%, 80%, 85% or 90% as compared to the level of CD47/SIRPα interaction in the absence of interaction with the antibody, e.g., binding with the antibody.

The amount of antibody sufficient to treat or prevent cancer in the subject is, for example, an amount that is sufficient to reduce CD47 signaling (See, e.g., Yamauchi et al., 2013 Blood, Jan. 4. [Epub ahead of print]; Soto-Pantoja et al., 2013 Expert Opin Ther Targets, 17: 89-103; Irandoust et al., 2013 PLoS One, Epub January 8; Chao et al., 2012 Curr Opin Immunol, 24:225-32; Theocharides et al., 2012 J Exp Med, 209(10): 1883-99; Csányi et al., 2012 Arterioscler Thromb Vasc Biol, 32: 2966-73; Maxhimer et al., 2009 Sci Transl Med, 1: 3ra7; Sarfati et al., 2008 Curr Drug Targets, 9: 842-850; Miyashita et al., 2004 Mol Biol Cell, 15: 3950-3963; E. J. Brown and W. A. Frazier, 2001 Trends Cell Biol, 11: 130-135; Oldenborg et al., 2001 J Exp Med, 193: 855-862; Blazar et al., 2001 J Exp Med, 194: 541-549; Oldenborg et al., 2000 Science, 288: 2051-2054; and Gao et al., 1996 J Biol Chem, 271: 21-24). For example, the amount of antibody sufficient to treat or prevent cancer in the subject is an amount that is sufficient to reduce the phagocytic inhibitory signal in macrophages generated by CD47/SIRPα interaction in the CD47/SIRPα signaling axis, i.e., the antibody of the invention promotes macrophage-mediated phagocytosis of a CD47-expressing cell. As used herein, the term "reduced" refers to a decreased CD47 signaling in the presence of the antibody of the invention. CD47 mediated signaling is decreased when the level of CD47 signaling in the presence of a CD47 antibody of the invention is greater than or equal to 5%, 10%, 20%, 25%, 30%, 40%, 50%, 60%, 70%, 75%, 80%, 90%, 95%, 99%, or 100% lower than a control level of CD47 signaling (i.e., the level of CD47 signaling in the absence of the antibody). Level of CD47 signaling is measured using any of a variety of standard techniques, such as, by way of non-limiting example, measurement of down-stream gene activation, and/or luciferase reporter assays responsive to CD47 activation. Those skilled in the art will appreciate that the level of CD47 signaling can be measured using a variety of assays, including, for example, commercially available kits.

In some embodiments, the antibody or immunologically active fragment thereof is an IgG isotype. In some embodiments, the constant region of the antibody is of human IgG1 isotype, having an amino acid sequence:

```
                                                        (SEQ ID NO: 1)
ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCP PCPAPELLGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK
```

In some embodiments, the human IgG1 constant region is modified at amino acid Asn297 (Boxed, Kabat Numbering) to prevent to glycosylation of the antibody, for example Asn297Ala (N297A). In some embodiments, the constant region of the antibody is modified at amino acid Leu235 (Kabat Numbering) to alter Fc receptor interactions, for example Leu235Glu (L235E) or Leu235Ala (L235A). In some embodiments, the constant region of the antibody is modified at amino acid Leu234 (Kabat Numbering) to alter Fc receptor interactions, e.g., Leu234Ala (L234A). In some embodiments, the constant region of the antibody is altered at both amino acid 234 and 235, for example Leu234Ala and Leu235Ala (L234A/L235A) (EU index of Kabat et al 1991 *Sequences of Proteins of Immunological Interest*).

In some embodiments, the constant region of the antibody is of human IgG2 isotype, having an amino acid sequence:

```
                                                        (SEQ ID NO: 2)
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APPVAGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK
```

In some embodiments, the human IgG2 constant region is modified at amino acid Asn297 (Boxed, Kabat Numbering) to prevent to glycosylation of the antibody, e.g., Asn297Ala (N297A).

In some embodiments, the constant region of the antibody is of human IgG3 isotype, having an amino acid sequence:

```
                                                    (SEQ ID NO: 3)
ASTKGPSVFP LAPCSRSTSG GTAALGCLVK DYFPEPVTVS WNSGALTSGV

HTFPAVLQSS GLYSLSSVVT VPSSSLGTQT YTCNVNHKPS NTKVDKRVEL

KTPLGDTTHT CPRCPEPKSC DTPPPCPRCP EPKSCDTPPP CPRCPEPKSC

DTPPPCPRCP APELLGGPSV FLFPPKPKDT LMISRTPEVT CVVVDVSHED

PEVQFKWYVD GVEVHNAKTK PREEQY[N]STF RVVSVLTVLH QDWLNGKEYK

CKVSNKALPA PIEKTISKTK GQPREPQVYT LPPSREEMTK NQVSLTCLVK

GFYPSDIAVE WESSGQPENN YNTTPPMLDS DGSFFLYSKL TVDKSRWQQG

NIFSCSVMHE ALHN[R]FTQKS LSLSPGK
```

In some embodiments, the human IgG3 constant region is modified at amino acid Asn297 (Boxed, Kabat Numbering) to prevent to glycosylation of the antibody, e.g., Asn297Ala (N297A). In some embodiments, the human IgG3 constant region is modified at amino acid 435 to extend the half-life, e.g., Arg435H is (R435H) (EU index of Kabat et al 1991 *Sequences of Proteins of Immunological Interest*).

In some embodiments, the constant region of the antibody is of human IgG4 isotype, having an amino acid sequence:

```
                                                    (SEQ ID NO: 4)
ASTKGPSVFP LAPCSRSTSE STAALGCLVK DYFPEPVTVS WNSGALTSGV

HTFPAVLQSS GLYSLSSVVT VPSSSLGTKT YTCNVDHKPS NTKVDKRVES

KYGPPCP[S]CP APEF[L]GGPSV FLFPPKPKDT LMISRTPEVT CVVVDVSQED

PEVQFNWYVD GVEVHNAKTK PREEQF[N]STY RVVSVLTVLH QDWLNGKEYK

CKVSNKGLPS SIEKTISKAK GQPREPQVYT LPPSQEEMTK NQVSLTCLVK

GFYPSDIAVE WESNGQPENN YKTTPPVLDS DGSFFLYSRL TVDKSRWQEG

NVFSCSVMHE ALHNHYTQKS LSLSLGK
```

In some embodiments, the human IgG4 constant region is modified within the hinge region to prevent or reduce strand exchange, e.g., Ser228Pro (S228P). In other embodiments, the human IgG4 constant region is modified at amino acid 235 to alter Fc receptor interactions, e.g., Leu235Glu (L235E). In some embodiments, the human IgG4 constant region is modified within the hinge and at amino acid 235, e.g., Ser228Pro and Leu235Glu (S228P/L235E). In some embodiments, the human IgG4 constant region is modified at amino acid Asn297 (Kabat Numbering) to prevent to glycosylation of the antibody, e.g., Asn297Ala (N297A). (EU index of Kabat et al 1991 *Sequences of Proteins of Immunological Interest*).

In some embodiments, the human IgG constant region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J. Biol Chem Vol* 281(33) 23514-23524), or Met428Leu and Asn434Ser (M428L, N434S) (Zalevsky et al 2010 *Nature Biotech*, Vol 28(2) 157-159). (EU index of Kabat et al 1991 *Sequences of Proteins of Immunological Interest*). In some embodiments, the human IgG constant region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11.

In some embodiments, the human IgG constant region is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15).

The invention also provides pharmaceutical compositions that include one or more monoclonal antibodies that bind to CD47 or an immunologically active fragment thereof, wherein the antibody does not cause a significant level of hemagglutination of red blood cells after administration.

Hemagglutination is an example of a homotypic interaction, wherein two CD47 expressing cells are caused to aggregate or clump when treated with a bivalent CD47 binding entity. The ability of the antibodies of the present invention to bind CD47 on the cell surface and not cause a cellular clumping phenomenon is not limited to red blood cells. The antibodies of the present invention have been observed to uniquely bind CD47 in a manner that does not promote clumping of CD47 positive cell lines, e.g., Daudi cells.

In some cases, the antibody comprises a variable heavy (VH) chain region selected from the group consisting of SEQ ID NOs: 5-30. The antibody optionally comprises a variable light (VL) chain region selected from the group consisting of SEQ ID NOs: 31-47. In some cases, the antibody comprises a VH chain region selected from the group consisting of SEQ ID NOs: 5-30 and a VL chain region selected from the group consisting of SEQ ID NOs: 31-47. The antibodies of the invention also include antibodies having a variable heavy chain that is at least 90%, 91%, 92%, 93%, 94%, 95%, 96%, 97%, 98%, 99% or more identical to the sequence set forth in at least one of SEQ ID NOs: 5-30 and a variable light chain that is at least 90%, 91%, 92%, 93%, 94%, 95%, 96%, 97%, 98%, 99% or more identical to the sequence set forth in at least one of SEQ ID NOs: 31-47. In other aspects, the antibody comprises a VH region provided in any one of SEQ ID NOs: 5, 7, 8, 11, 15-17, 20-22, and 27-30 paired with a VL region provided in any one of SEQ ID NOs: 31-39, 42, 43, 44, and 47. In another embodiment, the antibody comprises a VH region provided in any one of SEQ ID NOs: 5, 7, 8, 11, 12, 15-17, 20-22, and 27-30 paired with a VL region provided in any one of SEQ ID NOs: 31, 32, 35, 40, 41, 42, 43, 44, and 47. In yet another aspect, the antibody comprises a combination of a VH chain region and a VL chain region selected from the combinations listed in Table 1.

In some embodiments, the CD47 antibody or immunologically active fragment thereof comprises a VH complementarity determining region 1 (CDR1) sequence set forth in SEQ ID NO: 50, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 66, a VH CDR2 sequence set forth in SEQ ID NO: 51, SEQ ID NO: 72, SEQ ID NO: 73, SEQ ID NO: 74, SEQ ID NO: 75, or SEQ ID NO: 76, a VH CDR3 sequence set forth in SEQ ID NO: 52 or SEQ ID NO: 77, a VL CDR1 sequence set forth in SEQ ID NO: 53, SEQ ID NO: 67, or SEQ ID NO: 68, a VL CDR2 sequence set forth in SEQ ID NO: 54, SEQ ID NO: 69, SEQ ID NO: 70, or SEQ ID NO: 71 and a VL CDR3 sequence set forth in SEQ ID NO: 55. For example, the antibody or immunologically active fragment thereof comprises a VH CDR1 sequence set forth in SEQ ID NO: 50, a VH CDR2 sequence set forth in SEQ ID NO: 51, a VH CDR3 sequence set forth in SEQ ID NO: 52, a VL CDR1 sequence set forth in SEQ ID NO: 53, a VL CDR2 sequence set forth in SEQ ID NO: 54, and a VL CDR3 sequence set forth in SEQ ID NO: 55. In another example, the antibody or immunologically active fragment thereof comprises a VH CDR1 sequence set forth in SEQ ID NO: 50, a VH CDR2 sequence set forth in SEQ ID NO: 72, a VH CDR3 sequence set forth in SEQ ID NO: 52, a VL CDR1 set forth in SEQ ID NO: 53, a VL CDR2 sequence set forth in SEQ ID NO: 71, and a VL CDR3 sequence set forth in SEQ ID NO: 55.

In one embodiment, the antibodies of the present invention bind to CD47 in a head to side orientation that positions the heavy chain near the membrane of CD47 expressing cell, while the light chain occludes the SIRPα binding site on CD47. In another embodiment, the antibodies of the present invention bind to CD47 in a head to side orientation that positions the light chain near the membrane of CD47 expressing cell, while the heavy chain occludes the SIRPα binding site on CD47.

The CD47 antibodies bind to an epitope that includes any one of amino acid residues 1-116 of CD47 when numbered in accordance with SEQ ID NO: 147 (i.e., SEQ ID NO: 48 excluding the signal sequence (amino acids 1-18)). For example, the antibodies of the present invention bind to an epitope that includes one or more of amino acid residues Q31, N32, T33, T34, E35, V36, Y37, V38, K39, W40, K41, F42, K43, G44, R45, D46, I47, Y48, T49, F50, D51, G52, A53, L54, N55, K56, S57, T58, V59, P60, T61, D62, F63, S64, S65, A66, K67, I68, E69, V70, S71, Q72, L73, L74, K75, G76, D77, A78, S79, L80, K81, M82, D83, K84, S85, D86, A87, V88, S89, H90, T91, G92, N93, Y94, T95, C96, E97, V98, T99, E100, L101, T102, R103, E104, G105, E106, T107, I108, I109, and E110 of CD47 when numbered in accordance with SEQ ID NO: 147.

In some cases, the antibodies of the present invention bind to a discontinuous epitope that includes one or more of amino acid residues Y37, V38, K39, W40, K41, F42, K43, G44, R45, D46, I47, Y48, T49, F50, and D51 of CD47 when numbered in accordance with SEQ ID NO: 147. For example, the antibodies of the present invention bind to a discontinuous epitope comprising amino acids residues Y37, K39, K41, K43, G44, R45, D46, D51, H90, N93, E97, T99, E104, or E106 of CD47 when numbered in accordance with SEQ ID NO: 147. For example, the antibodies of the present invention bind to a discontinuous epitope that includes at least residues of the KGRD (SEQ ID NO: 56) loop (residues 43-46) of CD47 when numbered in accordance with SEQ ID NO: 147. For example, the antibodies of the present invention bind to a discontinuous epitope that includes at least residues Y37, K39, K41, the KGRD (SEQ ID NO: 56) loop (residues 43-46), D51, H90, N93, E97, T99, E104, and E106 of CD47 when numbered in accordance with SEQ ID NO: 147. For example, the antibodies of the present invention bind to a discontinuous epitope that includes residues Y37, K39, K41, the KGRD (SEQ ID NO: 56) loop (residues 43-46), D51, H90, N93, E97, T99, E104, and E106 of CD47 when numbered in accordance with SEQ ID NO: 147.

The VH region of the CD47 antibodies described herein is primarily involved in binding to the KGRD (SEQ ID NO: 56) loop of CD47. Thus, the unique epitope to which antibodies of the present invention bind is on the side of CD47. In contrast to existing CD47 antibodies known in the art, the orientation of the VH domain of the CD47 antibodies described herein in a membrane proximal position is a critical feature of these antibodies that prevents cellular clumping, e.g., red blood cell hemagglutination, by constraining the antibodies such that they cannot bridge to CD47 molecules on adjacent cells. Additionally, because the VK domain of the CD47 antibodies described herein interacts with apical residues such as Y37, T102, and E104, which are involved in SIRPα binding, it is primarily the VK domain that physically precludes SIRPα binding to CD47.

Also provided is an isolated antibody or an immunologically active fragment thereof which competes with the CD47 antibodies described herein for preventing CD47 from interacting with SIRPα.

The invention provides a polypeptide comprising amino acids residues Y37, K39, K41, K43, G44, R45, D46, D51, H90, N93, E97, T99, E104, and E106 of CD47 when numbered in accordance with SEQ ID NO: 147. Also provided is a polypeptide comprising any one of amino acid residues 1-116 of CD47 when numbered in accordance with SEQ ID NO: 147. For example, the polypeptide comprises one or more of amino acid residues Q31, N32, T33, T34, E35, V36, Y37, V38, K39, W40, K41, F42, K43, G44, R45, D46, I47, Y48, T49, F50, D51, G52, A53, L54, N55, K56, S57, T58, V59, P60, T61, D62, F63, S64, S65, A66, K67, I68, E69, V70, S71, Q72, L73, L74, K75, G76, D77, A78, S79, L80, K81, M82, D83, K84, S85, D86, A87, V88, S89, H90, T91, G92, N93, Y94, T95, C96, E97, V98, T99, E100, L101, T102, R103, E104, G105, E106, T107, I108, I109, and E110 of CD47 when numbered in accordance with SEQ ID NO: 147. Also provided are methods of using this polypeptide as an antigen, e.g., an antigen which binds a CD47 antibody.

The invention also provides methods of alleviating a symptom of a cancer or other neoplastic condition by administering to a subject in need thereof one or more monoclonal antibodies that bind to CD47 or an immunologically active fragment thereof, wherein the antibody does not cause a significant level of hemagglutination of red blood cells after administration. The antibody is administered in an amount sufficient to alleviate the symptom of the cancer or other neoplastic condition in the subject. In some embodiments, the subject is a human. In some embodiments, the antibody is chimeric, humanized, or fully human. In some embodiments, the antibody binds to human CD47. In some embodiments, the antibody or immunologically active fragment thereof prevents CD47 from interacting with SIRPα. In some embodiments, the antibody or immunologically active fragment thereof is an IgG isotype selected from the group consisting of IgG1 isotype, IgG2 isotype, IgG3 isotype, and IgG4 isotype. In some embodiments, the antibody or immunologically active fragment thereof is an IgG isotype selected from IgG4P and IgGPE.

In some embodiments, the CD47 antibodies described herein are used in conjunction with one or more additional agents or a combination of additional agents. Suitable additional agents include current pharmaceutical and/or surgical therapies for an intended application, such as, for example, cancer. For example, the CD47 antibodies can be used in conjunction with one or more additional chemotherapeutic or anti-neoplastic agents. Alternatively, the additional chemotherapeutic agent is radiotherapy. In some embodiments, the chemotherapeutic agent is a cell death-inducing agent. In some embodiments, the chemotherapeutic agent induces a loss of phospholipid asymmetry across the plasma membrane, for example causes cell surface exposure of phosphatidylserine (PS). In some embodiments, the chemotherapeutic agent induces endoplasmic reticulum (ER) stress. In some embodiments, the chemotherapeutic agent is a proteasome inhibitor. In some embodiments, the chemotherapeutic agent induces the translocation of ER proteins to the cell surface. In some embodiments, the chemotherapeutic agent induces the translocation and cell surface exposure of calreticulin.

In some embodiments, the CD47 antibody and additional agent are formulated into a single therapeutic composition, and the CD47 antibody and additional agent are administered simultaneously. Alternatively, the CD47 antibody and additional agent are separate from each other, e.g., each is formulated into a separate therapeutic composition, and the CD47 antibody and the additional agent are administered simultaneously, or the CD47 antibody and the additional agent are administered at different times during a treatment regimen. For example, the CD47 antibody is administered prior to the administration of the additional agent, the CD47 antibody is administered subsequent to the administration of the additional agent, or the CD47 antibody and the additional agent are administered in an alternating fashion. As described herein, the CD47 antibody and additional agent are administered in single doses or in multiple doses.

One skilled in the art will appreciate that the antibodies of the invention have a variety of uses. For example, the antibodies of the invention are used as therapeutic agents, as reagents in diagnostic kits or as diagnostic tools, or as reagents in competition assays to generate therapeutic reagents.

BRIEF DESCRIPTION OF THE DRAWINGS

FIG. 1A is a graph depicting the binding of CD47 on Daudi cells by antibodies in hybridoma supernatants as assessed by flow cytometry. FIG. 1B is a graph showing the ability of some of the CD47 antibodies within the hybridoma supernatant to block the binding of recombinant human SIRPα to recombinant human CD47, as determined by an ELISA.

FIG. 4 is a series of photographs, graphs, and a table that show RBC hemagglutination by CD47 antibodies. RBC hemagglutination is evidenced by a haze appearance in the well, whereas non-agglutinated RBC appear as punctate. FIG. 4A shows that the 2A1 antibody displays no hemagglutination at all concentrations tested. Hemagglutination index is depicted in the graph. FIG. 4D shows a high concentration range of the CD47 antibodies in the hemagglutination assay and demonstrates the pro-zone effect. Hemagglutination index is depicted in the graph.

FIG. 7A-7J is a series of graphs showing binding of humanized variants of 2A1 to Raji cells. 2A1-xi was used as an internal control on most graphs. Numerous combinations of heavy and light chains were tested as described in Example 8.

FIG. 8A is image of the trace from size exclusion chromatography using an AKTA FLPC with a superdex200 column. Shown are the IgG1, IgG4P, and IgGPE variants of the AB6.12 antibody. All three variant are over 97% monomeric.

FIG. 9 is a series of graphs depicting the ability of CD47 antibodies to promote phagocytosis of human tumor cell lines by human monocyte derived macrophages (MDM).

FIG. 10 is a series of graphs showing the anti-tumor effects of CD47 antibodies in a Raji tumor model.

FIG. 11 is a graphic representation of the co-crystal complexes of CD47-IgV with SIRPα-IgV domain (A, (Protein Data Bank (PDB) Reference No. 2JJS), B6H12 (B), and 2A1 (C). 2A1 and B6H12 bind in very different orientations and distinct epitopes on CD47, both of which overlap with the SIRPα binding site. The 2A1 antibody binds in a head to side orientation on the CD47 protein.

DETAILED DESCRIPTION

Figure 2A:
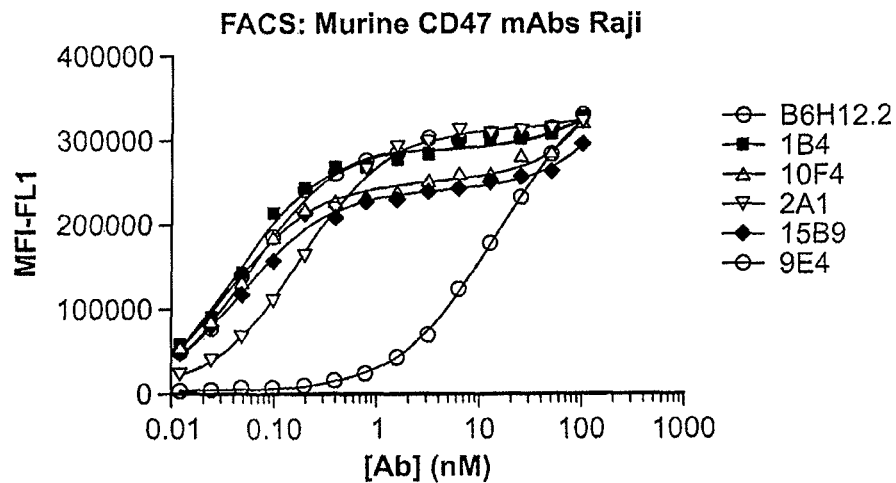
FIG. 2 is a series of graphs depicting (A) the binding of purified murine CD47 antibodies to Raji cells, a cultured line of lymphoblastoid cells derived from a Burkitt lymphoma, and (B) CCRF-CEM cells, a CD47 positive human T cell lymphoblast-like cell line, as analyzed by flow cytometry. This experiment compares the binding of the murine antibodies of the present invention to the commercially available CD47 antibodies, B6H12 and 2D3.

The present invention provides monoclonal antibodies that specifically bind CD47, including human CD47. These antibodies are collectively referred to herein as CD47 antibodies.

CD47, a multi-spanning transmembrane receptor belonging to the immunoglobulin superfamily, interacts with SIRPα (signal-regulatory-protein a) on macrophages and thereby dampens phagocytosis. Cancer cells that co-opt this pathway evade phagocytosis. As described in detail below, this is a new mechanism of tumor immune avoidance, and therapeutically targeting CD47 has widespread application in numerous cancers.

The expression of CD47 correlates with worse clinical outcomes in many distinct malignancies including Non-Hodgkin Lymphoma (NHL), Acute Lymphocytic Leukemia (ALL), Acute Myelogenous Leukemia (AML), ovarian cancer, glioma, glioblastoma, etc. In addition, CD47 has been identified as a cancer stem cell marker in both leukemias and solid tumors (Jaiswal et al., 2009 Cell, 138(2): 271-85; Chan et al., 2009 Proc Natl Acad Sci USA, 106(33): 14016-21; Chan et al., 2010 Curr Opin Urol, 20(5): 393-7; Majeti R et al., 2011 Oncogene, 30(9): 1009-19).

CD47 blocking antibodies have demonstrated anti-tumor activity multiple in vivo tumor models. Furthermore, these antibodies have been shown to synergize with other therapeutic antibodies including Rituxan® and Herceptin® in tumor models. Blocking the interaction of CD47 with SIRPα is capable of promoting phagocytosis of CD47 expressing cells by macrophages (reviewed in Chao et al., 2012 Curr Opin Immunol, 24(2): 225-32). Mice lacking CD47 are markedly resistant to radiation therapy, suggesting a role for targeting CD47 in combination with radiotherapy (Isenberg et al., 2008 Am J Pathol, 173(4): 1100-1112; Maxhimer et al., 2009 Sci Transl Med, 1(3): 3ra7). Furthermore, syngeneic tumor models in these mice display decreased bone metastasis compared wild-type mice (Uluckan et al., 2009 Cancer Res, 69(7): 3196-204).

Importantly, most CD47 antibodies have been reported to cause hemagglutination of human erythrocytes. Hemagglutination is an example of a homotypic interaction, wherein two CD47 expressing cells are caused to aggregate or clump when treated with a bivalent CD47 binding entity. For example, the CD47 antibody, MABL, as a full IgG or F(ab')$_2$, has been reported to cause hemagglutination of erythrocytes, and, only when MABL was altered into an scFv or bivalent scFv, was this effect mitigated. (See e.g., Uno S, Kinoshita Y, Azuma Y et al. Antitumor activity of a monoclonal antibody against CD47 in xenograft models of human leukemia. Oncol Rep 2007; 17: 1189-94; Kikuchi Y, Uno S, Yoshimura Y et al. A bivalent single-chain Fv fragment against CD47 induces apoptosis for leukemic cells. Biochem Biophys Res Commun 2004; 315: 912-8). Other known CD47 antibodies including B6H12, BRC126, and CC2C6 also cause hemagglutination of RBCs, as described in detail below. Thus, the aggregation of cells represents a major limitation of therapeutically targeting CD47 with existing full IgG antibodies.

Moreover, an important characteristic of CD47 antibodies is the ability to block the interaction of CD47 and SIRPα in order to promote the phagocytosis of CD47 expressing cells by macrophages. Many existing CD47 antibodies block SIRPα; however, prior to the invention described herein, existing antibodies that blocked SIRPα caused the side effect of hemagglutination, which, as described above, is undesirable. Other existing antibodies, such as 2D3, do not cause hemagglutination; however, these antibodies also do not block SIRPα, rendering them ineffective in the promotion of phagocytosis. Thus, prior to the invention described herein, there was a pressing need to identify CD47 antibodies that blocked SIRPα without causing cellular clumping.

The CD47 antibodies of the present invention avoid the undesirable effect of hemagglutination, thereby increasing the efficacy of therapeutically targeting CD47, and maintain the ability to block the interaction of CD47 with SIRPα, thereby promoting phagocytosis of CD47 expressing cells. Specifically, the full IgG CD47 antibodies of the present invention (e.g., 2A1 and its humanized derivatives including those provided in Table 1) do not agglutinate cells at a significant level. For example, the CD47 antibodies of the invention do not hemagglutinate RBCs at a significant level. Described herein are the first CD47 antibodies in a full IgG format that block SIRPα and do not cause a significant level of hemagglutination. Taken together, the antibodies of the invention (e.g., the 2A1 antibody and its humanized derivatives) are unique among existing CD47 antibodies in their ability to block SIRPα, but not cause a significant level of hemagglutination.

The CD47 antibodies of the invention exhibit numerous desirable characteristics, such as, by way of non-limiting example, potent blocking of the interaction between CD47 and its ligand SIRPα, without causing a significant level of or otherwise modulating hemagglutination of erythrocytes, as well as potent anti-tumor activity. For example, the CD47 antibodies of the invention block at least 40%, at least 45%, at least 50%, at least 55%, at least 60%, at least 65%, at least 70%, at least 75%, at least 80%, at least 85%, at least 95%, or at least 99% of the interaction between CD47 and SIRPα as compared to the level of interaction between CD47 and SIRPα in the absence of the CD47 antibody described herein. The CD47 antibodies of the invention do not cause a significant level of agglutination of cells, e.g., the CD47 antibodies of the invention do not cause a significant level of hemagglutination of red blood cells. For example, the level of agglutination in the presence of the CD47 antibodies of the invention is reduced by at least 5%, at least 10%, at least 20%, at least 30%, at least 40%, at least 50%, at least 60%, at least 70%, at least 80%, at least 90%, or at least 99% compared to the level of agglutination in the presence existing CD47 antibodies. In some embodiments, the CD47 antibodies of the invention do not cause a significant level of agglutination if the level of agglutination in the presence of the CD47 antibodies of the invention is reduced by at least 5%, at least 10%, at least 20%, at least 30%, at least 40%, at least 50%, at least 60%, at least 70%, at least 80%, at least 90%, or at least 99% compared to the level of agglutination in the presence of CD47 antibody, 1B4, which comprises a variable heavy and variable light chain sequence provided in SEQ ID NO: 80 and SEQ ID NO: 81, respectively. The antibodies of the present invention are also significantly more potent in tumor models compared to antibodies known in the art. For example, the ability of macrophages to phagocytose tumor cells in the presence of CD47 antibodies of the invention is increased by at least 5%, at least 10%, at least 20%, at least 30%, at least 40%, at least 50%, at least 60%, at least 70%, at least 80%, at least 90%, or at least 99% compared to the ability of macrophages to phagocytose tumor cells in the presence of existing CD47 antibodies.

Those skilled in the art will recognize that it is possible to quantitate, without undue experimentation, the level of agglutination, e.g., the level of hemagglutination of RBCs. For example, those skilled in the art will recognize that the level of hemagglutination is ascertained by measuring the area of an RBC dot after performing a hemagglutination assay in the presence of the CD47 antibodies of the invention, as described in the Examples below. In some cases, the area of the RBC dot in the presence of the CD47 antibody of the invention is compared to the area of the RBC dot in the absence of a CD47 antibody, i.e., in the presence of zero hemagglutination. In this manner, hemagglutination is quantified relative to a baseline control. A larger RBC dot area corresponds to a higher level of hemagglutination. Alternatively, densitometry of the RBC dot may also be utilized to quantitate hemagglutination.

Figure 7E:
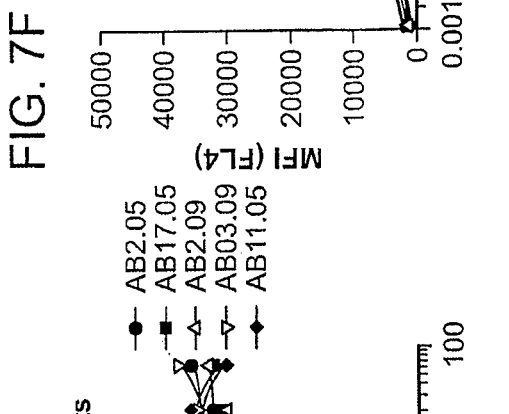
Figure 7F:
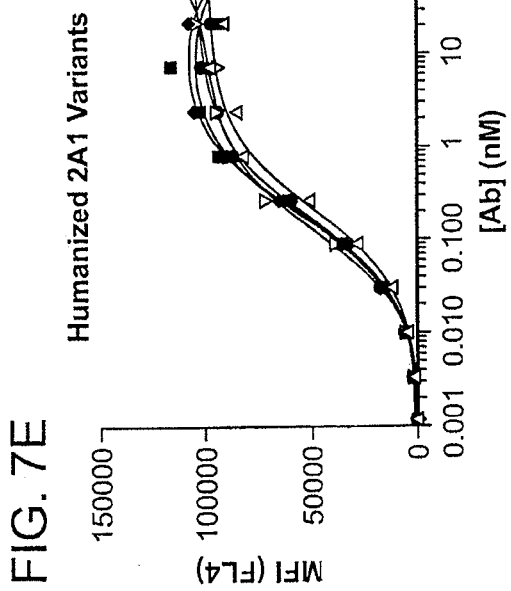
Figure 7G:
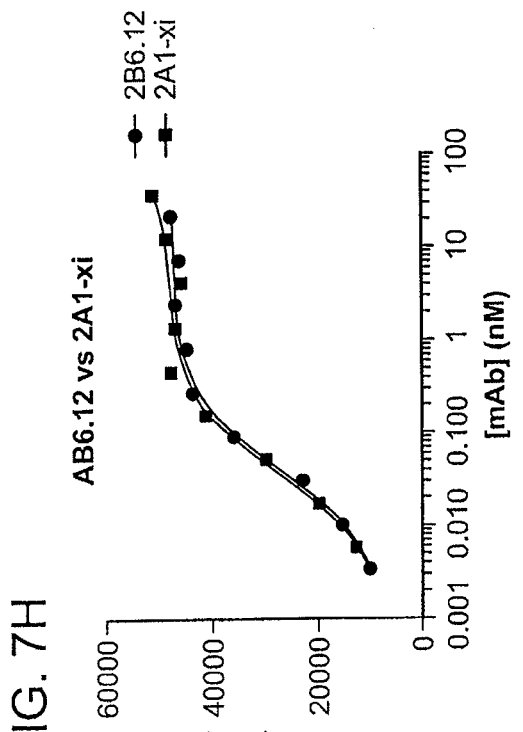
Figure 7H:
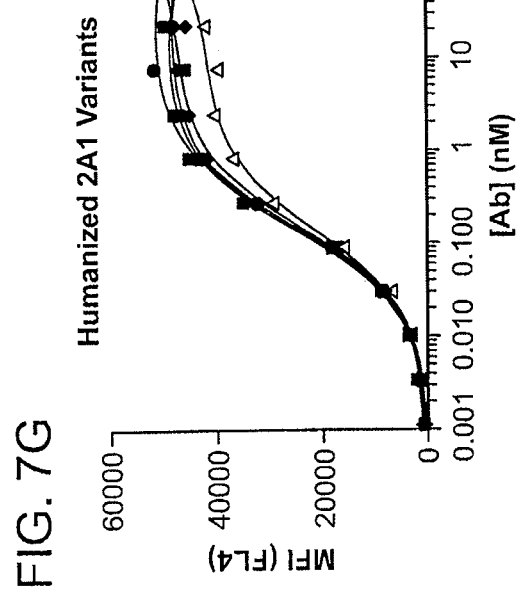
Figure 7I:
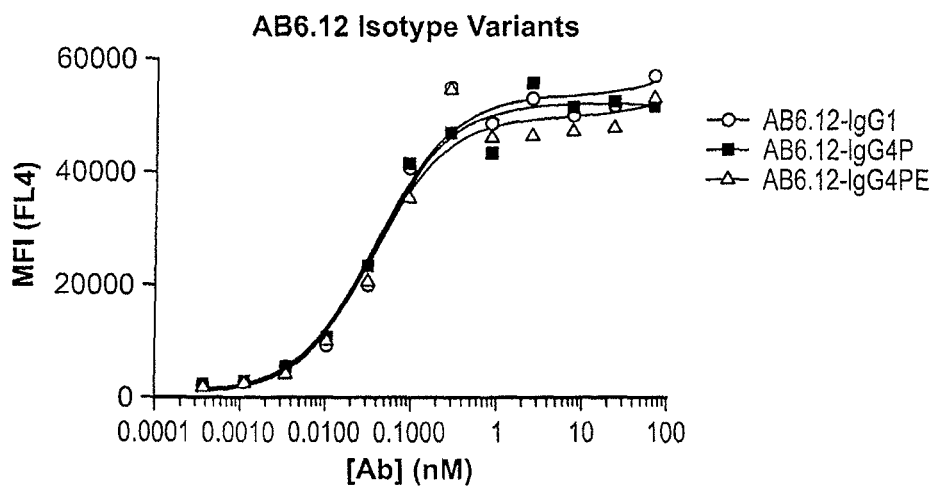
Figure 7J:
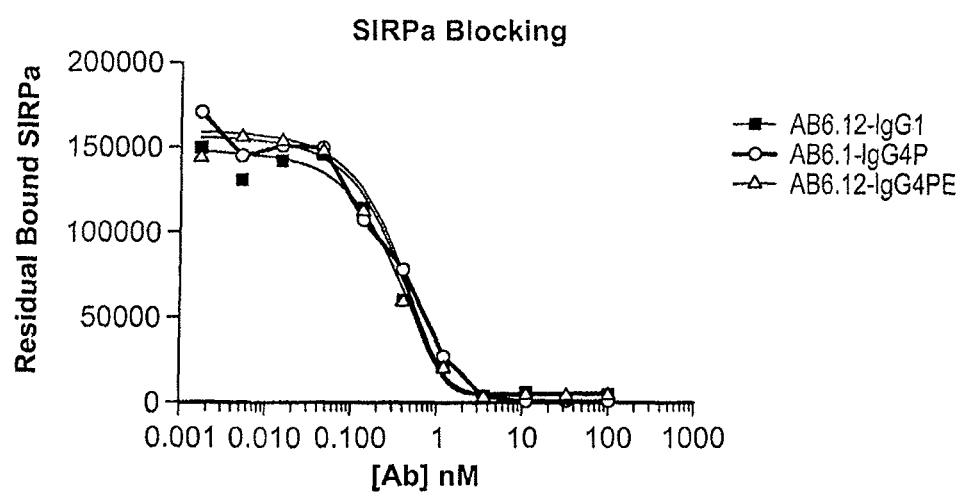

The CD47 antibodies of the invention bind to human CD47 and block its interaction with SIRPα (FIGS. 1B, 3, and 7J). These antibodies do not cause a significant level of hemagglutination of human erythrocytes (FIG. 4). These antibodies are capable of promoting phagocytosis of tumor cells by macrophages (FIG. 9). Furthermore, the CD47 antibodies display potent anti-tumor activity in a mouse model of human lymphoma (FIG. 10). Thus, the CD47 antibodies of the invention circumvent a major limiting factor for the therapeutic targeting CD47. Accordingly, the CD47 antibodies of the invention stand to be of great importance in treatment a multitude of cancers.

Antibodies of the invention that specifically bind human CD47, block, inhibit, disrupt or otherwise modulate the interaction between human CD47 and human SIRPα, without causing a significant level of or otherwise modulating hemagglutination of erythrocytes.

The antibodies of the present invention bind to a CD47 epitope with an equilibrium binding constant ($K_d$) of ≤1 μM, e.g., ≤100 nM, preferably ≤10 nM, and more preferably ≤1 nM. For example, the CD47 antibodies provided herein exhibit a $K_d$ in the range approximately between ≤1 nM to about 1 pM.

The CD47 antibodies of the invention serve to modulate, block, inhibit, reduce, antagonize, neutralize or otherwise interfere with the functional activity of the widely distributed CD47. Functional activities of CD47 include for example, signaling via the interaction with SIRPα, modulating, e.g., increasing, intracellular calcium concentration upon cell adhesion to extracellular matrix, interacting with the C-terminal cell binding domain of thrombospondin, interacting with fibrinogen, and interacting with various integrins. For example, the CD47 antibodies completely or partially inhibit CD47 functional activity by partially or completely modulating, blocking, inhibiting, reducing antagonizing, neutralizing, or otherwise interfering with the binding of CD47 to SIRPα.

The CD47 antibodies are considered to completely modulate, block, inhibit, reduce, antagonize, neutralize or otherwise interfere with CD47 functional activity when the level of CD47 functional activity in the presence of CD47 antibody is decreased by at least 95%, e.g., by 96%, 97%, 98%, 99% or 100% as compared to the level of CD47 functional activity in the absence of binding with a CD47 antibody described herein. The CD47 antibodies are considered to significantly block, inhibit, reduce, antagonize, neutralize or otherwise interfere with CD47 functional activity when the level of CD47 activity in the presence of the CD47 antibody is decreased by at least 50%, e.g., 55%, 60%, 75%, 80%, 85% or 90% as compared to the level of CD47 activity in the absence of binding with a CD47 antibody described herein. The CD47 antibodies are considered to partially modulate, block, inhibit, reduce, antagonize, neutralize or otherwise interfere with CD47 functional activity when the level of CD47 activity in the presence of the CD47 antibody is decreased by less than 95%, e.g., 10%, 20%, 25%, 30%, 40%, 50%, 60%, 75%, 80%, 85% or 90% as compared to the level of CD47 activity in the absence of binding with a CD47 antibody described herein.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms CD47, integrin-associated protein (IAP), ovarian cancer antigen OA3, Rh-related antigen and MERG are synonymous and may be used interchangeably.

The terms red blood cell(s) and erythrocyte(s) are synonymous and used interchangeably herein.

The term agglutination refers to cellular clumping, while the term hemagglutination refers to clumping of a specific subset of cells, i.e., red blood cells. Thus, hemagglutination is a type of agglutination.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, Fab, Fab- and F(ab')$_2$ fragments, F$_v$, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG$_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to CD47, when the equilibrium binding constant ($K_d$) is ≤1 µM, preferably ≤100 nM, more preferably ≤10 nM, and most preferably ≤100 pM to about 1 pM, as measured by assays such as radioligand binding assays, surface plasmon resonance (SPR), flow cytometry binding assay, or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide," as referred to herein, refers to a polymeric boron of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to CD47, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

CD47 Antibodies

Monoclonal antibodies of the invention have the ability to bind CD47, to inhibit the binding of SIRPα to CD47, decrease CD47-SIRPα-mediated signaling, promote phagocytosis, and to inhibit tumor growth and/or migration. Inhibition is determined, for example, using the cellular assay described herein in the Examples.

Exemplary antibodies of the invention include the 2A1 antibody, the chimeric version of 2A1, and humanized variants of 2A1. Exemplary antibodies of the invention include an antibody having a variable heavy (VH) chain selected from SEQ ID NOs: 5-30, and having a variable light (VL) chain selected from SEQ ID NOs: 31-47. Specifically, exemplary antibodies include those provided in Table 1.

TABLE 1

| Antibody | Variable heavy (VH) chain | Variable light (VL) chain |
| --- | --- | --- |
| 2A1 | SEQ ID NO: 5 | SEQ ID NO: 31 |
| 2A1-xi | SEQ ID NO: 5 | SEQ ID NO: 32 |
| AB2.03 | SEQ ID NO: 7 | SEQ ID NO: 33 |
| AB2.04 | SEQ ID NO: 7 | SEQ ID NO: 34 |
| AB2.05 | SEQ ID NO: 7 | SEQ ID NO: 35 |

TABLE 1-continued

| Antibody | Variable heavy (VH) chain | Variable light (VL) chain |
| --- | --- | --- |
| AB2.06 | SEQ ID NO: 7 | SEQ ID NO: 36 |
| AB2.07 | SEQ ID NO: 7 | SEQ ID NO: 37 |
| AB2.08 | SEQ ID NO: 7 | SEQ ID NO: 38 |
| AB2.09 | SEQ ID NO: 7 | SEQ ID NO: 39 |
| AB2.13 | SEQ ID NO: 7 | SEQ ID NO: 43 |
| AB3.09 | SEQ ID NO: 8 | SEQ ID NO: 39 |
| AB6.12 | SEQ ID NO: 11 | SEQ ID NO: 42 |
| AB6.13 | SEQ ID NO: 11 | SEQ ID NO: 43 |
| AB6.14 | SEQ ID NO: 11 | SEQ ID NO: 44 |
| AB6.17 | SEQ ID NO: 11 | SEQ ID NO: 47 |
| AB10.13 | SEQ ID NO: 15 | SEQ ID NO: 43 |
| AB10.14 | SEQ ID NO: 15 | SEQ ID NO: 44 |
| AB11.05 | SEQ ID NO: 16 | SEQ ID NO: 35 |
| AB12.05 | SEQ ID NO: 17 | SEQ ID NO: 35 |
| AB15.05 | SEQ ID NO: 20 | SEQ ID NO: 35 |
| AB16.05 | SEQ ID NO: 21 | SEQ ID NO: 35 |
| AB17.05 | SEQ ID NO: 22 | SEQ ID NO: 35 |
| AB22.05 | SEQ ID NO: 27 | SEQ ID NO: 35 |
| AB23.05 | SEQ ID NO: 28 | SEQ ID NO: 35 |
| AB24.05 | SEQ ID NO: 29 | SEQ ID NO: 35 |
| AB25.05 | SEQ ID NO: 30 | SEQ ID NO: 35 |

Also included in the invention are antibodies that bind to the same epitope as the CD47 antibodies described herein. For example, antibodies of the invention specifically bind to an epitope that includes one or more amino acid residues on human CD47 (see e.g., GenBank Accession No. Q08722.1).

The amino acid sequence of an exemplary human CD47 is provided below (GenBank Accession No. Q08722.1 (GI: 1171879), incorporated herein by reference). The signal sequence (amino acids 1-18) is underlined.

(SEQ ID NO: 48)
```
  1 mwplvaalll qsaccqsaql lfnktksvef tfcndtvvip cfvtnmeaqn ttevyvkwkf 61 kgrdiytfdg alnkstvptd fssakievsq llkgdaslkm dksdayshtg nytcevtelt 121 regetiielk yrvvswfspn enilivifpi faillfwgqf giktlkyrsg gmdektiall 181 vaglvitviv ivgailfvpg eyslknatgl glivtstgil illhyyvfst aigltsfvia 241 ilviqviayi lavvglslci aacipmhgpl lisglsilal aqllglvymk fvasnqktiq 301 pprkaveepl nafkeskgmm nde
```

For clarity, the amino acid sequence of an exemplary human CD47 excluding the signal sequence is provided below.

(SEQ ID NO: 147)
```
  1 qllfnktksv eftfcndtvv ipcfvtnmea qnttevyvkw kfkgrdiytf dgalnkstvp 61 tdfssakiev sqllkgdasl kmdksdaysh tgnytcevte ltregetiie lkyrvvswfs 121 pnenilivif pifaillfwg qfgiktlkyr sggmdektia llvaglvitv ivivgailfv 181 pgeyslknat glglivtstg ilillhyyvf staigltsfv iailviqvia yilavvglsl 241 ciaacipmhg pllisglsil alaqllglvy mkfvasnqkt iqpprkavee pinafkeskg 301 mmnde
```

The amino acid sequence of an exemplary human CD47-IgV domain is provided below:

(SEQ ID NO: 49)
```
 19 qllfnktksv eftfcndtvv ipcfvtnmea qnttevyvkw kfkgrdiytf dgalnkstvp 79 tdfssakiev sqllkgdasl kmdksdaysh tgnytcevte ltregetiie lkyrvv
```

Exemplary monoclonal antibodies of the invention include, for example, humanized antibodies having a variable heavy chain region (VH) and/or variable light (VL) chain region shown in the sequences below.

Variable heavy (VH) chain regions of the CD47 antibodies are provided below. The complementarity determining regions (CDRs) of the VH chain of the CD47 antibodies are highlighted below. In some embodiments, the amino acid sequence of VH CDR1 is GFNIKDYYLH (SEQ ID NO: 50), GYTFTYYYLH (SEQ ID NO: 57), GFTFTYYYLH (SEQ ID NO: 58), GYNFTYYYLH (SEQ ID NO: 59), GYTITYYYLH (SEQ ID NO: 60), GYTFKYYYLH (SEQ ID NO: 61), GYTFTDYYLH (SEQ ID NO: 62), GFTFTDYYLH (SEQ ID NO: 63), GFTITDYYLH (SEQ ID NO: 64), GYTFKDYYLH (SEQ ID NO: 65), or GFTFKDYYLH (SEQ ID NO: 66). In some embodiments, the amino acid sequence of VH CDR2 is WIDPDNGDTE (SEQ ID NO: 51), WIDPDQGDTE (SEQ ID NO: 72), WIDPDYGDTE (SEQ ID NO: 73), WIDPDSGDTE (SEQ ID NO: 74), WIDPDNADTE (SEQ ID NO: 75), or WIDPDNTDTE (SEQ ID NO: 76). In some embodiments, the amino acid sequence of VH CDR3 is NAAYGSSSYPMDY (SEQ ID NO: 52) or NAAYGSSPYPMDY (SEQ ID NO: 77).

```
EVQLQQSGAELVRSGASVKLSCTASGFNIKDYYLHWVKQRPEQGLEWIGWIDPDNGDTEFAPKFQGKATMTADTSS    (SEQ ID NO: 5)
NTAYLQLSSLTSEDTAVYYCNAAYGSSSYPMDYWGQGTSVTV

EVQLVQSGAEVKKPGATVKISCKVSGFNIKDYYLHWVQQAPGKGLEWMGWIDPDNGDTEYAEKFQGRVTITADTST    (SEQ ID NO: 6)
DTAYMELSSLRSEDTAVYYCNAAYGSSSYPMDYWGQGTTVTV

QMQLVQSGAEVKKTGSSVKVSCKASGFNIKDYYLHWVRQAPGQALEWMGWIDPDNGDTEYAQKFQDRVTITRDRSM    (SEQ ID NO: 7)
STAYMELSSLRSEDTAMYYCNAAYGSSSYPMDYWGQGTTVTV

EVQLVQSGAEVKKTGSSVKVSCKASGFNIKDYYLHWVRQAPGQALEWMGWIDPDNGDTEYAQKFQDRVTITRDRSM    (SEQ ID NO: 8)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNGDTEYAQKFQGRVTMTADTSS    (SEQ ID NO: 9)
NTAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNGDTEYAQKFQGRVTMTEDTST    (SEQ ID NO: 10)
DTAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDQGDTEYAQKFQDRVTITRDRSM    (SEQ ID NO: 11)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDYGDTEYAQKFQDRVTITRDRSM    (SEQ ID NO: 12)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDSGDTEYAQKFQDRVTITRDRSM    (SEQ ID NO: 13)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNADTEYAQKFQDRVTITRDRSM    (SEQ ID NO: 14)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNTDTEYAQKFQDRVTITRDRSM    (SEQ ID NO: 15)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNGDTEYAQKFQDRVTITRDRSM    (SEQ ID NO: 16)
STAYMELSSLRSEDTAMYYCNAAYGSSSYPMDYWGQGTTVTV

QMQLVQSGAEVKKTGSSVKVSCKASGYTFTYYYLHWVRQAPGQALEWMGWIDPDNGDTEYAQKFQDRVTITRDRSM    (SEQ ID NO: 17)
STAYMELSSLRSEDTAMYYCNAAYGSSSYPMDYWGQGTTVTV

QMQLVQSGAEVKKTGSSVKVSCKASGFTFTYYYLHWVRQAPGQALEWMGWIDPDNGDTEYAQKFQDRVTITRDRSM    (SEQ ID NO: 18)
STAYMELSSLRSEDTAMYYCNAAYGSSSYPMDYWGQGTTVTV

QMQLVQSGAEVKKTGSSVKVSCKASGYNFTYYYLHWVRQAPGQALEWMGWIDPDNGDTEYAQKFQDRVTITRDRSM    (SEQ ID NO: 19)
STAYMELSSLRSEDTAMYYCNAAYGSSSYPMDYWGQGTTVTV

QMQLVQSGAEVKKTGSSVKVSCKASGYTITYYYLHWVRQAPGQALEWMGWIDPDNGDTEYAQKFQDRVTITRDRSM    (SEQ ID NO: 20)
STAYMELSSLRSEDTAMYYCNAAYGSSSYPMDYWGQGTTVTV

QMQLVQSGAEVKKTGSSVKVSCKASGYTFKYYYLHWVRQAPGQALEWMGWIDPDNGDTEYAQKFQDRVTITRDRSM    (SEQ ID NO: 21)
STAYMELSSLRSEDTAMYYCNAAYGSSSYPMDYWGQGTTVTV

QMQLVQSGAEVKKTGSSVKVSCKASGYTFTDYYLHWVRQAPGQALEWMGWIDPDNGDTEYAQKFQDRVTITRDRSM    (SEQ ID NO: 22)
STAYMELSSLRSEDTAMYYCNAAYGSSSYPMDYWGQGTTVTV

QMQLVQSGAEVKKTGSSVKVSCKASGFTFTDYYLHWVRQAPGQALEWMGWIDPDNGDTEYAQKFQDRVTITRDRSM    (SEQ ID NO: 23)
STAYMELSSLRSEDTAMYYCNAAYGSSSYPMDYWGQGTTVTV

QMQLVQSGAEVKKTGSSVKVSCKASGFTITDYYLHWVRQAPGQALEWMGWIDPDNGDTEYAQKFQDRVTITRDRSM    (SEQ ID NO: 24)
STAYMELSSLRSEDTAMYYCNAAYGSSSYPMDYWGQGTTVTV
```

```
QMQLVQSGAEVKKTGSSVKVSCKASGYTFKDYYLHWVRQAPGQALEWMGWIDPDNGDTEYAQKFQDRVTITRDRSM    (SEQ ID NO: 25)
STAYMELSSLRSEDTAMYYCNAAYGSSSYPMDYWGQGTTVTV

QMQLVQSGAEVKKTGSSVKVSCKASGFTFKDYYLHWVRQAPGQALEWMGWIDPDNGDTEYAQKFQDRVTITRDRSM    (SEQ ID NO: 26)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNGDTEYAQKFQDRVTITRDRSM    (SEQ ID NO: 27)
STAYMELSSLRSEDTAMYYCNAAYGSSSYPMDYWGQGTTVTV

QMQLVQSGAEVKKTGSSVKVSCKASGFNIKDYYLHWVRQAPGQALEWMGWIDPDNGDTEYAQKFQDRVTITRDRSM    (SEQ ID NO: 28)
STAYMELSSLRSEDTAMYYCNAAYGSSSYPMDYWGQGTTVTV

EVQLVQSGAEVKKPGATVKISCKVSGFNIKDYYLHWVRQAPGQALEWMGWIDPDNGDTEYAQKFQDRVTITRDRSM    (SEQ ID NO: 29)
STAYMELSSLRSEDTAMYYCNAAYGSSSYPMDYWGQGTTVTV

EVQLVQSGAEVKKPGATVKISCKVSGFNIKDYYLHWQQAPGKGLEWMGWIDPDNGDTEYAQKFQDRVTITRDRSM     (SEQ ID NO: 30)
STAYMELSSLRSEDTAMYYCNAAYGSSSYPMDYWGQGTTVTV
```

Variable light (VL) chain regions of the CD47 antibodies are provided below. The CDRs of the VL chain of the CD47 antibodies are highlighted below. In some embodiments, the amino acid sequence of VL CDR1 is KASQDIHRYLS (SEQ ID NO: 53), RASQDIHRYLA (SEQ ID NO: 67), or RARQGIHRYLS (SEQ ID NO: 68). In some embodiments, the amino acid sequence of VL CDR2 is RANRLVD (SEQ ID NO: 54), RANRLQS (SEQ ID NO: 69), RANRRAT (SEQ ID NO: 70), or RANRLVS (SEQ ID NO: 71). In some embodiments, the amino acid sequence of VL CDR3 is LQYDEFPYT (SEQ ID NO: 55).

```
DIKMTQSPSSLYASLGERVTITCKASQDIHRYLSWFQQKPGKSPKILIYRANRLVDGVPSRFSGSGSGQDYSLTIS    (SEQ ID NO: 31)
SLEYEDMGIYYCLQYDEFPYTFGGGTKLEMK

DIKMTQSPSSLYASLGERVTITCKASQDIHRYLSWFQQKPGKSPKILIYRANRLVDGVPSRFSGSGSGQDYSLTIS    (SEQ ID NO: 32)
SLEYEDMGIYYCLQYDEFPYTFGGGTKLEIK

DIQMTQSPSSLSASVGDRVTITCKASQDIHRYLSWYQQKPGKAPKLLIYRANRLVDGVPSRFSGSGSGTDFTFTIS   (SEQ ID NO: 33)
SLQPEDIATYYCLQYDEFPYTFGGGTKVEIK

DIQMTQSPSSLSADVGDRVTITCKASQDIHRYLSWFQQKPGKAPKSLIYRANRLVDGVPSRFSGSGSGTDFTLTIS   (SEQ ID NO: 34)
SLQPEDFATYYCLQYDEFPYTFCCCTKVEIK

NIQMTQSPSAMSADVGDRVTITCKASQDIHRYLSWFQQKPGKVPKHLIYRANRLVDGVPSRFSGSGSGTEFTLTIS   (SEQ ID NO: 35)
SLQPEDFATYYCLQYDEFPYTFGGGTKVEIK

DIQMTQSPSSLSASVGDRVTITCKASQDIHRYLSWYQQKPGKAPKRLIYRANRLVDGVPSRFSGSGSGTEFTLTIS   (SEQ ID NO: 36)
SLQPEDFATYYCLQYDEFPYTFGGGTKVEIK

DIQMTQSPSSLSASVGDRVTITCRASQDIHRYLAWYQQKPGKVPKLLIYRANRLQSGVPSRFSGSGSGTDFTLTIS   (SEQ ID NO: 37)
SLQPEDVATYYCLQYDEFPYTFGQGTKVEIK

EIVLTQSPATLSLSPGERATLSCRASQDIHRYLAWYQQKPGQAPRLLIYRANRRATGIPARFSGSGSGTDFTLTIS   (SEQ ID NO: 38)
SLEPEDFAVYYCLQYDEFPYTGFQGTRLEIK

DIQMTQSPSAMSADVGDRVTITCKASQDIHRYLSWFQQKPGKVPKHLIYRANRLVDGVPSRFSGSGSGTEFTLTIS   (SEQ ID NO: 39)
SLQPEDFATYYCLQYDEFPYTFGGGTKVEIK

NIQMTQSPSAMSASVGDRVTITCRARQGIHRYLSWFQQKPGKVPKHLIYRANRLVDGVPSRFSGSGSGTEFTLTIS   (SEQ ID NO: 40)
SLQPEDFATYYCLQYDEFPYTFGGGTKVEIK

NIQMTQSPSAMSADVGDRVTITCKASQDIHRYLSWFQQKPGKVPKILIYRANRLVDGVPSRFSGSGSGTEFTLTIS   (SEQ ID NO: 41)
SLQPEDFATYYCLQYDEFPYTFGGGTKVEIK

NIQMTQSPSAMSASVGDRVTITCKASQDIHRYLSWFQQKPGKVPKHLIYRANRLVSGVPSRFSGSGSGTEFTLTIS   (SEQ ID NO: 42)
SLQPEDFATYYCLQYDEFPYTFGGGTKVEIK

NIQMTQSPSAMSASVGDRVTITCRARQGIHRYLSWFQQKPGKVPKILIYRANRLVDGVPSRFSGSGSGTEFTLTIS   (SEQ ID NO: 43)
SLQPEDFATYYCLQYDEFPYTFGGGTKVEIK

NIQMTQSPSAMSASVGDRVTITCRARQGIHRYLSWFQQKPGKVPKHLIYRANRLVSGVPSRFSGSGSGTEFTLTIS   (SEQ ID NO: 44)
SLQPEDFATYYCLQYDEFPYTFGGGTKVEIK

NIQMTQSPSAMSADVGDRVTITCKASQDIHRYLSWFQQKPGKVPKLLIYRANRLVDGVPSRFSGSGSGTEFTLTIS   (SEQ ID NO: 45)
SLQPEDFATYYCLQYDEFPYTFGGGTKVEIK
```

-continued

```
NIQMTQSPSAMSASVGDRVTITCKASQDIHRYLSWFQQKPGKVPKLLIYRANRLVSGVPSRFSGSGSGTEFTLTIS  (SEQ ID NO: 46)
SLQPEDFATYYCLQYDEFPYTFGGGTKVEIK

NIQMTQSPSAMSADVGDRVTITCRARQGIHRYLSWFQQKPGKVPKLLIYRANRLVSGVPSRFSGSGSGTEFTLTIS  (SEQ ID NO: 47)
SLQPEDFATYYCLQYDEFPYTFGGGTKVEIK
```

In some cases, the CD47 antibodies described herein comprise a variable heavy chain region selected from SEQ ID NOs: 5-30 and a variable light chain region selected from SEQ ID NOs: 31-47. An exemplary CD47 antibody comprises a variable heavy chain region set forth in SEQ ID NO: 5 and a variable light chain region set forth in SEQ ID NO: 31; a variable heavy chain region set forth in SEQ ID NO: 7 and a variable light chain region set forth in SEQ ID NO: 35; a variable heavy chain region set forth in SEQ ID NO: 11 and a variable light chain region set forth in SEQ ID NO: 42, a variable heavy chain region set forth in SEQ ID NO: 5 and a variable light chain region set forth in SEQ ID NO: 32, a variable heavy chain region set forth in SEQ ID NO: 7 and a variable light chain region set forth in SEQ ID NO: 33, a variable heavy chain region set forth in SEQ ID NO: 7 and a variable light chain region set forth in SEQ ID NO: 34, a variable heavy chain region set forth in SEQ ID NO: 7 and a variable light chain region set forth in SEQ ID NO: 36, a variable heavy chain region set forth in SEQ ID NO: 7 and a variable light chain region set forth in SEQ ID NO: 37, a variable heavy chain region set forth in SEQ ID NO: 7 and a variable light chain region set forth in SEQ ID NO: 38, a variable heavy chain region set forth in SEQ ID NO: 29 and a variable light chain region set forth in SEQ ID NO: 35, a variable heavy chain region set forth in SEQ ID NO: 30 and a variable light chain region set forth in SEQ ID NO: 35, a variable heavy chain region set forth in SEQ ID NO: 7 and a variable light chain region set forth in SEQ ID NO: 43, a variable heavy chain region set forth in SEQ ID NO: 11 and a variable light chain region set forth in SEQ ID NO: 43, a variable heavy chain region set forth in SEQ ID NO: 11 and a variable light chain region set forth in SEQ ID NO: 47, a variable heavy chain region set forth in SEQ ID NO: 15 and a variable light chain region set forth in SEQ ID NO: 43, a variable heavy chain region set forth in SEQ ID NO: 15 and a variable light chain region set forth in SEQ ID NO: 44, a variable heavy chain region set forth in SEQ ID NO: 11 and a variable light chain region set forth in SEQ ID NO: 44, a variable heavy chain region set forth in SEQ ID NO: 22 and a variable light chain region set forth in SEQ ID NO: 35, a variable heavy chain region set forth in SEQ ID NO: 7 and a variable light chain region set forth in SEQ ID NO: 39, a variable heavy chain region set forth in SEQ ID NO: 8 and a variable light chain region set forth in SEQ ID NO: 39, a variable heavy chain region set forth in SEQ ID NO: 16 and a variable light chain region set forth in SEQ ID NO: 35, a variable heavy chain region set forth in SEQ ID NO: 20 and a variable light chain region set forth in SEQ ID NO: 35, a variable heavy chain region set forth in SEQ ID NO: 21 and a variable light chain region set forth in SEQ ID NO: 35, a variable heavy chain region set forth in SEQ ID NO: 17 and a variable light chain region set forth in SEQ ID NO: 35, a variable heavy chain region set forth in SEQ ID NO: 28 and a variable light chain region set forth in SEQ ID NO: 35, or a variable heavy chain region set forth in SEQ ID NO: 27 and a variable light chain region set forth in SEQ ID NO: 35.

The CD47 antibodies described herein comprise any one of the VH regions provided in SEQ ID NOs: 5-30 paired with any one of the VL regions provided in SEQ ID NOs: 31-47. Specifically, the CD47 antibodies described herein comprise any one of the VH regions provided in SEQ ID NOs: 5, 7, 8, 11, 15-17, 20-22, and 27-30 paired with any one of the VL regions provided in SEQ ID NOs: 31-39, 42, 43, 44, and 47.

The CD47 antibodies described herein comprise any one of the VH CDR1 regions provided in SEQ ID NO: 50, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, and SEQ ID NO: 66, any one of the VH CDR2 regions provided in SEQ ID NO: 51, SEQ ID NO: 72, SEQ ID NO: 73, SEQ ID NO: 74, SEQ ID NO: 75, and SEQ ID NO: 76, any one of the VH CDR3 regions provided in SEQ ID NO: 52 and SEQ ID NO: 77, any one of the VL CDR1 regions provided in SEQ ID NO: 53, SEQ ID NO: 67, and SEQ ID NO: 68, any one of the VL CDR2 regions provided in SEQ ID NO: 54, SEQ ID NO: 69, SEQ ID NO: 70, and SEQ ID NO: 71, and the VL CDR3 region provided in SEQ ID NO: 55.

Those skilled in the art will recognize that it is possible to determine, without undue experimentation, if a monoclonal antibody has the same specificity as a monoclonal antibody of the invention (e.g., the 2A1 antibody, or an antibody having a variable heavy chain selected from SEQ ID NOs: 5-31, and a variable light chain selected from SEQ ID NOs: 31-47) by ascertaining whether the former prevents the latter from binding to CD47. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of monoclonal antibody of the invention is to pre-incubate the monoclonal antibody of the invention with soluble CD47 protein (with which it is normally reactive), and then add the monoclonal antibody being tested to determine if the monoclonal antibody being tested is inhibited in its ability to bind CD47. If the monoclonal antibody being tested is inhibited then, in all likelihood, it has the same, or functionally equivalent, epitopic specificity as the monoclonal antibody of the invention.

Antibodies of the Present Invention

Screening of monoclonal antibodies of the invention, can be also carried out, e.g., by measuring CD47- and/or CD47/SIRPα-mediated signaling, and determining whether the test monoclonal antibody is able to modulate, block, inhibit, reduce, antagonize, neutralize or otherwise interfere with CD47- and/or CD47/SIRPα-mediated signaling. These assays can include competitive binding assays. Additionally, these assays can measure a biologic readout, for example the ability to promote phagocytosis of a CD47 expressing cell by a macrophage, as is described in Example 9 (FIG. 9).

Various procedures known within the art may be used for the production of monoclonal antibodies directed against CD47, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The CD47 antibodies of the invention are monoclonal antibodies. Monoclonal antibodies that modulate, block, inhibit, reduce, antagonize, neutralize or otherwise interfere with CD47- and/or CD47/SIRPα-mediated cell signaling are generated, e.g., by immunizing an animal with membrane bound and/or soluble CD47, such as, for example, human CD47 or an immunogenic fragment, derivative or variant thereof. Alternatively, the animal is immunized with cells transfected with a vector containing a nucleic acid molecule encoding CD47 such that CD47 is expressed and associated with the surface of the transfected cells. Alternatively, the antibodies are obtained by screening a library that contains antibody or antigen binding domain sequences for binding to CD47. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to CD47.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816, 567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as Chinese hamster ovary (CHO) cells, Human Embryonic Kidney (HEK) 293 cells, simian COS cells, PER.C6®, NS0 cells, SP2/0, YB2/0, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Human Antibodies and Humanization of Antibodies

Monoclonal antibodies of the invention include fully human antibodies or humanized antibodies. These antibodies are suitable for administration to humans without engendering an immune response by the human against the administered immunoglobulin.

A CD47 antibody is generated, for example, using the procedures described in the Examples provided below. For example, CD47 antibodies of the invention are identified using a modified RIMMS (Repetitive Immunization Multiple Sites) immunization strategy in mice and subsequent hybridoma generation.

In other, alternative methods, a CD47 antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of cd47 or fragments thereof. In another approach, a CD47 antibody can be produced by a process wherein at least one step of the process includes immunizing a transgenic, non-human animal with human CD47 protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and No. 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963; 6,150,584; 6,114,598; 6,075,181; and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and an immune variable region, it is expected that certain human anti-chimeric antibody (HACA) responses will be observed, particularly in chronic or multi-dose utilizations of the antibody. Thus, it would be desirable to provide fully human antibodies against CD47 in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693, 761; 5,693,792; 5,714,350; and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG2, IgG3, and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to CD47 expressing cells, soluble forms of CD47, epitopes or peptides thereof, and expression libraries thereto (See e.g., U.S. Pat. No. 5,703,057) which can thereafter be screened as described above for the activities described herein.

The CD47 antibodies of the invention can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G., et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CD47 in a sample. The antibody can also be used to try to bind to and disrupt CD47- and/or the CD47/SIRPα interaction and CD47/SIRPα-mediated signaling.

Techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an $F(ab')_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) $F_v$ fragments.

The invention also includes $F_v$, Fab, Fab' and $F(ab')_2$ CD47 fragments, single chain CD47 antibodies, single domain antibodies (e.g., nanobodies or VHHs), bispecific CD47 antibodies, and heteroconjugate CD47 antibodies.

Bispecific antibodies are antibodies that have binding specificities for at least two different antigens. In the present case, one of the binding specificities is for CD47. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant CD47 signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6[3-(2-pyridyldithio)propionamido]hexanoate (Pierce Chem. Co., Cat #21651G); (iv) Sulfo-LC-SPDP (sulfosuccinimidyl 6[3-(2-pyridyldithio)-propianamide]hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against CD47

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, antibodies of the invention, which include a monoclonal antibody of the invention, may be used as therapeutic agents. Such agents will generally be employed to diagnose, prognose, monitor, treat, alleviate, and/or prevent a disease or pathology associated with aberrant CD47 expression, activity and/or signaling in a subject. A therapeutic regimen is carried out by identifying a subject, e.g., a human patient suffering from (or at risk of developing) a disease or disorder associated with aberrant CD47 expression, activity and/or signaling, e.g., a cancer or other neoplastic disorder, using standard methods. An antibody preparation, preferably one having high specificity and high affinity for its target antigen, is administered to the subject and will generally have an effect due to its binding with the target. Administration of the antibody may abrogate or inhibit or interfere with the expression, activity and/or signaling function of the target (e.g., CD47). Administration of the antibody may abrogate or inhibit or interfere with the binding of the target (e.g., CD47) with an endogenous ligand (e.g., SIRPα) to which it naturally binds. For example, the antibody binds to the target and modulates, blocks, inhibits, reduces, antagonizes, neutralizes, or otherwise interferes with CD47 expression, activity and/or signaling.

Diseases or disorders related to aberrant CD47 expression, activity and/or signaling include, by way of non-limiting example, hematological cancer and/or solid tumors. Hematological cancers include, e.g., leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

Symptoms associated with cancers and other neoplastic disorders include, for example, inflammation, fever, general malaise, fever, pain, often localized to the inflamed area, loss of appetite, weight loss, edema, headache, fatigue, rash, anemia, muscle weakness, muscle fatigue and abdominal symptoms such as, for example, abdominal pain, diarrhea or constipation.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 100 mg/kg body weight. Common dosing frequencies may range, for example, from twice daily to once a week.

Efficaciousness of treatment is determined in association with any known method for diagnosing or treating the particular inflammatory-related disorder. Alleviation of one or more symptoms of the inflammatory-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

In another embodiment, antibodies directed against CD47 may be used in methods known within the art relating to the localization and/or quantitation of CD47 (e.g., for use in measuring levels of CD47 and/or both CD47 and SIRPα within appropriate physiological samples, for use in diagnostic methods, for use in imaging the protein, and the like). In a given embodiment, antibodies specific to CD47, or derivative, fragment, analog or homolog thereof, that contain the antibody derived antigen binding domain, are utilized as pharmacologically active compounds (referred to hereinafter as "Therapeutics").

In another embodiment, an antibody specific for CD47 can be used to isolate a CD47 polypeptide, by standard techniques, such as immunoaffinity, chromatography or immunoprecipitation. Antibodies directed against the CD47 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody according to the invention can be used as an agent for detecting the presence of CD47 and/or both CD47 and SIRPα protein (or a protein fragment thereof) in a sample. In some embodiments, the antibody contains a detectable label. Antibodies are polyclonal, or more preferably, monoclonal. An intact antibody, or a fragment thereof (e.g., Fab, scFv, or F(ab')$_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Therapeutic Administration and Formulations of CD47 Antibodies

The antibodies of the invention (also referred to herein as "active compounds"), and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Such combination therapies may advantageously utilize lower dosages of the administered therapeutic agents, thus avoiding possible toxicities or complications associated with the various monotherapies.

Preferred therapeutic agents used in combination with an antibody of the invention are those agents that interfere at different stages in an inflammatory response. In one embodiment, one or more antibodies described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof.

In other embodiments, the antibodies of the invention are used as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Design and Generation of Other Therapeutics

In accordance with the present invention and based on the activity of the antibodies that are produced and characterized herein with respect to CD47, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies—one with a specificity to CD47 and another to a second molecule that are conjugated together, (ii) a single antibody that has one chain specific to CD47 and a second chain specific to a second molecule, or (iii) a single chain antibody that has specificity to CD47 and a second molecule. Such bispecific antibodies are generated using techniques that are well known for example, in connection with (i) and (ii) See e.g., Fanger et al. Immunol Methods 4:72-81 (1994) and Wright et al. Crit, Reviews in Immunol. 12125-168 (1992), and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing CD47.

In connection with the generation of therapeutic peptides, through the utilization of structural information related to CD47 and antibodies thereto, such as the antibodies of the invention or screening of peptide libraries, therapeutic peptides can be generated that are directed against CD47. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the CD47 molecule (or a form, such as a splice variant or alternate form) is functionally active in a disease process, it will also be possible to design gene and antisense therapeutics thereto through conventional techniques. Such modalities can be utilized for modulating the function of CD47. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the CD47 molecule and its interactions with other molecules in accordance with the present invention, such as SIRPα and/or the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of IL-6Rc. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of CD47 to SIRPα, or candidate or test compounds or agents that modulate or otherwise interfere with the signaling function of CD47 and/or CD47-SIRPα. Also provided are methods of identifying compounds useful to treat disorders associated with aberrant CD47 and/or CD47-SIRPα expression, activity and/or signaling. The screening methods can include those known or used in the art or those described herein. For example, CD47 can be immobilized on a microtiter plate and incubated with a candidate or test compound, e.g., a CD47 antibody, in the presence of SIRPα. Subsequently, bound SIRPα can be detected using a secondary antibody, and absorbance can be detected on a plate reader.

Methods of identifying compounds capable of promoting phagocytosis of tumor cells by macrophages are also provided. These methods can include those known or used in the art or those described herein. For example, macrophages are incubated with labeled tumor cells in the presence of a candidate compound, e.g., a CD47 antibody. After a period of time, the macrophages can be observed for internalization of the tumor label to identify phagocytosis. Additional details regarding these methods, e.g., SIRPα blocking assays and phagocytosis assays, are provided in the Examples.

The invention also includes compounds identified in the screening assays described herein.

In one embodiment, the invention provides assays for screening candidate or test compounds which modulate the signaling function of CD47. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates the signaling function of CD47 and/or the interaction between CD47 and SIRPα. In another embodiment, a soluble CD47 and/or both CD47 and SIRPα protein of the invention is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant CD47 and/or CD47-SIRPα signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a neutralizing antibody, which modulates or otherwise interferes with CD47 activity and/or signaling.

The screening methods disclosed herein may be performed as a cell-based assay or as a cell-free assay. The cell-free assays of the invention are amenable to use of either the soluble form or the membrane-bound form of CD47 and fragments thereof. In the case of cell-free assays comprising the membrane-bound form of CD47, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and micro-centrifuge tubes. In one embodiment, a fusion protein that adds a domain that allows one or both of the proteins to be bound to a matrix can be provided. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g., the 2A1 antibody, or an antibody having a variable heavy chain selected from SEQ ID NOs: 5-30 and a variable light chain selected from SEQ ID NOs: 31-47) or the antigen (e.g. CD47 protein) can be immobilized utilizing conjugation of biotin and streptavidin. Biotinylated antibody or antigen molecules can be prepared from biotin-NHS(N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic and Prophylactic Formulations

The CD47 MAbs of the invention are used in diagnostic and prophylactic formulations. In one embodiment, a CD47 MAb of the invention is administered to patients that are at risk of developing one or more of the aforementioned diseases, such as for example, without limitation, cancer or other neoplastic condition. A patient's or organ's predisposition to one or more of the aforementioned cancers or other neoplastic conditions can be determined using genotypic, serological or biochemical markers.

In another embodiment of the invention, the CD47 antibody is administered to human individuals diagnosed with a clinical indication associated with one or more of the aforementioned diseases, such as for example, without limitation, cancer or other neoplastic condition. Upon diagnosis, the CD47 antibody is administered to mitigate or reverse the effects of the clinical indication associated with one or more of the aforementioned diseases.

Antibodies of the invention are also useful in the detection of CD47 and/or SIRPα in patient samples and accordingly are useful as diagnostics. For example, the CD47 antibodies of the invention are used in in vitro assays, e.g., ELISA, to detect CD47 and/or SIRPα levels in a patient sample.

In one embodiment, a CD47 antibody of the invention is immobilized on a solid support (e.g., the well(s) of a microtiter plate). The immobilized antibody serves as a capture antibody for any CD47 and/or SIRPα that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of CD47 and/or SIRPα in the test sample is determined by comparison with a standard curve developed from the standard samples.

It will be appreciated that based on the results obtained using the CD47 antibodies of the invention in an in vitro diagnostic assay, it is possible to stage a disease (e.g., a clinical indication associated with ischemia, an autoimmune or inflammatory disorder) in a subject based on expression levels of CD47 and/or SIRPα. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Generation and Selection of CD47 Antibodies

CD47 antibodies were generated by immunizing mice with a recombinant protein representing CD47-IgV (immunoglobin-like variable-type), implementing a modified rapid immunization strategy in multiple sites (Kilpatrick et al. (1997) Rapid development of affinity matured monoclonal antibodies using RIMMS. Hybridoma 16, 381-389). In addition, half of the mice in the immunized group received a single injection of the anti-mouse GITR agonist antibody, DTA-1. Following the immunization schedule, lymph nodes from all mice (DTA-1 treated and untreated) were harvested and dissociated, thereby enabling B-cell isolation and subsequent fusion to a mouse myeloma cell line. Hybridoma supernatants were screened for binding to CD47 by ELISA and by flow cytometry on Daudi (ATCC# CCL-213) cells (FIG. 1A). Hybridoma supernatants were also analyzed for the ability to block the CD47-SIRPα interaction (FIG. 1B). Recombinant CD47 was immobilized on a Medisorp (NUNC) microtiter plate and subsequently incubated with the hybridoma supernatants in the presence of recombinant human SIRPα-ECD fused to a human IgG Fc domain. Bound SIRPα was detected using an HRP conjugated anti-human IgG Fc specific secondary antibody (Jackson Immuno Research), and absorbance at 650 nm detected in plate reader.

Example 2

Characterization of CD47 Antibodies

Figure 2B:
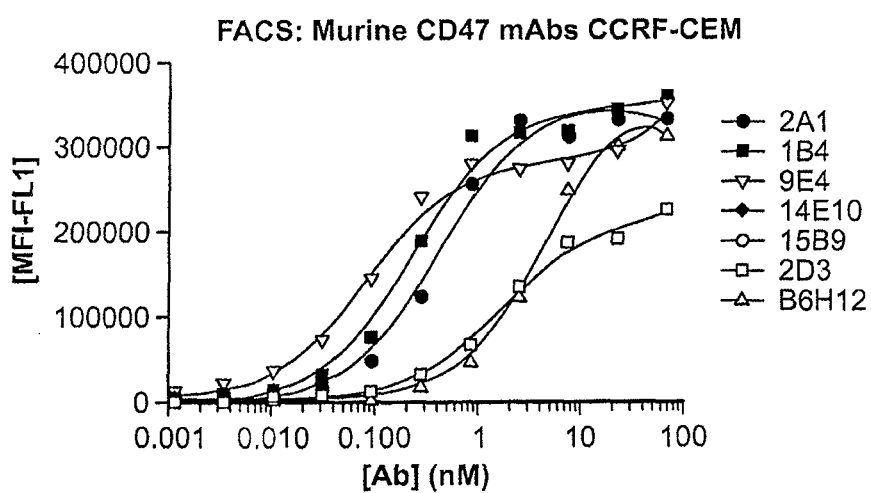

Exemplary murine CD47 antibodies of the present invention are shown in FIG. 2. Affinity ranking of SIRPα blocking CD47 antibodies was conducted by flow cytometry on Raji (ATCC# CCL-86) (FIG. 2A) and CCRF-CEM (ATCC# CCL-119) cells (FIG. 2B). Bound CD47 antibodies were detected using a FITC conjugated anti-mouse IgG secondary antibody (Jackson ImmunoResearch). The CD47 antibody known in the art, B6H12, was included as a positive control (See, e.g., U.S. Pat. No. 5,057,604). In FIG. 2B, both the B6H12 and the 2D3, a commercially available non-SIRPα blocking antibody, were compared to antibodies generated herein. The antibodies of the present invention display higher affinity toward the endogenous (cell surface) form of CD47 compared to the B6H12 and 2D3 antibodies.

Example 3

SIRPα Blocking Activity of CD47 Antibodies

Figure 3A:
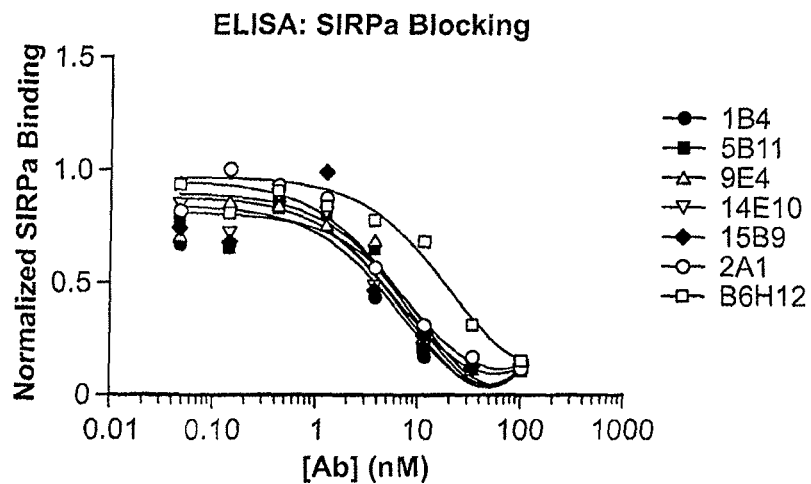
FIG. 3 is a series of graphs depicting the capacity of CD47 antibodies to block SIRPα binding using (A) an ELISA with recombinant human protein, or (B) by flow cytometry using CCRF-CEM cells and recombinant human SIRPα protein.

The potency of SIRPα blocking by CD47 antibodies was measured by an ELISA wherein recombinant His-tagged-CD47-IgV was immobilized on a Medisorp microtiter plate. Binding of recombinant SIRPα fused to an Fc domain of human IgG was monitored in the presence of increasing amounts of the CD47 antibodies. Bound SIRPα was determined using an HRP conjugated anti-human IgG (Fc specific) secondary antibody (Jackson ImmunoResearch). The antibodies of the present invention display enhanced potency of SIRPα blocking compared to the B6H12 antibody. FIG. 3A shows representative data of the ELISA based SIRPα blocking assay.

Figure 3B:
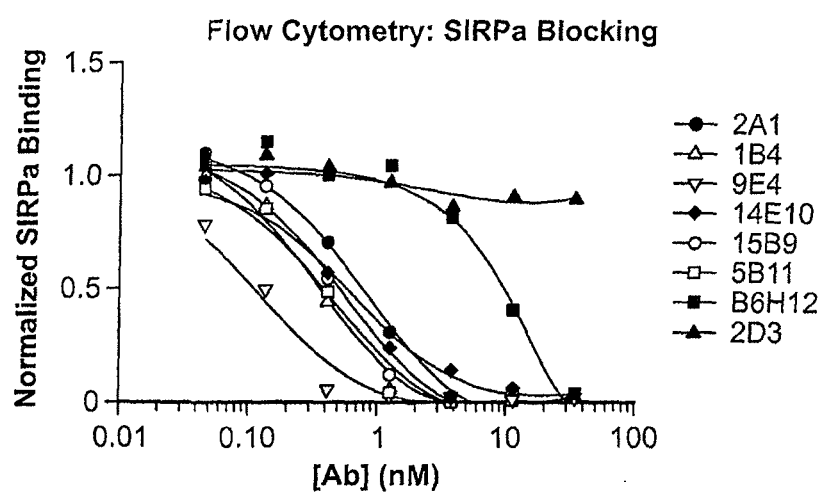

CD47 antibodies were analyzed by flow cytometry for their ability to block recombinant SIRPα binding to cell surface CD47. CCRF-CEM (ATCC# CCL-119) cells were used as the source of CD47 in the assay and binding of recombinant SIRPα fused to an Fc domain of human IgG was monitored in the presence of increasing amounts of the CD47 antibodies. Bound SIRPα was determined using an APC conjugated anti-human IgG (Fc specific) secondary antibody (Jackson ImmunoResearch) (FIG. 3B). B6H12 and commercially available non-SIRPα blocking CD47 antibody 2D3 where used a positive and negative controls respectively.

Example 4

CD47 Antibody-Mediated Homotypic Interactions

SIRPα blocking CD47 antibodies were analyzed for their ability to induce cellular clustering, as known as homotypic interactions, between CD47 positive cells. Daudi and Raji cells were used as candidate CD47 expressing cells lines. Among the antibodies examined, the 2A1 antibody of the present invention was the only SIRPα blocking antibody that did not promote homotypic interactions of CD47 expressing cells.

Example 5

Hemagglutination Activity of CD47 Antibodies

One example of a homotypic interaction is hemagglutination, as evidenced by RBC aggregation. CD47 antibodies were screened for RBC agglutination, as observed by the ability of an antibody to prevent the settling of human RBCs. Unexpectedly, the 2A1 antibody was found to be unique among other CD47 antibodies for its inability to promote hemagglutination, while having high affinity and the ability to block SIRPα. Other antibodies that displayed reduced hemagglutination did not block SIRPα binding to CD47.

To evaluate the hemagglutinating capacity of CD47 antibodies, human RBCs were diluted to 10% in PBS and incubated at 37° C. for 2-6 hours with a titration of CD47 antibodies in a round bottom 96 well plate. Evidence of hemagglutination is demonstrated by the presence of non-settled RBCs, appearing as a haze compared to a punctuate red dot of non-hemagglutinated RBCs. Unexpectedly, as shown in FIG. 4A, CD47 antibodies of the invention, particularly the antibody referred to herein as 2A1, did not exhibit hemagglutinating activity. The graph shows the quantitation of the hemagglutination assay, denoted "hemagglutination index" determined by quantitating the area of the RBC pellet in the presence of the antibody, normalized to that in the absence of the antibody.

The murine 9E4 antibody caused the most profound hemagglutination at all concentrations tested. Thus, The 9E4 antibody binds CD47 and blocks CD47 interaction with SIRPα; however, the 9E4 antibody causes profound hemagglutination.

The VH chain region of the 9E4 antibody is provided below.

(SEQ ID NO: 78)
EVQLRQSGPELVKPGASVKISCKASGYSFTDYYMYWVKQSRVRSLAWIGRINPYTGATGYDQNFKDKASLIVDKSS

STAYMELRSLTSEDSAVYYCARGRNRYDGWFAYWGQGTLVTV

The VL chain region of the 9E4 antibody is provided below.

(SEQ ID NO: 79)
EIQMTQTTSSLSASLGDRVTISCRASQDISNYLNWYQQKPDGTVKLLIYYTSRLHSGVPSRFSGSGSGTDYSLTIS

NLDQEDIATYFCQQGNALPPTFGGGTNLEIK

The control antibody B6H12 caused hemagglutination as is expected for SIRPα blocking CD47 antibodies.

Figure 4B:
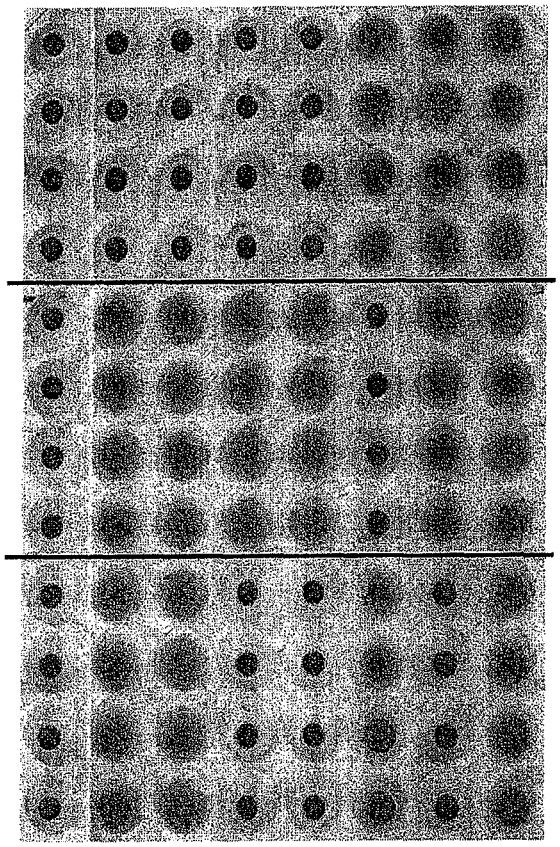
FIG. 4B shows that 2A1 is rare amongst many CD47 antibodies in its inability to agglutinate RBCs. Also shown is the lack of agglutinating activity by the human chimeric version of 2A1 (2A1-xi).

In order to investigate the uniqueness of the non-hemagglutinating activity of the 2A1 antibody, numerous other CD47 antibodies were screened in the RBC hemagglutination assay (FIG. 4B). Included in this assay was the chimeric version of the 2A1 antibody (2A1-xi), which consists of the murine variable heavy chain region of 2A1, the murine variable light chain region of 2A1 modified at amino acid 106 (i.e., M106I), and the constant regions of human IgG1 and human Igkappa. The VH and VL region sequences of 2A1 antibody and 2A1-xi antibody are provided in Table 1. Antibodies were tested at 12.5, 25, 50, and 100 nM. Unexpectedly, 2A1 is rare amongst the CD47 antibodies examined in FIG. 4B, in that it was the only antibody in FIG. 4B with absent or reduced hemagglutinating activities. FIG. 4E shows that 2A1, chimeric 2A1 (2A1-xi), and humanized variants do not cause hemagglutination.

Figure 4C:
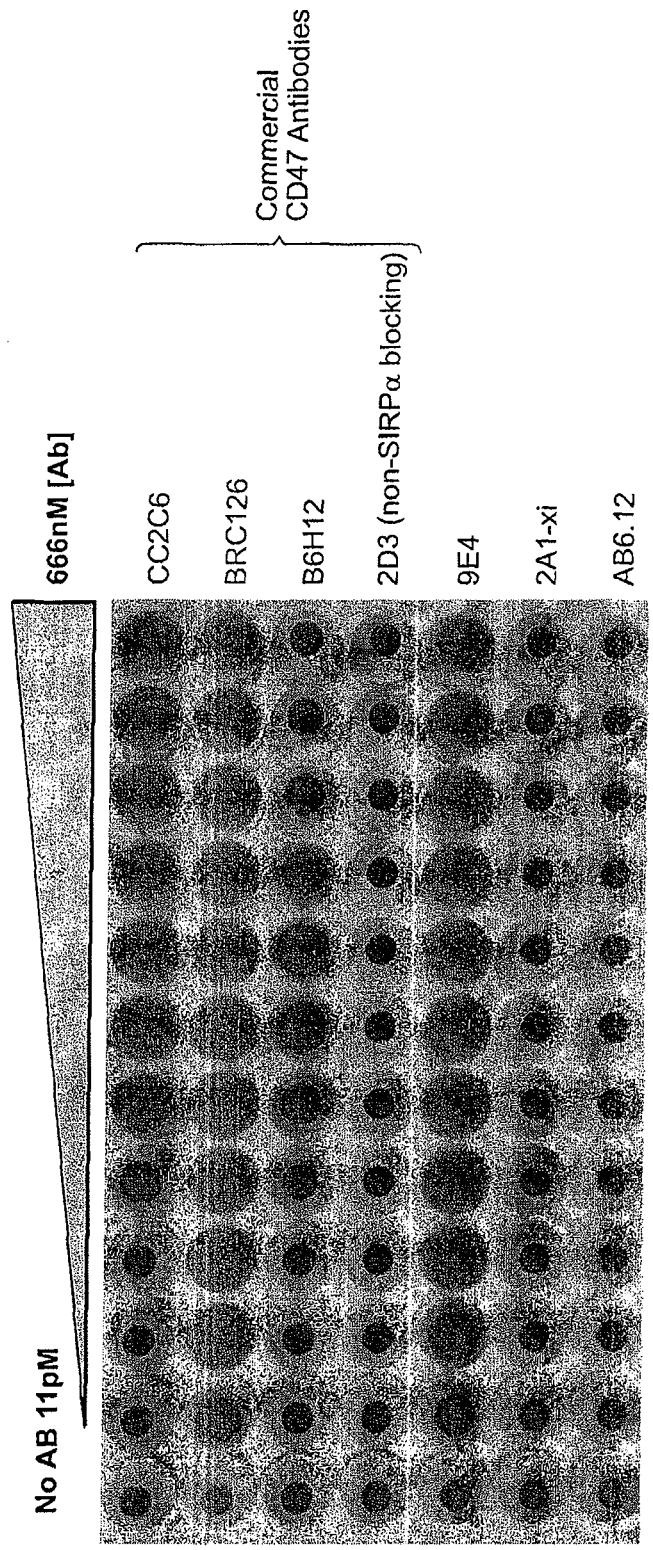
FIG. 4C shows that CD47 monoclonal antibody 2D3, which does not block SIRPα, does not cause hemagglutination.
Figure 4E:
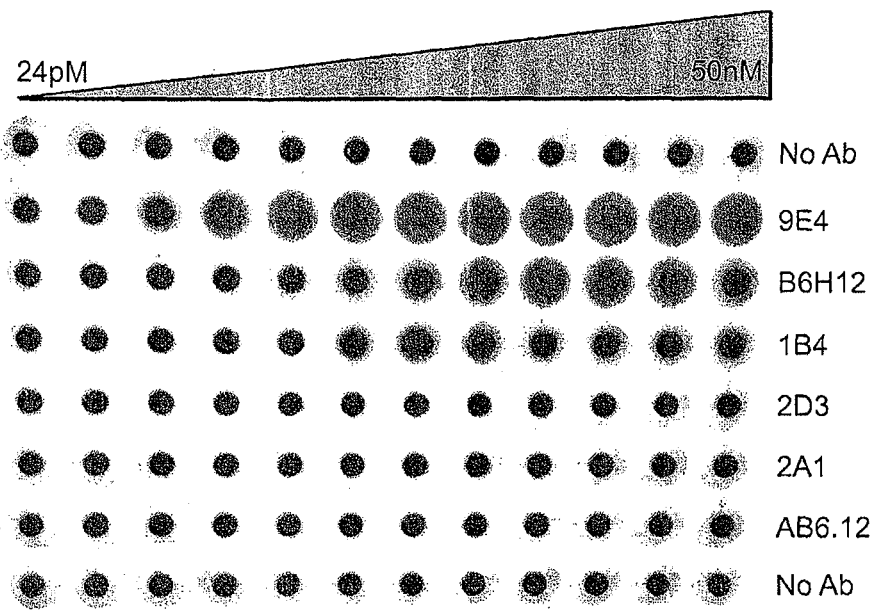
FIG. 4E demonstrates the more narrow concentration range for hemagglutination by the CD47 antibody, 1B4, whereas this effect is absent upon 2A1 binding.

FIG. 4C shows the results of screening additional CD47 antibodies in the RBC hemagglutination assay. As shown in FIG. 4C, the commercially available CD47 monoclonal antibody 2D3, which does not block SIRPα, did not cause hemagglutination. However, other commercially available CD47 antibodies (e.g., CC2C6, BRC126, and B6H12) which block SIRPα caused hemagglutination (FIG. 4C). Thus, prior to the invention described herein, existing antibodies that blocked SIRPα caused hemagglutination, while existing antibodies, such as 2D3, that did not block SIRPα did not cause hemagglutination. Taken together, the antibodies of the invention (e.g., the 2A1 antibody and its humanized derivatives) are unique among existing CD47 antibodies in their ability to block SIRPα, but not cause hemagglutination.

A high concentration range of select CD47 antibodies was retested in the hemagglutination assay (FIG. 4D). This assay revealed a pro-zone effect of hemagglutination by B6H12 and 9E4, wherein hemagglutination was reduced at high and low ends of the concentration range tested. The graphical representation of the hemagglutination index also highlights the pro-zone effect. The pro-zone effect was also evident in FIGS. 4C and 4E. Importantly, the mouse 2A1 and chimeric 2A1 CD47 antibodies were devoid of hemagglutinating activity at all concentrations.

As shown in FIG. 4E, the murine 1B4 antibody displayed a narrow range of hemagglutination.

The VH chain region of the 1B4 antibody is provided below.

(SEQ ID NO: 80)
QIQLQQSGPELVKPGASVKISCKASGYTFTDYYIHWVKQRPGQGLEWIGWIYPGSGNTKYNERFKGKATLTVATSS

STAYMQLSSLTSEDTAVYFCARREEDYFDYWGQGTLVTV

The VL chain region of the 1B4 antibody is provided below.

(SEQ ID NO: 81)
DIVMSQSPSSLAVSVGEKVTMSCKSSQSLLYSSNQKNYLTWYQQKPGQSPKLLIYWASTRESGVPDRFTGSGSGTD

FTLTISSVKAEDLAVYYCQQYYSYPLTFGAGTKLEIK

Figure 4F:
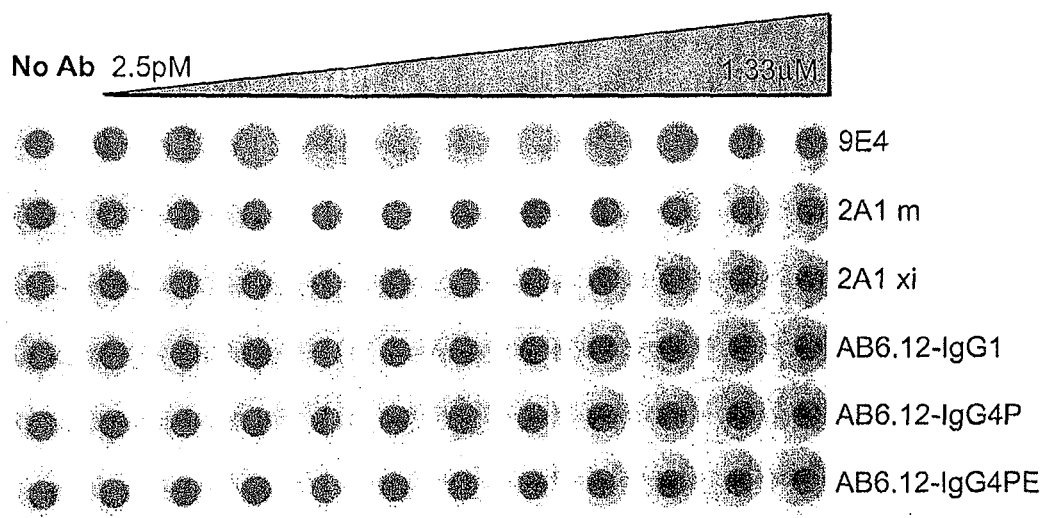
FIG. 4F shows that 2A1, chimeric 2A1 (2A1-xi), and humanized variants do not cause hemagglutination. In most experiments the 9E4 antibody and the commercial B6H12 antibody were used as positive controls for hemagglutination. Other commercially available antibodies used in these assays were the SIRPα blocking antibodies, BRC126 and CC2C6, and the non-SIRPα blocking antibody, 2D3.

The hemagglutinating capacity of humanized antibodies derived from the murine 2A1 was tested as above. Importantly, the representative humanized antibody AB6.12 in numerous human IgG isotypes (IgG1, IgG4-S228P, and IgG4-S228P/L235E) did not cause any RBC hemagglutination. 2A1 and 2A1-xi were included as controls for non-hemagglutinating antibodies, whereas B6H12 and 9E4 were included as positive controls for hemagglutination (FIG. 4F).

Example 6

Binding to Cynomolgus Monkey CD47

Figure 5:
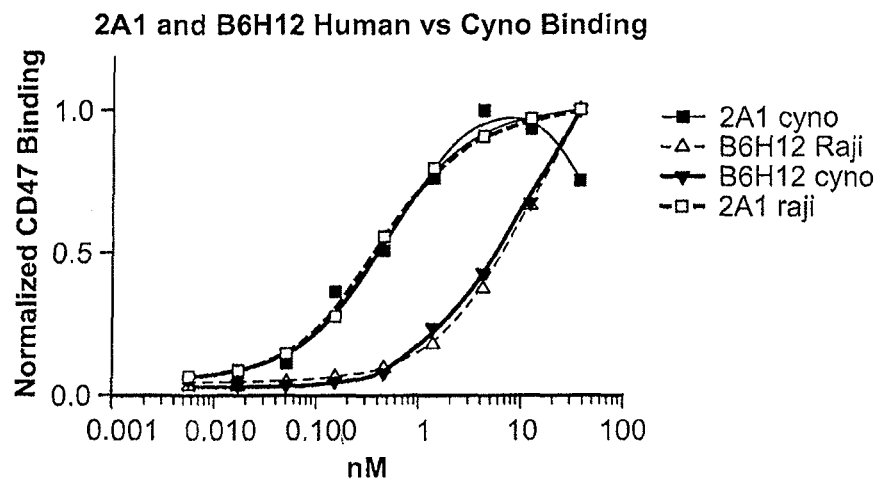
FIG. 5 is a graph showing 2A1 and B6H12 binding to cynomolgus (cyno) monkey B-cells and Raji, as assessed by flow cytometry. 2A1 binds human and cyno CD47 with equivalent affinity, as does B6H12, albeit with lower affinity to both human and cyno CD47 than 2A1.

The ability of murine 2A1 to bind to cynomolgus (cyno) monkey CD47 was assessed. The B6H12 antibody has previously been reported to be cross-reactive with cyno CD47 and was used as a positive control for the presence on cyno CD47 in the assay. The experiment to measure binding of 2A1 to cynomolgus monkey CD47 was designed to compare binding of 2A1 to CD47 on cynomolgus monkey B-cells and human cells, wherein the Raji cell line was used as a human CD47 positive cell. Cynomolgus peripheral blood mononuclear cells (PBMCs) were isolated from cynomolgus whole blood by ficoll-paque gradient centrifugation. Cynomolgus and human B-cells (Raji) were labeled with the human CD20 antibody ofatumumab (Arzerra) at 10 μg/ml, and reacted with a dilution series of murine CD47 antibody 2A1 or B6H12. B-cells labeled with human CD20 antibody were detected with polyclonal anti-human antibody conjugated to DyLite 649, while the CD47 murine antibodies were detected with polyclonal anti-mouse antibody conjugated to DyLite 488. Cells were analyzed by flow cytometry, first gated on live cells by FSC and SSC, then on cells positive for FL4 (CD20 positive), and lastly the median FL1 (CD47 positive) was measured. The data were normalized by dividing the signal at each concentration by the maximum signal for each antibody on each cell population. The normalized results shown in FIG. 5 reveal that 2A1 does cross react with cyno CD47 and has identical affinity as compared to human CD47. Consistent with the results presented above, B6H12 had lower affinity for cell surface CD47 on both Raji and cynomolgus B-cells compared to antibodies of the present invention.

Example 7

Chimeric Antibody Generation

In order to identify the sequences of the variable regions of the heavy (VH) and light (VL) chains of the murine 2A1 antibody, ribonucleic acid (RNA) was isolated from the hybridoma and utilized in reverse transcription polymerase chain reaction (RT-PCR) (Phusion RT-PCR Kit Thermo Scientific) to generate first strand cDNA. A degenerative primer set that covers the complete repertoire of murine of antibody leader sequences of both VH and VL was used in a PCR wherein the first strand cDNA served as the template.

The forward primers (murine IgG leader) are provided below.

| Name | Sequence |
| --- | --- |
| VH1-1 | CACTGCAGGTRTCCACTCC (SEQ ID NO: 82) |
| VH1-2 | CATAGCAGGTGTCCACTCC (SEQ ID NO: 83) |
| VH1-3 | CRCTACAGGTGTCCACTCC (SEQ ID NO: 84) |
| VH1-4 | GCYACAGMTGTCCACTCC (SEQ ID NO: 85) |
| VH1-5 | CACTGCAGGTGTCCWMTCC (SEQ ID NO: 86) |
| VH1-6 | CRCTRCAGGTGTKCACTCC (SEQ ID NO: 87) |

| Name | Sequence |
| --- | --- |
| VH1-7 | GCTAWMGGTGTCCACTCC (SEQ ID NO: 88) |
| VH1-8 | CCTCAGGTGTCCACTCC (SEQ ID NO: 89) |
| VH1-9 | GCTACAGGTGCTCACTCC (SEQ ID NO: 90) |
| VH1-10 | CACTGCAGGTGTCCTCTCT (SEQ ID NO: 91) |
| VH1-11 | CAYTGCAGGTGTCCAYTGC (SEQ ID NO: 92) |
| VH1-12 | GCTAMMGGTGTCCACTTC (SEQ ID NO: 93) |
| VH1-13 | CTCCTGTCAKTAACTKCAGGT (SEQ ID NO: 94) |
| VH1-14 | CAACTGCAGGTGTCTCTCT (SEQ ID NO: 95) |
| VH1-15 | CRCTRCAGGYGTCCACTCT (SEQ ID NO: 96) |
| VH2-1 | CCAAGCTGTATCCTTTCC (SEQ ID NO: 97) |
| VH2-2 | CCAAGCTGTGTCCTRTCC (SEQ ID NO: 98) |
| VH3-1 | CTTGACAGYCVTTCCKGGT (SEQ ID NO: 99) |
| VH3-2 | CTTCACAGCCTTTCCTGGT (SEQ ID NO: 100) |
| VH4 | CTTAAAAGGGGTCCAGTGT (SEQ ID NO: 101) |
| VH5-1 | CAYTTTAAAARGTGTCMAGTGT (SEQ ID NO: 102) |
| VH5-2 | GTTTTAAAAGGTGTCCTGTG (SEQ ID NO: 103) |
| VH6 | CTYTTAAAAGGKGTCCAGWG (SEQ ID NO: 104) |
| VH7-1 | CYTTTAMATGGTATCCAGTGT (SEQ ID NO: 105) |
| VH7-2 | CTTTTACATGGTTTCAAGTGT (SEQ ID NO: 106) |
| VH8 | GTCCCTGCATATGTCYT (SEQ ID NO: 107) |
| VH9 | GATGGCAGCWGCYCAAAG (SEQ ID NO: 108) |
| VH10 | CTATCAAGGTGTGCATTGT (SEQ ID NO: 109) |
| VH11 | CTTTTAAAAGWTGTCCAGKGT (SEQ ID NO: 110) |
| VH12 | GTGACAGTCCTTCCTGGTAG (SEQ ID NO: 111) |
| VH14 | CTTCCTGATGGCAGTGGTT (SEQ ID NO: 112) |
| VH15 | GCTACAGGTATCCAATCC (SEQ ID NO: 113) |

The reverse primer (murine IgG constant) is provided below.

| Name | Sequence |
| --- | --- |
| HC-Rev | GCGTCTAGAAYCTCCACACACAGGRRCCAGTGGATAGAC (SEQ ID NO: 114) |

The forward primers (murine IgKappa leader) are provided below.

| Name | Sequence |
| --- | --- |
| VK1-1 | CTGWTGTTCTGGATTCCTG (SEQ ID NO: 115) |
| VK1-2 | GGTCAGACAGTCAGCAGT (SEQ ID NO: 116) |
| VK2 | GTGCTCTGGATTCGGGAA (SEQ ID NO: 117) |
| VK4/5-1 | CAGCTTCYTGCTAATCAGTG (SEQ ID NO: 118) |
| VK4/5-2 | CTAATCAGTGCTTCAGGA (SEQ ID NO: 119) |
| VK8-1 | GTGGGTATCTGGTRCSTGTG (SEQ ID NO: 120) |
| VK8-2 | GGAAATTTAAAAGTACCTGTGGG (SEQ ID NO: 121) |
| VK9A/9B-1 | GGTTTCMAGGTRCCAGATGT (SEQ ID NO: 122) |
| VK9A/9B-2 | CTCTGGTTYCCAGGTATC (SEQ ID NO: 123) |
| VK10 | CTGTTTTCAAGGTRCCAGATGT (SEQ ID NO: 124) |
| VK11 | GTTGTAATGTCCAGAGGA (SEQ ID NO: 125) |
| VK12/13-1 | CTTACAGGTGCCAGATGT (SEQ ID NO: 126) |
| VK12/13-2 | CTCAATTGTAGRTGCCAGATGT (SEQ ID NO: 127) |
| VK12/13-3 | CACAGTAGGTGTCAGATGT (SEQ ID NO: 128) |
| VK12/13-4 | GTCGTAGTTGTCAGATGT (SEQ ID NO: 129) |
| VK12/13-5 | CCTCCTTCTTGGCCAAGA (SEQ ID NO: 130) |
| VK19/28-1 | CTTATATGGAGCTGATGGG (SEQ ID NO: 131) |
| VK19/28-2 | GTGTCTGGTGCTCATGGG (SEQ ID NO: 132) |
| VK19/28-3 | CTSTGGTTGTCTGGTGTTGA (SEQ ID NO: 133) |
| VK20 | GTCTCTGATTCTAGGGCA (SEQ ID NO: 134) |
| VK21-1 | CTKCKCTGGGTTCCAG (SEQ ID NO: 135) |
| VK21-2 | GCAGGTGTTGACGGA (SEQ ID NO: 136) |
| VK22-1 | CAGGTGCCTCGTGCAC (SEQ ID NO: 137) |
| VK22-2 | CTCTGGTGCCTGTGCA (SEQ ID NO: 138) |
| VK23 | CTGGAYTYCAGCCTCCAGA (SEQ ID NO: 139) |
| VK24/25-1 | GWTCTCTRGAGTCAGTGGG (SEQ ID NO: 140) |
| VK24/25-2 | CTGGATCCCTGGAKCYACT (SEQ ID NO: 141) |
| VK32 | GTTCTGCTTTTTAGGTGTG (SEQ ID NO: 142) |
| VK33/34 | GATCCCAGGCATGATATGT (SEQ ID NO: 143) |
| VK31/38C | CTTCATGGTGCTCAGTGT (SEQ ID NO: 144) |
| VKRF | CCATATCAGGTGCCCAGTGT (SEQ ID NO: 145) |

The reverse primer (murine IgKappa constant) is provided below.

| Name | Sequence |
| --- | --- |
| LC-rev | GCGTCTAGAACTGGATGGTGGGAAGATGG (SEQ ID NO: 146) |

Figure 6:
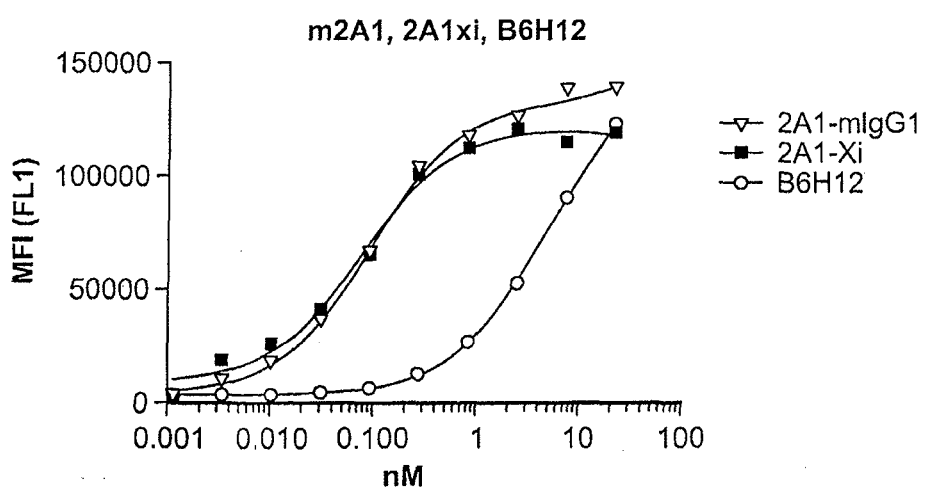
FIG. 6 is a graph depicting the binding of 2A1, 2A1-xi, and B6H12 to Raji cells, as assessed by flow cytometry. Importantly, the graph shows that the variable region sequences of the heavy (VH) and light (VL) chains were correctly elucidated in the chimeric version of 2A 1.

Amplified VH and VL were subsequently cloned in-frame into vectors containing appropriate antibody secretion sequences and human IgG1 and Igkappa constants regions, respectively, to generate murine:human chimeric DNA constructs. These constructs were co-transfected into 293Freestyle cells (Life Technologies) and the resultant antibody was purified from the cell culture supernatant by Protein-A chromatography. To determine that the correct VH and VL sequences had been identified, the chimeric 2A1 (denoted 2A1-xi) was compared to the murine parental 2A1 antibody and CD47 binding assay by flow cytometry on Raji cells (FIG. 6). B6H12 was also included as a positive control in this assay. Bound 2A1-xi was detected using a FITC-conjugated anti-human IgG secondary antibody. Bound 2A1 and B6H12 were detected using a FITC-conjugated anti-mouse IgG secondary antibody. Apparent affinities were determined by non-linear fits (Prism Graphpad Software) of the median fluorescence intensities at various antibody concentrations (Table 2). The 2A1-xi antibody has a similar binding affinity as the murine 2A1 antibody toward cell surface CD47, demonstrating that the VH and VL sequences had been properly identified.

TABLE 2

|          | KD(apparent) (pM) | Std Error | $R^2$  |
|----------|-------------------|-----------|--------|
| 2A1-mIgG1 | 93.6             | ±10.1     | 0.9977 |
| 2A1-xi   | 78                | ±14.9     | 0.9922 |
| B6H12    | 3786              | ±310      | 0.9998 |

Example 8

Antibody Humanization

The murine 2A1 CD47 antibody was humanized to reduce the potential of immunogenicity when administered to human patient. The sequences of the VH and VL region of 2A1 were compared to human antibody sequences in the IMGT databank. Subsequently, a structural model was generated of the 2A1 VH and VL regions using the known structures of the most closely related humanized and human antibodies in the Protein Data Bank (PDB). The 3 complementary determining regions (CDR) in both the heavy and light chains of the 2A1 antibody were fixed and the murine frameworks were replaced with numerous human frameworks that had the highest possibility of maintaining the proper orientation of the CDRs. Constructs corresponding to each the humanized 2A1 variants were generated by gene synthesis and cloned in frame into vectors containing an appropriate secretion sequence and human IgG1 and Igkappa constant regions. Various combinations of humanized heavy and light chains were co-transfected in to 293Freestyle cells (Life Technologies), and resultant antibodies were purified from the cell culture supernatant by Protein-A chromatography.

Humanized antibodies were tested for their ability to bind Raji cells by flow cytometry (FIG. 7). The 2A1-xi antibody was used as a control in most of these assays to set the benchmark for binding affinity. Humanized antibodies were further optimized to enhance expression and reduce problematic sites including potential isomerization and deamidation sites. An example of an optimized humanized antibody derived from the murine 2A1 antibody is denoted as AB6.12 antibody, which displays very similar binding affinity as the 2A1-xi antibody (FIG. 7H; Table 3). Apparent affinities were determined by non-linear fits (Prism Graphpad Software) of the median fluorescence intensities at various antibody concentrations.

TABLE 3

|         | KD(apparent) (pM) | Std Error | $R^2$  |
|---------|-------------------|-----------|--------|
| 2A1-xi  | 36.4              | ±8.54     | 0.9908 |
| AB6.12  | 39.9              | ±5.54     | 0.9964 |

The AB6.12 antibody was subsequently converted from an IgG1 to other human IgG isotypes by replacing the constant domain of the heavy chain. As shown in FIG. 7I, changing the IgG isotype to a hinge stabilized version of IgG4 (IgG4P: S228P), and reduced Fc receptor binding variant of the hinge stabilized IgG4 (IgG4PE: S228P/L235E) did not alter binding affinity of the humanized antibody toward cells surface CD47 (FIG. 7I; Table 4). Apparent affinities were determined by non-linear fits (Prism Graphpad Software) of the median fluorescence intensities at various antibody concentrations.

TABLE 4

|              | KD(apparent) (pM) | Std Error | $R^2$  |
|--------------|-------------------|-----------|--------|
| AB6.12-IgG1  | 38.6              | ±10.5     | 0.9798 |
| AB6.12-IgG4P | 35.7              | ±8.4      | 0.9841 |
| AB6.12-IgG4PE| 34.6              | ±10.9     | 0.9727 |

Throughout the humanization process, the CD47 antibodies were tested to ensure the SIRPα blocking functionality was intact. As shown in FIG. 7J, multiple IgG isotypes of the humanized antibody, AB6.12, blocked the SIRPα:CD47 interaction, using the flow cytometry-based method described above in Example 3. Exemplary CD47 antibodies and their corresponding VH region and VL region include those provided in Table 1.

During the humanization process, it was determined that in some embodiments, an amino acid sequence motif, "NA," at the beginning of VH CDR3 (SEQ ID NO: 52 or SEQ ID NO: 77) is important for binding of the CD47 antibodies described herein. In some embodiments, in the absence of amino acid residues "NA" at the beginning of VH CDR3 (SEQ ID NO: 52 or SEQ ID NO: 77), the CD47 antibodies of the invention do not bind to their target or bind to their target with lower affinity than they would in the presence of amino acid residues "NA." For example, when the "NA" motif was changed to more canonical motifs of "AR" or "AT," binding was substantially reduced (i.e., greater than ten-fold). In other embodiments, in the absence of amino acid residues "NA" at the beginning of VH CDR3 (SEQ ID NO: 52 or SEQ ID NO: 77), the CD47 antibodies of the invention bind to their target with equivalent affinity compared to binding in the presence of amino acid residues "NA."

Those skilled in the art will recognize that it is possible to determine, without undue experimentation, if an amino acid substitution in the sequences of the CD47 antibodies of the invention will result in an antibody with substantially the same function, e.g., a CD47 antibody with the ability to block SIRPα and not cause a significant level of hemagglutination.

Figure 8B:
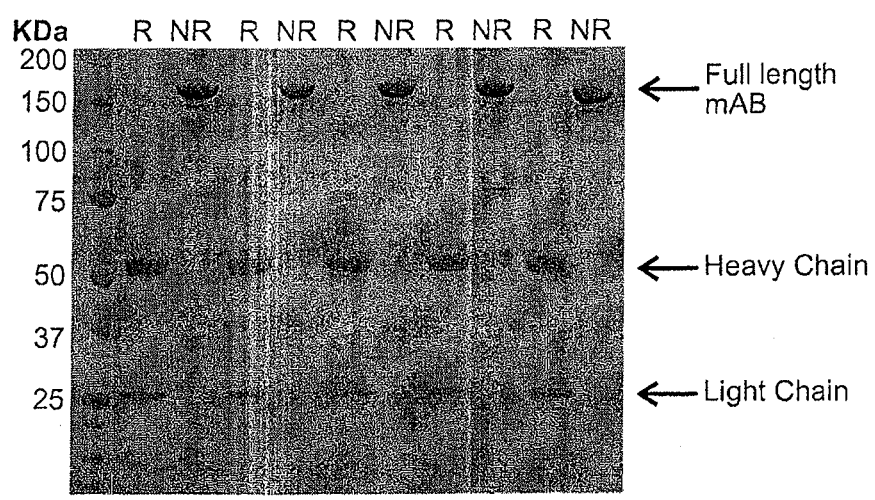
FIG. 8B is a photograph of a coomassie blue stained SDS-PAGE gel of numerous humanized variants of 2A1 under reducing (R) and non-reducing (NR) conditions.

An image of the trace from size exclusion chromatography using an AKTA FLPC with a superdex200 column is shown in FIG. 8A. The IgG1, IgG4P, and IgGPE variants of the AB6.12 antibody are shown. All three variant are over 98% monomeric. FIG. 8B is a photograph of a coomassie blue stained SDS-PAGE gel of numerous humanized variants of 2A1 under reducing (R) and non-reducing (NR) conditions.

Example 9

CD47 Antibodies Promote Phagocytosis of Tumor Cell Lines

CD47 is a cell surface receptor that is upregulated on tumor cells and is also thought to contribute to immune evasion through its interaction with its natural ligand SIRPα. Ligation of CD47 to SIRPα on macrophages results in decreased phagocytic activity. As described in detail below, it was determined if the CD47 binding and SIRPα blocking activity of the 2A1 antibody, and variations thereof, promote tumor cell phagocytosis in the presence of human macrophages.

PBMCs were isolated from human blood, and the monocytes were differentiated into macrophages by incubating them in AIM-V media (Life Technologies) for 7 days. These monocyte derived macrophages (MDMs) become adherent allowing other cells to be washed away. MDMs were scraped and re-plated in 12-well dishes and allowed to adhere for 24 hours. The human tumor cell line CCRF-CEM was chosen as a target cell type because of its high CD47 expression. CCRF-CEM cells were labeled with 0.3 µM CFSE at 37° C. for 15 minutes, then washed and added to MDMs at a ratio of 4:1 tumor cells per phagocyte, and CD47 antibody was added at various concentrations. Phagocytosis of target cells was allowed for 3 hours. Subsequently, non-phagocytosed target cells were washed away with PBS. The remaining phagocytes were scraped off, stained with an antibody to the macrophage marker CD14 conjugated to DyLite 649 (Biolegend), and analyzed by flow cytometry. Phagocytosis was measured by gating on live cells that were FL4 positive (CD14+), and then assessing the percent of FL1 (CFSE+) positive cells.

Figure 9A:
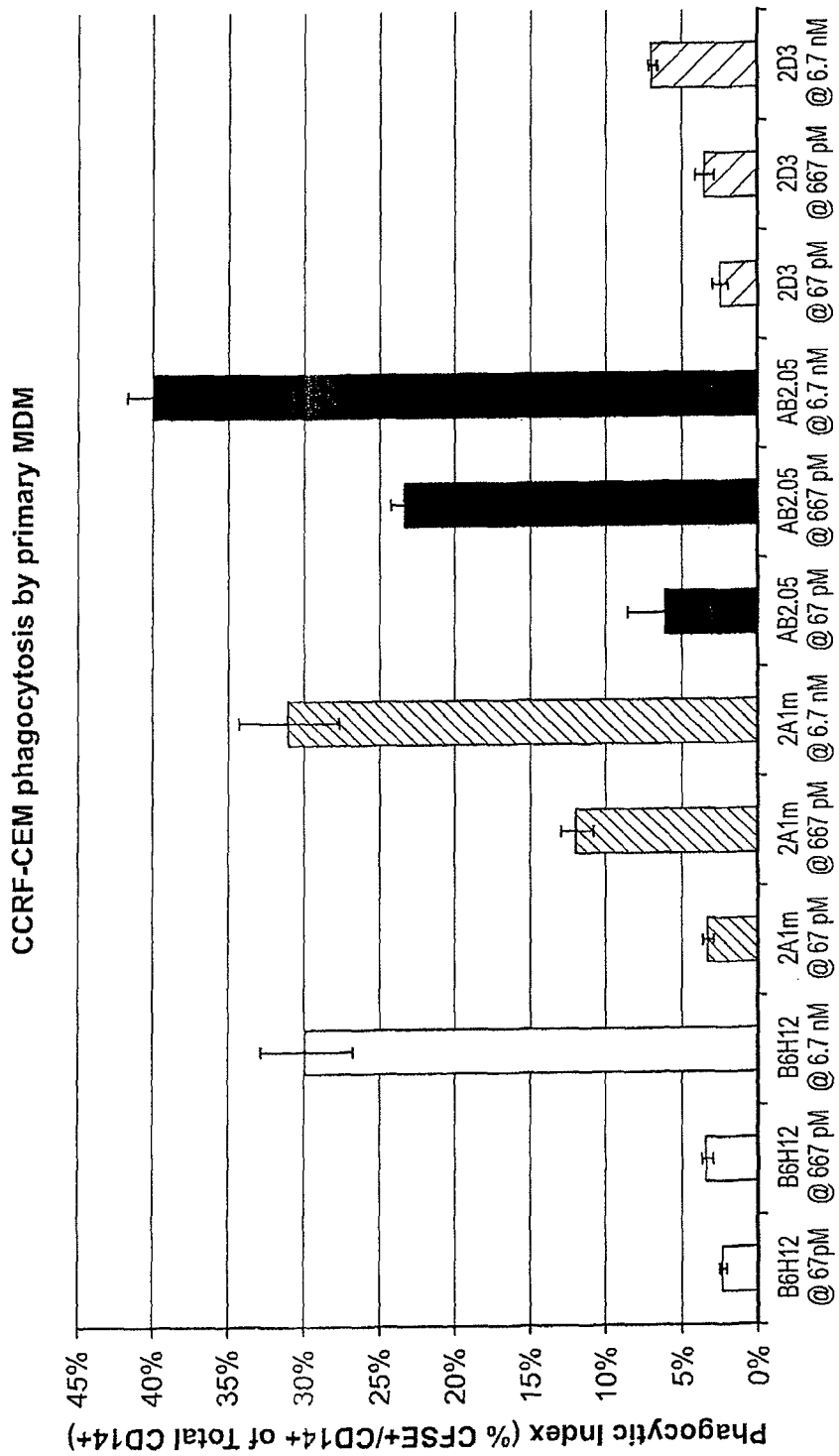
FIG. 9A is a graph showing the phagocytic index, wherein antibodies used were the commercial antibody B6H12, the murine 2A1 antibody, a humanized variant AB2.05 antibody, and the non-blocking commercial antibody 2D3.
Figure 9B:
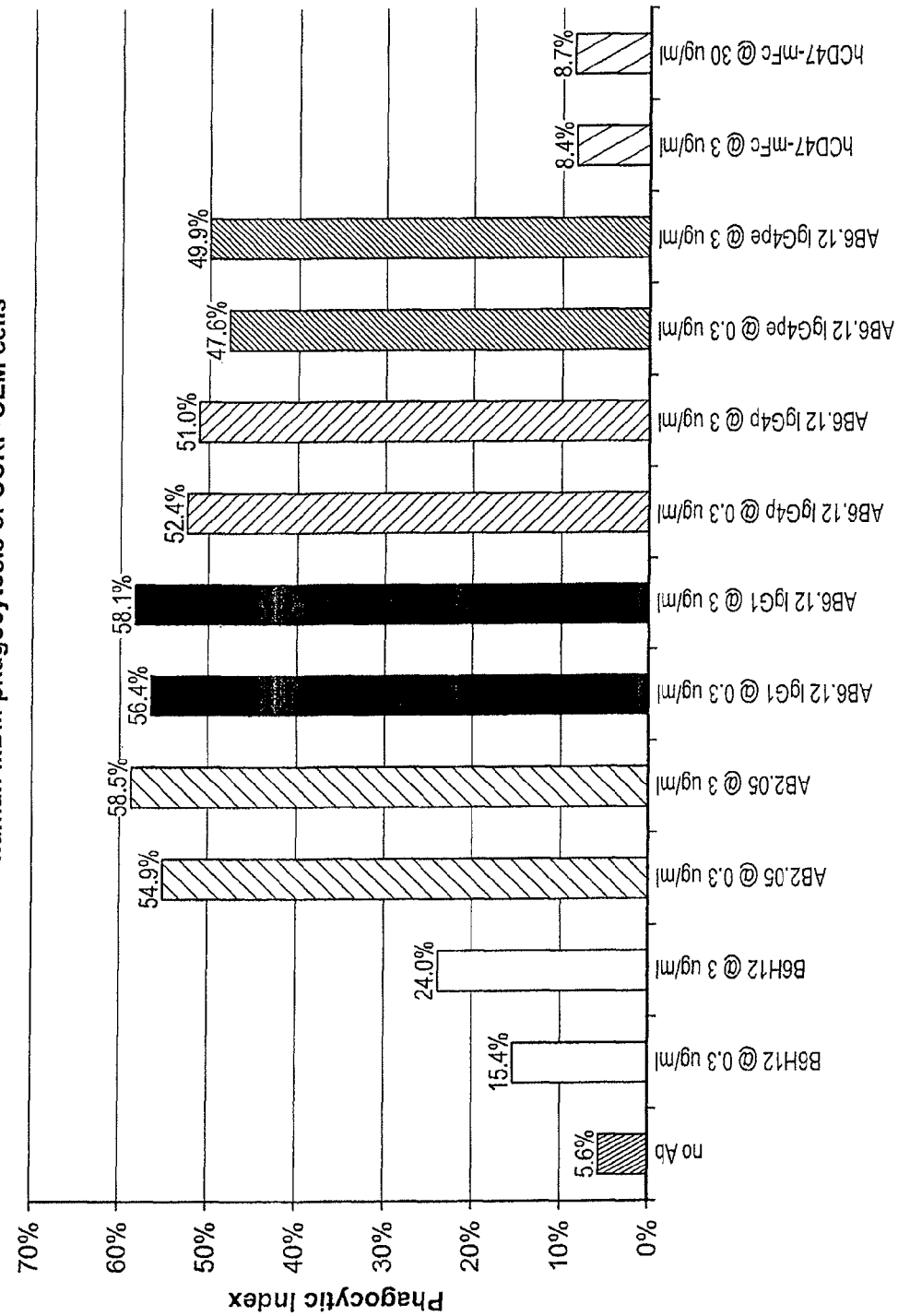
FIG. 9B is a graph showing the phagocytic index, wherein the antibodies used were the commercial antibody B6H12, humanized antibody AB2.05 (human IgG1), and the IgG1, IgG4P, and IgG4PE variants of the humanized antibody AB6.12. CCRF-CEM cells were used as the CD47 target cell line in these experiments.

FIG. 9 shows that the CD47 antibody 2A1 and its humanized variants demonstrated a dose-dependent increase in phagocytosis of tumor cells by MDMs. Antibody 2A1 and the humanized variant AB2.05 were unique in their ability to induce phagocytosis of tumor cells at 66.7 µM, whereas B6H12 had no activity at that concentration (FIG. 9A). FIG. 9B shows how 2A1, and the humanized variants AB2.05, AB6.12-IgG1, AB6.12-IgG4P, and AB6.12-IgG4PE all induce maximal phagocytosis at 0.3 µg/ml or 2 nM, while B6H12 requires higher concentrations. This data demonstrates that the CD47 antibody, 2A1 (and humanized variants derived from it), induce macrophage-mediated phagocytosis of CD47 positive tumor cells. In this example, CCFR-CEM cells were utilized as the CD47 positive target cell.

Example 10

Antitumor Activity of CD47 Antibodies

The anti-tumor activity of the murine CD47 antibodies was evaluated in a Raji model of lymphoma. Raji cells were implanted subcutaneously in NOD/SCID mice, and randomized into 5 groups (10 mice per group, day 0). Group 1: Vehicle (buffer only); Group 2: B6H12 (positive control); Group 3: 1B4; Group 4: 2A1; and Group 5: 9E4. Treatment with each antibody or vehicle (buffer only) began when tumors were palpable (50 mm³, day 13) and mice were euthanized when their tumor volumes reached ~1500 mm³. Tumor volumes were measured 3 times per week. Antibodies were dosed intravenously (IV) with 200 µg 3 times per week for 3 weeks (9 total doses per mouse). Treatment started on day 13 and ended on day 32.

Figure 10A:
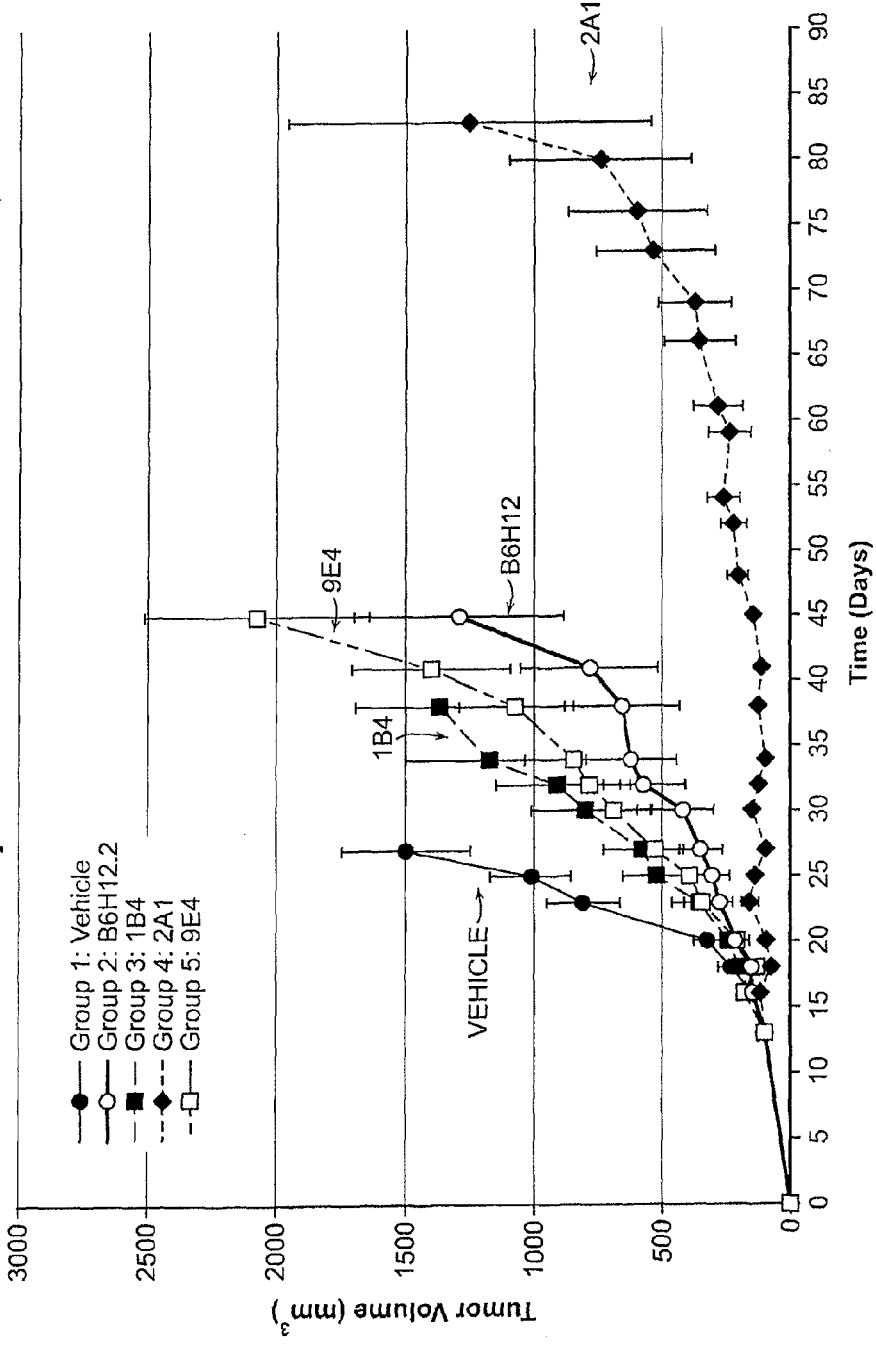
FIG. 10A is a graph that shows the efficacy of the murine antibodies 9E4, 1B4, 2A1, and the commercial antibody B6H12.

As shown in FIG. 10A, CD47 antibodies of the invention, particularly the 2A1 antibody, demonstrated anti-tumor activity in this animal model of lymphoma. To reach a tumor volume of 1500 mm³, Group 1 (vehicle only) required ~25 days; Group 2 (B6H12.2) required ~45 days; Group 3 (1B4) required ~37 days; Group 4 (2A1) required ~85 days; and Group 5 (9E4) required ~40 days to reach a tumor volume ~1500 mm³. These data indicate that antibody 2A1 was significantly more potent than all CD47 binding antibodies tested, including B6H12 that was known to bind CD47, block CD47 interaction with SIRPα, and suppress tumor formation in mouse models of human cancer. Unexpectedly, tumor suppression activity of these CD47 antibodies did not correlate with their potency of binding CD47 or blocking CD47 interaction with SIRPα, which would be expected based upon published data.

As described in Examples 2 and 3, 2A1, 1B4, and 9E4 had similar affinity for CD47 and similar potency for blocking CD47 interaction with SIRPα. In addition, the enhanced efficacy of 2A1 cannot be explained by differences in the Fc domain of the antibodies described since all antibodies used in this study were comprised of identical mouse IgG1 domains. Thus, in addition to unique composition of matter, the 2A1 antibody possesses unexpected and unique characteristics including the inability to induce homotypic interactions between CD47 expressing cells, e.g., red blood cells, and enhanced tumor suppression activity that cannot be explained by enhanced binding to CD47 or an enhanced ability to block CD47 interaction with SIRPα.

Figure 10B:
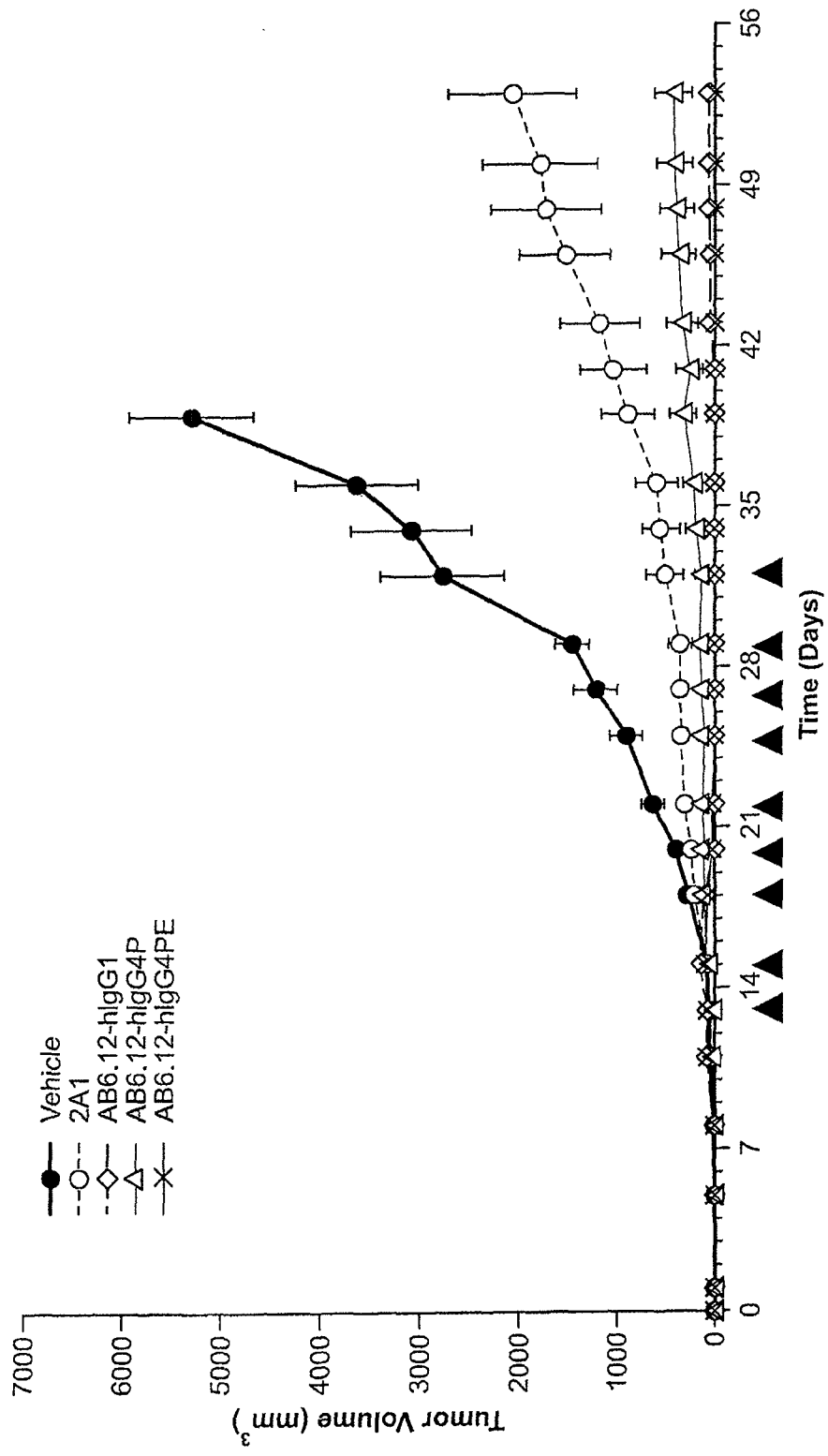
FIG. 10B is a graph that shows the efficacy of the IgG1, IgG4P, and IgG4PE isotypes of the humanized antibody AB6.12, along with the murine 2A1 antibody. In both models, mice were treated with 200 µg antibody doses three times a week.

To confirm that the humanized 2A1 antibodies maintained their anti-tumor activity, a similar Raji tumor study was conducted. The study design was the same as described above. Raji cells were implanted subcutaneously in NOD/SCID mice and randomized into 5 groups (10 mice per group, day 0). In this study, antibodies were dosed intraperitoneal (IP) with 200 µg 3 times per week for 3 weeks (9 total doses per mouse), and tumor volumes were measured 3 times per week. However, for this study, the mouse IgG1 2A1 antibody (group 2) was compared to a humanized derivative, AB6.12. For this study, AB6.12 was constructed (as described in EXAMPLE 8) into human IgG1 (Group 3), human IgG4P (Group 4) and human IgG4PE (Group 4). Thus, this experiment was designed to address the influence of 2A1 humanization on its tumor suppression activity and the potential role of Fc domain effector function that is known in the art to contribute to the antitumor activities of many antibodies. It has been well documented that human IgG1 possesses significantly more effector function compared to human IgG4P. IgG4PE was developed to further reduce effector function. As can be seen in FIG. 10B, humanization of 2A1 did not diminish the antitumor activity of 2A1, and in fact may have enhanced it. AB6.12-hIgG1, AB6.12-hIgG4P, and AB6.12-hIgG4PE all showed similar anti-tumor activity that appears significantly greater than mouse 2A1 (2A1mIgG). This result is unexpected since 2A1mIgG1, AB6.12-hIgG1, AB6.12-hIgG4P and AB6.12-hIgG4PE have similar CD47 binding and SIRPα blocking activities. In addition, since AB6.12-hIgG1, AB6.12-hIgG4P and AB6.12-hIgG4PE have similar anti-tumor activities, it appears that effector function does play a role in the efficacy of the humanized 2A1 antibody AB6.12.

Example 11

Co-Crystallization of CD47 Antibodies with CD47

CD47 is 5 pass transmembrane protein with a single extracellular IgV (immunoglobin-like variable-type) domain that is highly glycosylated at 6 sites. The structure of the CD47-IgV domain has been solved in complex with the IgV domain of SIRPα, its natural ligand (Protein Data Bank (PDB) Reference No. 2JJS; Hatherley et al., 2008 Mol Cell, 25; 31(2): 266-77 (FIG. 11A)). The structure shows SIRPα-IgV binding to CD47-IgV on an apical epitope including the N-terminal pyroglutamate of CD47. This structure sufficiently explains how both cell surface transmembrane proteins can productively interact from adjacent cells in a head to head orientation. The X-ray crystallographic structure of CD47-IgV in complex with the B6H12Fab is presented in FIG. 11B. For clarity, the constant regions of the Fab (CH1 and CL) were omitted in the Figure, and only the Fv (VH and VL) is presented. This revealed an apical binding site, positioning this antibody on a surface extremely distal from the cell membrane (FIG. 11B). The mechanism of SIRPα blocking by B6H12 is apparent from this structure. The orientation purposes relative location of the cell membrane is depicted as a dashed line in FIG. 11.

In order to determine the target epitope of the antibodies of the present invention, the X-ray crystallographic structure of the co-complex of CD47-IgV domain and the Fab of 2A1-xi (chimeric antibody with human CH1 and CL domains) was determined (FIG. 11C). For clarity, the constant regions of the Fab (CH1 and CL) were omitted in the Figure, and only the Fv (VH and VL) is presented. Unlike the previously determined structure of CD47 binding SIRPα in a head to head orientation (FIG. 11A), and the B6H12 antibody being positioned apically away from the membrane (FIG. 11B), the structure of 2A1 in complex with CD47 revealed binding of the antibody to CD47 near the membrane in an unexpected and unique head to side orientation (FIG. 11C). The 2A1 epitope on CD47 is discontinuous, and includes residues Y37, K39, K41, the KGRD (SEQ ID NO: 56) loop (residues 43-46), D51, H90, N93, E97, T99, E104, and E106 of CD47 when numbered in accordance with SEQ ID NO: 147 (i.e., SEQ ID NO: 48 excluding the signal sequence (amino acids 1-18)). The structure of 2A1 bound to CD47 also reveals that the VH is primarily involved in binding to the KGRD (SEQ ID NO: 56) loop of CD47, while the VK domain interacts with apical residues including Y37, T102, and E104, which are involved in SIRPα binding. Therefore, it is primarily the VK domain that physically precludes SIRPα binding to CD47. These structural studies suggest that the unique epitope which 2A1 binds to is on the side of CD47. In contrast to CD47 antibodies known in the art, the orientation of the 2A1 VH region in a membrane proximal position are critical features of this antibody that prevent a significant level of red blood cell hemagglutination by constraining the antibody such that it cannot bridge to CD47 molecules on adjacent cells.

---

What is claimed is:

1. An isolated monoclonal antibody or immunologically active fragment thereof that binds to human CD47, said antibody or immunologically active fragment thereof comprising:

a variable heavy (VH) chain CDR1 amino acid sequence set forth in SEQ ID NO: 50, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 66;

a VH chain CDR2 amino acid sequence set forth in SEQ ID NO: 51, SEQ ID NO: 72, SEQ ID NO: 73, SEQ ID NO: 74, SEQ ID NO: 75, or SEQ ID NO: 76;

a VH chain CDR3 amino acid sequence set forth in SEQ ID NO: 52 or SEQ ID NO: 77;

a variable light (VL) chain CDR1 amino acid sequence set forth in SEQ ID NO: 53, SEQ ID NO: 67, or SEQ ID NO: 68;

a VL chain CDR2 amino acid sequence set forth in SEQ ID NO: 54, SEQ ID NO: 69, SEQ ID NO: 70, or SEQ ID NO: 71; and a VL CDR3 sequence set forth in SEQ ID NO: 55.

2. The antibody or immunologically active fragment thereof of claim 1, wherein the antibody is chimeric or humanized.

3. The antibody or immunologically active fragment thereof of claim 1, wherein the antibody or immunologically active fragment thereof prevents the human CD47 from interacting with signal-regulatory-protein α (SIRPα).

4. The antibody or immunologically active fragment thereof of claim 3, wherein the antibody or immunologically active fragment thereof promotes macrophage-mediated phagocytosis of a CD47-expressing cell.

5. The antibody or immunologically active fragment thereof of claim 1, wherein the antibody or immunologically active fragment thereof is of an IgG isotype selected from the group consisting of IgG1 isotype, IgG2 isotype, IgG3 isotype, and IgG4 isotype.

6. The antibody or immunologically active fragment thereof of claim 1, wherein the antibody or immunologically active fragment thereof comprises a variable heavy (VH) chain region sequence selected from the group consisting of SEQ ID NOs: 5-30.

7. The antibody or immunologically active fragment thereof of claim 1, wherein the antibody or immunologically active fragment thereof comprises a variable light (VL) chain region sequence selected from the group consisting of SEQ ID NOs: 31-47.

8. The antibody or immunologically active fragment thereof of claim 1, wherein the antibody or immunologically active fragment thereof comprises a VH region sequence provided in any one of SEQ ID NOs: 5-30 and a VL region sequence provided in any one of SEQ ID NOs: 31-47.

9. The antibody or immunologically active fragment thereof of claim 8, wherein the antibody or immunologically active fragment thereof comprises a VH region sequence provided in any one of SEQ ID NOs: 5, 7, 8, 11, 12, 15-17, 20-22, and 27-30 and a VL region sequence provided in any one of SEQ ID NOs: 31, 32, 35, 40, 41, 42, 43, 44, and 47.

10. The antibody or immunologically active fragment thereof of claim 8, wherein the antibody comprises a combination of a VH chain region sequence and a VL chain region sequence, said combination selected from the combinations listed in Table 1.

11. The antibody or immunologically active fragment thereof of claim 1, wherein the antibody or immunologically active fragment thereof comprises the VH CDR1 sequence set forth in SEQ ID NO: 50, the VH CDR2 sequence set forth in SEQ ID NO: 51, the VH CDR3 sequence set forth in SEQ ID NO: 52, the VL CDR1 sequence set forth in SEQ ID NO: 53, the VL CDR2 sequence set forth in SEQ ID NO: 54, and the VL CDR3 sequence set forth in SEQ ID NO: 55.

12. The antibody or immunologically active fragment thereof of claim 1, wherein the antibody or immunologically active fragment thereof comprises the VH CDR1 sequence set forth in SEQ ID NO: 50, the VH CDR2 sequence set forth in SEQ ID NO: 72, the VH CDR3 sequence set forth in SEQ ID NO: 52, the VL CDR1 sequence set forth in SEQ ID NO: 53, the VL CDR2 sequence set forth in SEQ ID NO: 71, and the VL CDR3 sequence set forth in SEQ ID NO: 55.

13. The antibody or immunologically active fragment thereof of claim 1, wherein the antibody binds to CD47 in a head to side orientation, wherein a VH chain of the antibody is positioned near the membrane of a CD47 expressing cell, and wherein a VL chain of the antibody occludes a SIRPα binding site on CD47.

14. The antibody or immunologically active fragment thereof of claim 1, wherein the antibody binds to a discontinuous epitope on CD47.

15. The antibody or immunologically active fragment thereof of claim 14, wherein the antibody binds to a CD47 loop comprising SEQ ID NO: 56.

16. The antibody or immunologically active fragment thereof of claim 14, wherein the discontinuous epitope comprises amino acid residues Y37, K39, K41, K43, G44, R45, D46, D51, H90, N93, E97, T99, E104, or E106 of CD47 when numbered in accordance with SEQ ID NO: 147.

17. The antibody or immunologically active fragment thereof of claim 1, wherein the antibody does not cause a significant level of hemagglutination of red blood cells, as measured by an in vitro hemagglutination assay.

18. The antibody or immunologically active fragment thereof of claim 1, wherein the antibody or immunologically active fragment thereof is of an IgG isotype selected from IgG4P and IgGPE.

19. A pharmaceutical composition comprising the antibody or immunologically active fragment thereof of claim 1 and a carrier.

20. An isolated monoclonal antibody or immunologically active fragment thereof that binds to human CD47, said antibody or immunologically active fragment thereof comprising:
 a VH CDR1, a VH CDR2, and a VH CDR3, respectively comprising the amino acid sequences of a CDR1, a CDR2, and a CDR3 within a VH chain region having the sequence set forth in any of SEQ ID NOs: 5-30; and
 a VL CDR1, a VL CDR2, and a VLCDR3, respectively comprising the amino acid sequences of a CDR1, a CDR2, and a CDR3 within a VL chain region having the sequence set forth in any of SEQ ID NOs: 31-47.

21. A pharmaceutical composition comprising the antibody or immunologically active fragment thereof of claim 20.

* * * * *

UNITED STATES PATENT AND TRADEMARK OFFICE
CERTIFICATE OF CORRECTION

| | | |
|---|---|---|
| PATENT NO. | : 9,045,541 B2 | Page 1 of 1 |
| APPLICATION NO. | : 13/761087 | |
| DATED | : June 2, 2015 | |
| INVENTOR(S) | : Brendan Eckelman et al. | |

It is certified that error appears in the above-identified patent and that said Letters Patent is hereby corrected as shown below:

In the Specification:

Column 11, line 28, please replace "IgGPE" with --IgG4PE--;

Column 12, line 66, please replace "IgG1, IgG4P, and IgGPE variants" with --IgG1, IgG4P, and IgG4PE variants--;

Column 62, line 53, please replace "IgG1, IgG4P and IgGPE variants" with --IgG1, IgG4P, and IgG4PE variants--.

In the Claims:

Column 148, claim number 18, line number 28, please replace "IgG4P and IgGPE" with --IgG4P and IgG4PE--.

Signed and Sealed this
Seventh Day of June, 2016

Michelle K. Lee
*Director of the United States Patent and Trademark Office*

SEQUENCE LISTING

<160> NUMBER OF SEQ ID NOS: 147

<210> SEQ ID NO 1
<211> LENGTH: 330
<212> TYPE: PRT
<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

```
            275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
            325

<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Pro Cys Pro Arg
        115                 120                 125
Cys Pro Glu Pro Lys Ser Cys Asp Thr Pro Pro Pro Cys Pro Arg Cys
    130                 135                 140
Pro Glu Pro Lys Ser Cys Asp Thr Pro Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
        195                 200                 205
Val Asp Gly Val Glu Val His Asn Ala Lys Thr Lys Pro Arg Glu Glu
    210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
```

```
Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 4
<211> LENGTH: 327
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly Lys
            325

<210> SEQ ID NO 5
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 5

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Gly Trp Ile Asp Pro Asp Asn Gly Asp Thr Glu Phe Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Ala Tyr Gly Ser Ser Tyr Pro Met Asp Tyr Trp Gly Gln
            100                 105                 110

Gly Thr Ser Val Thr Val
        115

<210> SEQ ID NO 6
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 6

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
            20                  25                  30

Tyr Leu His Trp Val Gln Gln Ala Pro Gly Lys Gly Leu Glu Trp Met
        35                  40                  45

Gly Trp Ile Asp Pro Asp Asn Gly Asp Thr Glu Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 7
<211> LENGTH: 118
<212> TYPE: PRT
<213> ORGANISM: Artificial Sequence

```
<220> FEATURE:
<223> OTHER INFORMATION: Variable heavy chain region of a humanized CD47
      antibody

<400> SEQUENCE: 7

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
            115

<210> SEQ ID NO 8
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 8

Glu Val Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
            115

<210> SEQ ID NO 9
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 9

Gln Met Gln Leu Val Gln Ser Gly Ala Glu Val Lys Lys Thr Gly Ser
1               5                   10                  15
```

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Gly Arg Val Thr Met Thr Ala Asp Thr Ser Asn Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 10
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 10

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 11
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 11

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Gln Gly Asp Thr Glu Tyr Ala Gln Lys Phe
    50                  55                  60

```
Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
            115

<210> SEQ ID NO 12
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 12

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Tyr Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
            115

<210> SEQ ID NO 13
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 13

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Ser Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110
```

Gly Thr Thr Val Thr Val
        115

<210> SEQ ID NO 14
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 14

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Ala Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 15
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 15

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Thr Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 16
<211> LENGTH: 118
<212> TYPE: PRT
<213> ORGANISM: Artificial Sequence
<220> FEATURE:

<223> OTHER INFORMATION: Variable heavy chain region of a humanized CD47
      antibody

<400> SEQUENCE: 16

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Pro Tyr Pro Met Asp Tyr Trp Gly Gln
            100                 105                 110

Gly Thr Thr Val Thr Val
        115

<210> SEQ ID NO 17
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 17

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 18
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 18

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Thr Tyr Tyr

```
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 19
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 19

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Asn Phe Thr Tyr Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 20
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 20

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Ile Thr Tyr Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
```

```
                65                  70                  75                  80
Met Glu Leu Ser Ser Leu Arg Ser Glu Asp Thr Ala Met Tyr Tyr Cys
                    85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 21
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 21

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Lys Tyr Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 22
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 22

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
```

-continued

```
                115

<210> SEQ ID NO 23
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 23

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Thr Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 24
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 24

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Ile Thr Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 25
<211> LENGTH: 118
<212> TYPE: PRT
<213> ORGANISM: Artificial Sequence
<220> FEATURE:
<223> OTHER INFORMATION: Variable heavy chain region of a humanized CD47
``` antibody

<400> SEQUENCE: 25

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 26
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 26

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 27
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 27

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

-continued

```
Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
 50                  55                  60

Gln Asp Arg Val Thr Ile Thr Arg Asp Arg Ser Met Ser Thr Ala Tyr
65                  70                  75                  80

Leu Gln Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 28
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 28

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
 50                  55                  60

Gln Asp Arg Val Thr Ile Thr Arg Asp Arg Ser Met Ser Thr Ala Tyr
65                  70                  75                  80

Met Glu Leu Ser Ser Leu Thr Ser Glu Asp Thr Ala Val Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 29
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 29

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
 50                  55                  60

Gln Asp Arg Val Thr Ile Thr Arg Asp Arg Ser Met Ser Thr Ala Tyr
65                  70                  75                  80
```

```
Met Glu Leu Ser Ser Leu Arg Ser Glu Asp Thr Ala Met Tyr Tyr Cys
            85                  90                  95

Asn Ala Ala Tyr Gly Ser Ser Tyr Pro Met Asp Tyr Trp Gly Gln
            100                 105                 110

Gly Thr Thr Val Thr Val
            115

<210> SEQ ID NO 30
<211> LENGTH: 118
<212> TYPE: PRT
<213> ORGANISM: Artificial Sequence
<220> FEATURE:
<223> OTHER INFORMATION: Variable heavy chain region of a humanized CD47
      antibody

<400> SEQUENCE: 30

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
            20                  25                  30

Tyr Leu His Trp Val Gln Gln Ala Pro Gly Lys Gly Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
            85                  90                  95

Asn Ala Ala Tyr Gly Ser Ser Tyr Pro Met Asp Tyr Trp Gly Gln
            100                 105                 110

Gly Thr Thr Val Thr Val
            115

<210> SEQ ID NO 31
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 31

Asp Ile Lys Met Thr Gln Ser Pro Ser Ser Leu Tyr Ala Ser Leu Gly
1               5                   10                  15

Glu Arg Val Thr Ile Thr Cys Lys Ala Ser Gln Asp Ile His Arg Tyr
            20                  25                  30

Leu Ser Trp Phe Gln Gln Lys Pro Gly Lys Ser Pro Lys Ile Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
            85                  90                  95

Thr Phe Gly Gly Gly Thr Lys Leu Glu Met Lys
            100                 105

<210> SEQ ID NO 32
```

```
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 32

Asp Ile Lys Met Thr Gln Ser Pro Ser Ser Leu Tyr Ala Ser Leu Gly
1               5                   10                  15

Glu Arg Val Thr Ile Thr Cys Lys Ala Ser Gln Asp Ile His Arg Tyr
            20                  25                  30

Leu Ser Trp Phe Gln Gln Lys Pro Gly Lys Ser Pro Lys Ile Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Arg Tyr
            20                  25                  30
```

```
Leu Ser Trp Phe Gln Gln Lys Pro Gly Lys Ala Pro Lys Ser Leu Ile
            35                  40                  45

Tyr Arg Ala Asn Arg Leu Val Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                 85                  90                  95

Thr Phe Gly Gly Gly Thr Lys Val Glu Ile Lys
            100                 105
```

<210> SEQ ID NO 35
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 35

```
Asn Ile Gln Met Thr Gln Ser Pro Ser Ala Met Ser Ala Ser Val Gly
 1               5                  10                  15

Asp Arg Val Thr Ile Thr Cys Lys Ala Ser Gln Asp Ile His Arg Tyr
                 20                  25                  30

Leu Ser Trp Phe Gln Gln Lys Pro Gly Lys Val Pro Lys His Leu Ile
            35                  40                  45

Tyr Arg Ala Asn Arg Leu Val Asp Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                 85                  90                  95

Thr Phe Gly Gly Gly Thr Lys Val Glu Ile Lys
            100                 105
```

<210> SEQ ID NO 36
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 36

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile His Arg Tyr
                 20                  25                  30

Leu Ser Trp Tyr Gln Gln Lys Pro Gly Lys Ala Pro Lys Arg Leu Ile
            35                  40                  45

Tyr Arg Ala Asn Arg Leu Val Asp Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                 85                  90                  95

Thr Phe Gly Gly Gly Thr Lys Val Glu Ile Lys
            100                 105
```

<210> SEQ ID NO 37
<211> LENGTH: 107
<212> TYPE: PRT
<213> ORGANISM: Artificial Sequence
<220> FEATURE:
<223> OTHER INFORMATION: Variable light chain region of a humanized CD47 antibody

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Arg Tyr
            20                  25                  30

Leu Ala Trp Tyr Gln Gln Lys Pro Gly Lys Val Pro Lys Leu Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 38
<211> LENGTH: 107
<212> TYPE: PRT
<213> ORGANISM: Artificial Sequence
<220> FEATURE:
<223> OTHER INFORMATION: Variable light chain region of a humanized CD47 antibody

<400> SEQUENCE: 38

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile His Arg Tyr
            20                  25                  30

Leu Ala Trp Tyr Gln Gln Lys Pro Gly Gln Ala Pro Arg Leu Leu Ile
        35                  40                  45

Tyr Arg Ala Asn Arg Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Tyr Asp Glu Phe Pro Tyr
                85                  90                  95

Thr Gly Phe Gln Gly Thr Arg Leu Glu Ile Lys
            100                 105
```

<210> SEQ ID NO 39
<211> LENGTH: 107
<212> TYPE: PRT
<213> ORGANISM: Artificial Sequence
<220> FEATURE:
<223> OTHER INFORMATION: Variable light chain region of a humanized CD47 antibody

<400> SEQUENCE: 39

```
Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
```

```
                    20                  25                  30

Leu Ser Trp Phe Gln Gln Lys Pro Gly Lys Val Pro Lys His Leu Ile
        35                  40                  45

Tyr Arg Ala Asn Arg Leu Val Asp Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 40

Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Asp Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 41

Asn Ile Gln Met Thr Gln Ser Pro Ser Ala Met Ser Ala Ser Val Gly
 1               5                  10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys Ile Leu Ile
        35                  40                  45

Tyr Arg Ala Asn Arg Leu Val Asp Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
```

```
                100              105

<210> SEQ ID NO 42
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 42

Asn Ile Gln Met Thr Gln Ser Pro Ser Ala Met Ser Ala Ser Val Gly
1               5                  10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 43

Asn Ile Gln Met Thr Gln Ser Pro Ser Ala Met Ser Ala Ser Val Gly
1               5                  10                  15

Asp Arg Val Thr Ile Thr Cys Arg Ala Arg Gln Gly Ile His Arg Tyr
            20                  25                  30

Leu Ser Trp Phe Gln Gln Lys Pro Gly Lys Val Pro Lys Ile Leu Ile
        35                  40                  45

Tyr Arg Ala Asn Arg Leu Val Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 44

Asn Ile Gln Met Thr Gln Ser Pro Ser Ala Met Ser Ala Ser Val Gly
1               5                  10                  15
```

Asp Arg Val Thr Ile Thr Cys Arg Ala Arg Gln Gly Ile His Arg Tyr
                20                  25                  30

Leu Ser Trp Phe Gln Gln Lys Pro Gly Lys Val Pro Lys His Leu Ile
            35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
                100                 105

<210> SEQ ID NO 45
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 45

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
                20                  25                  30

Leu Ser Trp Phe Gln Gln Lys Pro Gly Lys Val Pro Lys Leu Leu Ile
            35                  40                  45

Tyr Arg Ala Asn Arg Leu Val Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
                100                 105

<210> SEQ ID NO 46
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 46

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
                20                  25                  30

Leu Ser Trp Phe Gln Gln Lys Pro Gly Lys Val Pro Lys Leu Leu Ile
            35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

```
Thr Phe Gly Gly Gly Thr Lys Val Glu Ile Lys
                100                 105

<210> SEQ ID NO 47
<211> LENGTH: 107
<212> TYPE: PRT
<213> ORGANISM: Artificial Sequence
<220> FEATURE:
<223> OTHER INFORMATION: Variable light chain region of a humanized CD47
      antibody

<400> SEQUENCE: 47

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile His Arg Tyr
            20                  25                  30

Leu Ser Trp Phe Gln Gln Lys Pro Gly Lys Val Pro Lys Leu Leu Ile
        35                  40                  45

Tyr Arg Ala Asn Arg Leu Val Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
                100                 105

<210> SEQ ID NO 48
<211> LENGTH: 323
<212> TYPE: PRT
<213> ORGANISM: Homo sapiens

<400> SEQUENCE: 48

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190
```

-continued

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Lys Thr Ile Gln Pro Pro Arg Lys
            290                 295                 300

Ala Val Glu Glu Pro Leu Asn Ala Phe Lys Glu Ser Lys Gly Met Met
305                 310                 315                 320

Asn Asp Glu

<210> SEQ ID NO 49
<211> LENGTH: 116
<212> TYPE: PRT
<213> ORGANISM: Homo sapiens

<400> SEQUENCE: 49

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val
        115

<210> SEQ ID NO 50
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 50

Gly Phe Asn Ile Lys Asp Tyr Tyr Leu His
1               5                   10

<210> SEQ ID NO 51
<211> LENGTH: 10
<212> TYPE: PRT
<213> ORGANISM: Artificial Sequence
<220> FEATURE:
<223> OTHER INFORMATION: amino acid sequence of VH CDR2

```
<400> SEQUENCE: 51

Trp Ile Asp Pro Asp Asn Gly Asp Thr Glu
1               5                   10

<210> SEQ ID NO 52
<211> LENGTH: 13
<212> TYPE: PRT
<213> ORGANISM: Artificial Sequence
<220> FEATURE:
<223> OTHER INFORMATION: amino acid sequence of VH CDR3

<400> SEQUENCE: 52

Asn Ala Ala Tyr Gly Ser Ser Ser Tyr Pro Met Asp Tyr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: amino acid sequence of VL CDR1

<400> SEQUENCE: 53

Lys Ala Ser Gln Asp Ile His Arg Tyr Leu Ser
1               5                   10

<210> SEQ ID NO 54
<211> LENGTH: 7
<212> TYPE: PRT
<213> ORGANISM: Artificial Sequence
<220> FEATURE:
<223> OTHER INFORMATION: amino acid sequence of VL CDR2

<400> SEQUENCE: 54

Arg Ala Asn Arg Leu Val Asp
1               5

<210> SEQ ID NO 55
<211> LENGTH: 9
<212> TYPE: PRT
<213> ORGANISM: Artificial Sequence
<220> FEATURE:
<223> OTHER INFORMATION: amino acid sequence of VL CDR3

<400> SEQUENCE: 55

Leu Gln Tyr Asp Glu Phe Pro Tyr Thr
1               5

<210> SEQ ID NO 56
<211> LENGTH: 4
<212> TYPE: PRT
<213> ORGANISM: Homo sapiens

<400> SEQUENCE: 56

Lys Gly Arg Asp
1

<210> SEQ ID NO 57
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 57
```

```
Gly Tyr Thr Phe Thr Tyr Tyr Leu His
1               5                   10
```

<210> SEQ ID NO 58
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 58

```
Gly Phe Thr Phe Thr Tyr Tyr Leu His
1               5                   10
```

<210> SEQ ID NO 59
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 59

```
Gly Tyr Asn Phe Thr Tyr Tyr Leu His
1               5                   10
```

<210> SEQ ID NO 60
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 60

```
Gly Tyr Thr Ile Thr Tyr Tyr Leu His
1               5                   10
```

<210> SEQ ID NO 61
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 61

```
Gly Tyr Thr Phe Lys Tyr Tyr Leu His
1               5                   10
```

<210> SEQ ID NO 62
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 62

```
Gly Tyr Thr Phe Thr Asp Tyr Tyr Leu His
1               5                   10
```

<210> SEQ ID NO 63
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 63

Gly Phe Thr Phe Thr Asp Tyr Tyr Leu His

```
1               5                   10
```

<210> SEQ ID NO 64
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 64

```
Gly Phe Thr Ile Thr Asp Tyr Tyr Leu His
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 65

```
Gly Tyr Thr Phe Lys Asp Tyr Tyr Leu His
1               5                   10
```

<210> SEQ ID NO 66
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 66

```
Gly Phe Thr Phe Lys Asp Tyr Tyr Leu His
1               5                   10
```

<210> SEQ ID NO 67
<211> LENGTH: 11
<212> TYPE: PRT
<213> ORGANISM: Artificial Sequence
<220> FEATURE:
<223> OTHER INFORMATION: amino acid sequence of VL CDR1

<400> SEQUENCE: 67

```
Arg Ala Ser Gln Asp Ile His Arg Tyr Leu Ala
1               5                   10
```

<210> SEQ ID NO 68
<211> LENGTH: 11
<212> TYPE: PRT
<213> ORGANISM: Artificial Sequence
<220> FEATURE:
<223> OTHER INFORMATION: amino acid sequence of VL CDR1

<400> SEQUENCE: 68

```
Arg Ala Arg Gln Gly Ile His Arg Tyr Leu Ser
1               5                   10
```

<210> SEQ ID NO 69
<211> LENGTH: 7
<212> TYPE: PRT
<213> ORGANISM: Artificial Sequence
<220> FEATURE:
<223> OTHER INFORMATION: amino acid sequence of VL CDR2

<400> SEQUENCE: 69

```
Arg Ala Asn Arg Leu Gln Ser
1               5
```

```
<210> SEQ ID NO 70
<211> LENGTH: 7
<212> TYPE: PRT
<213> ORGANISM: Artificial Sequence
<220> FEATURE:
<223> OTHER INFORMATION: amino acid sequence of VL CDR2

<400> SEQUENCE: 70

Arg Ala Asn Arg Arg Ala Thr
1               5

<210> SEQ ID NO 71
<211> LENGTH: 7
<212> TYPE: PRT
<213> ORGANISM: Artificial Sequence
<220> FEATURE:
<223> OTHER INFORMATION: amino acid sequence of VL CDR2

<400> SEQUENCE: 71

Arg Ala Asn Arg Leu Val Ser
1               5

<210> SEQ ID NO 72
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 72

Trp Ile Asp Pro Asp Gln Gly Asp Thr Glu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 73

Trp Ile Asp Pro Asp Tyr Gly Asp Thr Glu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 74

Trp Ile Asp Pro Asp Ser Gly Asp Thr Glu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 75

Trp Ile Asp Pro Asp Asn Ala Asp Thr Glu
1               5                   10
```

```
<210> SEQ ID NO 76
<211> LENGTH: 10
<212> TYPE: PRT
<213> ORGANISM: Artificial Sequence
<220> FEATURE:
<223> OTHER INFORMATION: amino acid sequence of VH CDR1

<400> SEQUENCE: 76

Trp Ile Asp Pro Asp Asn Thr Asp Thr Glu
1               5                   10

<210> SEQ ID NO 77
<211> LENGTH: 13
<212> TYPE: PRT
<213> ORGANISM: Artificial Sequence
<220> FEATURE:
<223> OTHER INFORMATION: amino acid sequence of VH CDR3

<400> SEQUENCE: 77

Asn Ala Ala Tyr Gly Ser Ser Pro Tyr Pro Met Asp Tyr
1               5                   10

<210> SEQ ID NO 78
<211> LENGTH: 118
<212> TYPE: PRT
<213> ORGANISM: Artificial Sequence
<220> FEATURE:
<223> OTHER INFORMATION: VH chain region of the 9E4 antibody

<400> SEQUENCE: 78

Glu Val Gln Leu Arg Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Met Tyr Trp Val Lys Gln Ser Arg Val Arg Ser Leu Ala Trp Ile
        35                  40                  45

Gly Arg Ile Asn Pro Tyr Thr Gly Ala Thr Gly Tyr Asp Gln Asn Phe
    50                  55                  60

Lys Asp Lys Ala Ser Leu Ile Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Arg Asn Arg Tyr Asp Gly Trp Phe Ala Tyr Trp Gly Gln
            100                 105                 110

Gly Thr Leu Val Thr Val
        115

<210> SEQ ID NO 79
<211> LENGTH: 107
<212> TYPE: PRT
<213> ORGANISM: Artificial Sequence
<220> FEATURE:
<223> OTHER INFORMATION: VL chain region of the 9E4 antibody

<400> SEQUENCE: 79

Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45
```

```
Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Gly Asn Ala Leu Pro Pro
                 85                  90                  95

Thr Phe Gly Gly Gly Thr Asn Leu Glu Ile Lys
            100                 105
```

<210> SEQ ID NO 80
<211> LENGTH: 115
<212> TYPE: PRT
<213> ORGANISM: Artificial Sequence
<220> FEATURE:
<223> OTHER INFORMATION: VH chain region of the 1B4 antibody

<400> SEQUENCE: 80

```
Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Lys Arg Pro Gly Gln Gly Leu Glu Trp Ile
            35                  40                  45

Gly Trp Ile Tyr Pro Gly Ser Gly Asn Thr Lys Tyr Asn Glu Arg Phe
50                  55                  60

Lys Gly Lys Ala Thr Leu Thr Val Ala Thr Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Arg Glu Glu Asp Tyr Phe Asp Tyr Trp Gly Gln Gly Thr Leu
                100                 105                 110

Val Thr Val
        115
```

<210> SEQ ID NO 81
<211> LENGTH: 113
<212> TYPE: PRT
<213> ORGANISM: Artificial Sequence
<220> FEATURE:
<223> OTHER INFORMATION: VL chain region of the 1B4 antibody

<400> SEQUENCE: 81

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Thr Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Ile
                100                 105                 110

Lys
```

<210> SEQ ID NO 82
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 82
cactgcaggt rtccactcc                                               19

<210> SEQ ID NO 83
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 83
catagcaggt gtccactcc                                               19

<210> SEQ ID NO 84
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 84
crctacaggt gtccactcc                                               19

<210> SEQ ID NO 85
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 85
gcyacagmtg tccactcc                                                18

<210> SEQ ID NO 86
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 86
cactgcaggt gtccwmtcc                                               19

<210> SEQ ID NO 87
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 87
crctrcaggt gtkcactcc                                               19

<210> SEQ ID NO 88
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 88
gctawmggtg tccactcc                                                 18

<210> SEQ ID NO 89
<211> LENGTH: 17
<212> TYPE: DNA
<213> ORGANISM: Artificial Sequence
<220> FEATURE:
<223> OTHER INFORMATION: Chemically synthesized oligonucleotide primer

<400> SEQUENCE: 89
cctcaggtgt ccactcc                                                  17

<210> SEQ ID NO 90
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 90
gctacaggtg ctcactcc                                                 18

<210> SEQ ID NO 91
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 91
cactgcaggt gtcctctct                                                19

<210> SEQ ID NO 92
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 92
caytgcaggt gtccaytgc                                                19

<210> SEQ ID NO 93
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 93
gctammggtg tccacttc                                                 18

<210> SEQ ID NO 94
<211> LENGTH: 21
<212> TYPE: DNA
<213> ORGANISM: Artificial Sequence
<220> FEATURE:
<223> OTHER INFORMATION: Chemically synthesized oligonucleotide primer

<400> SEQUENCE: 94
ctcctgtcak taactkcagg t                                             21

<210> SEQ ID NO 95

```
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 95
caactgcagg tgtctctct                                                19

<210> SEQ ID NO 96
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 96
crctrcaggy gtccactct                                                19

<210> SEQ ID NO 97
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 97
ccaagctgta tcctttcc                                                 18

<210> SEQ ID NO 98
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 98
ccaagctgtg tcctrtcc                                                 18

<210> SEQ ID NO 99
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 99
cttgacagyc vttcckggt                                                19

<210> SEQ ID NO 100
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 100
cttcacagcc tttcctggt                                                19

<210> SEQ ID NO 101
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 101
```
cttaaaaggg gtccagtgt                                          19

<210> SEQ ID NO 102
<211> LENGTH: 22
<212> TYPE: DNA
<213> ORGANISM: Artificial Sequence
<220> FEATURE:
<223> OTHER INFORMATION: Chemically synthesized oligonucleotide primer

<400> SEQUENCE: 102
caytttaaaa rgtgtcmagt gt                                      22

<210> SEQ ID NO 103
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 103
gttttaaaag gtgtcctgtg                                         20

<210> SEQ ID NO 104
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 104
ctyttaaaag gkgtccagwg                                         20

<210> SEQ ID NO 105
<211> LENGTH: 21
<212> TYPE: DNA
<213> ORGANISM: Artificial Sequence
<220> FEATURE:
<223> OTHER INFORMATION: Chemically synthesized oligonucleotide primer

<400> SEQUENCE: 105
cytttamatg gtatccagtg t                                       21

<210> SEQ ID NO 106
<211> LENGTH: 21
<212> TYPE: DNA
<213> ORGANISM: Artificial Sequence
<220> FEATURE:
<223> OTHER INFORMATION: Chemically synthesized oligonucleotide primer

<400> SEQUENCE: 106
cttttacatg gtttcaagtg t                                       21

<210> SEQ ID NO 107
<211> LENGTH: 17
<212> TYPE: DNA
<213> ORGANISM: Artificial Sequence
<220> FEATURE:
<223> OTHER INFORMATION: Chemically synthesized oligonucleotide primer

<400> SEQUENCE: 107
gtccctgcat atgtcyt                                            17

<210> SEQ ID NO 108
<211> LENGTH: 18
<212> TYPE: DNA

```
<213> ORGANISM: Artificial Sequence
<220> FEATURE:
<223> OTHER INFORMATION: Chemically synthesized oligonucleotide primer

<400> SEQUENCE: 108
gatggcagcw gcycaaag                                                       18

<210> SEQ ID NO 109
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 109
ctatcaaggt gtgcattgt                                                      19

<210> SEQ ID NO 110
<211> LENGTH: 21
<212> TYPE: DNA
<213> ORGANISM: Artificial Sequence
<220> FEATURE:
<223> OTHER INFORMATION: Chemically synthesized oligonucleotide primer

<400> SEQUENCE: 110
cttttaaaag wtgtccagkg t                                                   21

<210> SEQ ID NO 111
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 111
gtgacagtcc ttcctggtag                                                     20

<210> SEQ ID NO 112
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 112
cttcctgatg gcagtggtt                                                      19

<210> SEQ ID NO 113
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 113
gctacaggta tccaatcc                                                       18

<210> SEQ ID NO 114
<211> LENGTH: 39
<212> TYPE: DNA
<213> ORGANISM: Artificial Sequence
<220> FEATURE:
<223> OTHER INFORMATION: Chemically synthesized oligonucleotide primer

<400> SEQUENCE: 114
gcgtctagaa yctccacaca caggrrccag tggatagac                                39
```

<210> SEQ ID NO 115
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 115
ctgwtgttct ggattcctg                                            19

<210> SEQ ID NO 116
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 116
ggtcagacag tcagcagt                                             18

<210> SEQ ID NO 117
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 117
gtgctctgga ttcgggaa                                             18

<210> SEQ ID NO 118
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 118
cagcttcytg ctaatcagtg                                           20

<210> SEQ ID NO 119
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 119
ctaatcagtg cttcagga                                             18

<210> SEQ ID NO 120
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 120
gtgggtatct ggtrcstgtg                                           20

<210> SEQ ID NO 121
<211> LENGTH: 23
<212> TYPE: DNA
<213> ORGANISM: Artificial Sequence
<220> FEATURE:

<223> OTHER INFORMATION: Chemically synthesized oligonucleotide primer

<400> SEQUENCE: 121
ggaaatttaa aagtacctgt ggg          23

<210> SEQ ID NO 122
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 122
ggtttcmagg trccagatgt          20

<210> SEQ ID NO 123
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 123
ctctggttyc caggtatc          18

<210> SEQ ID NO 124
<211> LENGTH: 22
<212> TYPE: DNA
<213> ORGANISM: Artificial Sequence
<220> FEATURE:
<223> OTHER INFORMATION: Chemically synthesized oligonucleotide primer

<400> SEQUENCE: 124
ctgttttcaa ggtrccagat gt          22

<210> SEQ ID NO 125
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 125
gttgtaatgt ccagagga          18

<210> SEQ ID NO 126
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 126
cttacaggtg ccagatgt          18

<210> SEQ ID NO 127
<211> LENGTH: 22
<212> TYPE: DNA
<213> ORGANISM: Artificial Sequence
<220> FEATURE:
<223> OTHER INFORMATION: Chemically synthesized oligonucleotide primer

<400> SEQUENCE: 127
ctcaattgta grtgccagat gt          22

```
<210> SEQ ID NO 128
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 128
cacagtaggt gtcagatgt                                              19

<210> SEQ ID NO 129
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 129
gtcgtagttg tcagatgt                                               18

<210> SEQ ID NO 130
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 130
cctccttctt ggccaaga                                               18

<210> SEQ ID NO 131
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 131
cttatatgga gctgatggg                                              19

<210> SEQ ID NO 132
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 132
gtgtctggtg ctcatggg                                               18

<210> SEQ ID NO 133
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 133
ctstggttgt ctggtgttga                                             20

<210> SEQ ID NO 134
<211> LENGTH: 18
<212> TYPE: DNA
<213> ORGANISM: Artificial Sequence
<220> FEATURE:
<223> OTHER INFORMATION: Chemically synthesized oligonucleotide primer
```

```
<400> SEQUENCE: 134
gtctctgatt ctagggca                                                 18

<210> SEQ ID NO 135
<211> LENGTH: 16
<212> TYPE: DNA
<213> ORGANISM: Artificial Sequence
<220> FEATURE:
<223> OTHER INFORMATION: Chemically synthesized oligonucleotide primer

<400> SEQUENCE: 135
ctkckctggg ttccag                                                   16

<210> SEQ ID NO 136
<211> LENGTH: 15
<212> TYPE: DNA
<213> ORGANISM: Artificial Sequence
<220> FEATURE:
<223> OTHER INFORMATION: Chemically synthesized oligonucleotide primer

<400> SEQUENCE: 136
gcaggtgttg acgga                                                    15

<210> SEQ ID NO 137
<211> LENGTH: 16
<212> TYPE: DNA
<213> ORGANISM: Artificial Sequence
<220> FEATURE:
<223> OTHER INFORMATION: Chemically synthesized oligonucleotide primer

<400> SEQUENCE: 137
caggtgcctc gtgcac                                                   16

<210> SEQ ID NO 138
<211> LENGTH: 16
<212> TYPE: DNA
<213> ORGANISM: Artificial Sequence
<220> FEATURE:
<223> OTHER INFORMATION: Chemically synthesized oligonucleotide primer

<400> SEQUENCE: 138
ctctggtgcc tgtgca                                                   16

<210> SEQ ID NO 139
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 139
ctggaytyca gcctccaga                                                19

<210> SEQ ID NO 140
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 140
gwtctctrga gtcagtggg                                                19

<210> SEQ ID NO 141
<211> LENGTH: 19
```

```
<212> TYPE: DNA
<213> ORGANISM: Artificial Sequence
<220> FEATURE:
<223> OTHER INFORMATION: Chemically synthesized oligonucleotide primer

<400> SEQUENCE: 141
ctggatccct ggakcyact                                                  19

<210> SEQ ID NO 142
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 142
gttctgcttt ttaggtgtg                                                  19

<210> SEQ ID NO 143
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 143
gatcccaggc atgatatgt                                                  19

<210> SEQ ID NO 144
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 144
cttcatggtg ctcagtgt                                                   18

<210> SEQ ID NO 145
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 145
ccatatcagg tgcccagtgt                                                 20

<210> SEQ ID NO 146
<211> LENGTH: 29
<212> TYPE: DNA
<213> ORGANISM: Artificial Sequence
<220> FEATURE:
<223> OTHER INFORMATION: Chemically synthesized oligonucleotide primer

<400> SEQUENCE: 146
gcgtctagaa ctggatggtg ggaagatgg                                       29

<210> SEQ ID NO 147
<211> LENGTH: 305
<212> TYPE: PRT
<213> ORGANISM: Homo sapiens

<400> SEQUENCE: 147

Gln Leu Leu Phe Asn Lys Thr Lys Ser Val Glu Phe Thr Phe Cys Asn
1               5                   10                  15
```

-continued

```
Asp Thr Val Val Ile Pro Cys Phe Val Thr Asn Met Glu Ala Gln Asn
             20                  25              30

Thr Thr Glu Val Tyr Val Lys Trp Lys Phe Lys Gly Arg Asp Ile Tyr
         35              40                  45

Thr Phe Asp Gly Ala Leu Asn Lys Ser Thr Val Pro Thr Asp Phe Ser
     50              55                  60

Ser Ala Lys Ile Glu Val Ser Gln Leu Leu Lys Gly Asp Ala Ser Leu
65               70                  75                      80

Lys Met Asp Lys Ser Asp Ala Val Ser His Thr Gly Asn Tyr Thr Cys
                 85                  90                  95

Glu Val Thr Glu Leu Thr Arg Glu Gly Glu Thr Ile Ile Glu Leu Lys
             100                 105             110

Tyr Arg Val Val Ser Trp Phe Ser Pro Asn Glu Asn Ile Leu Ile Val
             115                 120                 125

Ile Phe Pro Ile Phe Ala Ile Leu Leu Phe Trp Gly Gln Phe Gly Ile
         130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                 165                 170                 175

Ile Leu Phe Val Pro Gly Glu Tyr Ser Leu Lys Asn Ala Thr Gly Leu
             180                 185                 190

Gly Leu Ile Val Thr Ser Thr Gly Ile Leu Ile Leu Leu His Tyr Tyr
             195                 200                 205

Val Phe Ser Thr Ala Ile Gly Leu Thr Ser Phe Val Ile Ala Ile Leu
             210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                 245                 250                 255

Leu Ser Ile Leu Ala Leu Ala Gln Leu Leu Gly Leu Val Tyr Met Lys
             260                 265                 270

Phe Val Ala Ser Asn Gln Lys Thr Ile Gln Pro Pro Arg Lys Ala Val
             275                 280                 285

Glu Glu Pro Leu Asn Ala Phe Lys Glu Ser Lys Gly Met Met Asn Asp
     290                 295                 300

Glu
305
```